US010750981B2

(12) United States Patent
Newberry

(10) Patent No.: US 10,750,981 B2
(45) Date of Patent: Aug. 25, 2020

(54) SYSTEM AND METHOD FOR HEALTH MONITORING INCLUDING A REMOTE DEVICE

(71) Applicant: Sanmina Corporation, San Jose, CA (US)

(72) Inventor: Robert Steven Newberry, New Hope, AL (US)

(73) Assignee: SANMINA CORPORATION, San Jose, CA (US)

(*) Notice: Subject to any disclaimer, the term of this patent is extended or adjusted under 35 U.S.C. 154(b) by 472 days.

(21) Appl. No.: 15/400,916

(22) Filed: Jan. 6, 2017

(65) Prior Publication Data
US 2017/0181678 A1 Jun. 29, 2017

Related U.S. Application Data

(63) Continuation-in-part of application No. 15/276,760, filed on Sep. 26, 2016, now Pat. No. 9,636,457, and
(Continued)

(51) Int. Cl.
A61B 5/1455 (2006.01)
A61M 5/145 (2006.01)
(Continued)

(52) U.S. Cl.
CPC ........ *A61B 5/14532* (2013.01); *A61B 5/0008* (2013.01); *A61B 5/0022* (2013.01);
(Continued)

(58) Field of Classification Search
None
See application file for complete search history.

(56) References Cited

U.S. PATENT DOCUMENTS 4,913,150 A   4/1990  Cheung et al.
5,115,133 A   5/1992  Knudson
(Continued)

FOREIGN PATENT DOCUMENTS

CN   102609627 A   7/2012
EP   2017001250 A1   1/2017
(Continued)

OTHER PUBLICATIONS

KC Mahesh et al., Wearable Wireless Intelligent Multi-Parameter Health Monitoring Watch, 2013, Texas Instruments India Educators' Conference, IEEE, p. 61-64.
(Continued)

*Primary Examiner* — Eric F Winakur
*Assistant Examiner* — Marjan Fardanesh
(74) *Attorney, Agent, or Firm* — Loza & Loza, LLP; Julio M. Loza; Jessica W. Smith

(57) ABSTRACT

A remote device includes a biosensor interface that is configured to collect biosensor data from an integrated biosensor or by receiving biosensor data from one or more external biosensors or other types of sensors either through a wireless connection or a wired connection. The remote device communicates with a television to display the biosensor data on the television. The television may communicate biosensor data to third party, such as a pharmacy or physician's office or service provider.

17 Claims, 29 Drawing Sheets

Related U.S. Application Data a continuation-in-part of application No. 15/275,444, filed on Sep. 25, 2016, now Pat. No. 9,642,538, and a continuation-in-part of application No. 15/275,388, filed on Sep. 24, 2016, now Pat. No. 9,642,578, and a continuation-in-part of application No. 14/866,500, filed on Sep. 25, 2015, now Pat. No. 10,321,860.

(60) Provisional application No. 62/276,934, filed on Jan. 10, 2016.

(51) Int. Cl.
| | | |
|---|---|---|
| *A61B 5/11* | (2006.01) | |
| *A61M 5/172* | (2006.01) | |
| *A61B 5/024* | (2006.01) | |
| *A61B 5/145* | (2006.01) | |
| *A61B 5/00* | (2006.01) | |
| *A61M 5/142* | (2006.01) | |
| *G06F 19/00* | (2018.01) | |
| *G16H 40/67* | (2018.01) | |

(52) U.S. Cl.
CPC ........ *A61B 5/02416* (2013.01); *A61B 5/1118* (2013.01); *A61B 5/1455* (2013.01); *A61B 5/14551* (2013.01); *A61B 5/4839* (2013.01); *A61B 5/6817* (2013.01); *A61B 5/6826* (2013.01); *A61B 5/743* (2013.01); *A61M 5/1452* (2013.01); *A61M 5/14248* (2013.01); *A61M 5/1723* (2013.01); *G06F 19/00* (2013.01); *G16H 40/67* (2018.01); *A61B 5/0002* (2013.01); *A61B 2560/0223* (2013.01); *A61M 2205/3553* (2013.01); *A61M 2205/3584* (2013.01); *A61M 2230/06* (2013.01)

(56) References Cited

U.S. PATENT DOCUMENTS

| | | | |
|---|---|---|---|
| 5,269,310 A | 12/1993 | Jones et al. | |
| 5,358,703 A | 10/1994 | Lai | |
| 5,515,847 A | 5/1996 | Braig et al. | |
| 5,673,692 A | 10/1997 | Schulze et al. | |
| 5,823,966 A | 10/1998 | Buchert | |
| 5,947,911 A * | 9/1999 | Wong | A61B 5/14557 600/309 |
| 5,983,121 A | 11/1999 | Tsuchiya | |
| 6,087,087 A | 7/2000 | Yonetani et al. | |
| 6,280,390 B1 | 8/2001 | Akselrod et al. | |
| 6,285,896 B1 * | 9/2001 | Tobler | A61B 5/14542 600/310 |
| 6,305,804 B1 | 10/2001 | Rice et al. | |
| 6,537,225 B1 | 3/2003 | Mills | |
| 6,694,180 B1 | 2/2004 | Boesen | |
| 6,719,705 B2 | 4/2004 | Mills | |
| 6,819,950 B2 | 11/2004 | Mills | |
| 6,921,367 B2 | 7/2005 | Mills | |
| 6,985,763 B2 | 1/2006 | Boas et al. | |
| 7,142,901 B2 * | 11/2006 | Kiani | A61B 5/14535 600/331 |
| 7,154,592 B2 | 12/2006 | Reynolds et al. | |
| 7,167,736 B2 | 1/2007 | Winther | |
| 7,171,251 B2 | 1/2007 | Sarussi et al. | |
| 7,179,228 B2 | 2/2007 | Banet | |
| 7,209,775 B2 | 4/2007 | Bae et al. | |
| 7,291,497 B2 | 11/2007 | Holmes et al. | |
| 7,371,562 B2 | 5/2008 | Cunningham et al. | |
| 7,608,045 B2 | 10/2009 | Mills | |
| 7,647,083 B2 | 1/2010 | Al-Ali et al. | |
| 7,761,127 B2 | 7/2010 | Al-Ali et al. | |
| 7,763,472 B2 | 7/2010 | Doctor et al. | |
| 7,764,982 B2 | 7/2010 | Dalke et al. | |
| 7,941,199 B2 | 5/2011 | Kiani | |
| 8,224,411 B2 | 7/2012 | Al-Ali et al. | |
| 8,255,027 B2 | 8/2012 | Al-Ali et al. | |
| 8,328,420 B2 | 12/2012 | Abreu | |
| 8,385,996 B2 | 2/2013 | Smith et al. | |
| 8,401,605 B2 | 3/2013 | Huiku | |
| 8,483,787 B2 | 7/2013 | Al-Ali et al. | |
| 8,494,507 B1 | 7/2013 | Tedesco et al. | |
| 8,597,274 B2 | 12/2013 | Sloan et al. | |
| 8,652,040 B2 | 2/2014 | Leboeuf et al. | |
| 8,676,284 B2 | 3/2014 | He | |
| 8,730,047 B2 | 5/2014 | Ridder et al. | |
| 8,868,149 B2 | 10/2014 | Eisen et al. | |
| 8,888,701 B2 | 11/2014 | Leboeuf et al. | |
| 8,906,693 B2 | 12/2014 | Schultz et al. | |
| 8,923,918 B2 | 12/2014 | Kreger et al. | |
| 8,961,932 B2 | 2/2015 | Silverman | |
| 9,022,973 B2 | 5/2015 | Sexton et al. | |
| 9,131,882 B2 | 9/2015 | Al-Ali et al. | |
| 9,149,216 B2 | 10/2015 | Eisen et al. | |
| 9,149,646 B2 | 10/2015 | Keswarpu et al. | |
| 9,387,033 B2 | 7/2016 | Yodfat et al. | |
| 9,442,092 B2 | 9/2016 | Lane | |
| 9,521,970 B2 | 12/2016 | Hoppe et al. | |
| 9,554,738 B1 | 1/2017 | Gulati et al. | |
| 9,642,578 B2 | 5/2017 | Newberry | |
| 9,668,701 B2 | 6/2017 | Maarek | |
| 9,713,428 B2 | 7/2017 | Chon et al. | |
| 9,739,663 B2 | 8/2017 | Halder et al. | |
| 9,820,656 B2 | 11/2017 | Olivier | |
| 9,839,381 B1 | 12/2017 | Weber et al. | |
| 9,924,895 B2 | 3/2018 | Rawicz et al. | |
| 9,949,675 B2 | 4/2018 | Miller | |
| 9,999,355 B2 | 6/2018 | Kirenko | |
| 10,028,682 B2 | 7/2018 | Thiele | |
| D824,937 S | 8/2018 | Sparandara et al. | |
| 10,099,554 B2 | 10/2018 | Steeg et al. | |
| 10,130,285 B1 | 11/2018 | Singamsetty et al. | |
| 10,153,796 B2 | 12/2018 | Fung et al. | |
| 10,181,021 B2 | 1/2019 | Venkatraman et al. | |
| 10,206,619 B1 | 2/2019 | Lee et al. | |
| 10,215,698 B2 | 2/2019 | Han et al. | |
| 10,227,063 B2 | 3/2019 | Abreu | |
| 10,232,156 B2 | 3/2019 | Netzel et al. | |
| 10,278,591 B2 | 5/2019 | Gil | |
| D850,316 S | 6/2019 | Ennis et al. | |
| 10,314,500 B2 | 6/2019 | Olivier | |
| 10,322,728 B1 | 6/2019 | Porikli et al. | |
| 10,342,495 B2 | 7/2019 | Melkoniemi et al. | |
| 10,349,847 B2 | 7/2019 | Kwon et al. | |
| 10,420,470 B2 | 9/2019 | Kwon et al. | |
| 10,420,491 B2 | 9/2019 | Rajan et al. | |
| 10,433,726 B2 | 10/2019 | Ramesh et al. | |
| 10,433,738 B2 | 10/2019 | Thomas et al. | |
| 10,433,739 B2 | 10/2019 | Weekly et al. | |
| 10,463,283 B2 | 11/2019 | Ferber et al. | |
| 2002/0049389 A1 | 4/2002 | Abreu | |
| 2003/0229276 A1 | 12/2003 | Sarussi et al. | |
| 2004/0078219 A1 | 4/2004 | Kaylor et al. | |
| 2004/0100376 A1 | 5/2004 | Lye et al. | |
| 2004/0157341 A1 | 8/2004 | Reynolds et al. | |
| 2005/0101841 A9 | 5/2005 | Kaylor et al. | |
| 2005/0209516 A1 | 9/2005 | Fraden | |
| 2005/0228244 A1 | 10/2005 | Banet | |
| 2005/0228299 A1 | 10/2005 | Banet | |
| 2005/0245831 A1 | 11/2005 | Banet | |
| 2006/0009698 A1 | 1/2006 | Banet | |
| 2006/0094942 A1 | 5/2006 | Winther | |
| 2006/0287589 A1 | 12/2006 | Wobermin et al. | |
| 2007/0202605 A1 | 8/2007 | Doctor et al. | |
| 2007/0203405 A1 | 8/2007 | Shimomura | |
| 2007/0260132 A1 | 11/2007 | Sterling | |
| 2008/0146890 A1 | 6/2008 | Leboeuf et al. | |
| 2008/0165017 A1 | 7/2008 | Schwartz | |
| 2008/0208019 A1 | 8/2008 | Nitzan | |
| 2008/0241199 A1 | 10/2008 | Silverman | |
| 2009/0043178 A1 * | 2/2009 | Belotserkovsky | A61B 5/14532 600/310 |
| 2009/0156988 A1 | 6/2009 | Ferren et al. | |
| 2009/0187167 A1 | 7/2009 | Sexton et al. | |

(56) References Cited

U.S. PATENT DOCUMENTS

| | | |
|---|---|---|
| 2009/0287120 A1 | 11/2009 | Ferren et al. |
| 2010/0049020 A1 | 2/2010 | Dalke et al. |
| 2010/0191080 A1 | 7/2010 | Mills |
| 2010/0274101 A1 | 10/2010 | Lin et al. |
| 2010/0331631 A1 | 12/2010 | MacLaughlin |
| 2011/0082355 A1 | 4/2011 | Eisen et al. |
| 2011/0106050 A1 | 5/2011 | Yodfat et al. |
| 2011/0137141 A1 | 6/2011 | Razoumov et al. |
| 2011/0160697 A1 | 6/2011 | Yodfat et al. |
| 2011/0166553 A1 | 7/2011 | Holmes et al. |
| 2011/0224518 A1 | 9/2011 | Tindi et al. |
| 2011/0237464 A1 | 9/2011 | Cunningham et al. |
| 2011/0275978 A1 | 11/2011 | Hyde et al. |
| 2012/0010683 A1 | 1/2012 | Keswarpu et al. |
| 2012/0029363 A1 | 2/2012 | Lund |
| 2012/0095302 A1 | 4/2012 | Adhikari |
| 2012/0131507 A1 | 5/2012 | Sparandara et al. |
| 2012/0136054 A1 | 5/2012 | Schultz et al. |
| 2012/0156933 A1 | 6/2012 | Kreger et al. |
| 2012/0203077 A1 | 8/2012 | He et al. |
| 2012/0238844 A1 | 9/2012 | Grata et al. |
| 2012/0330126 A1 | 12/2012 | Hoppe et al. |
| 2013/0030259 A1 | 1/2013 | Thomsen et al. |
| 2013/0060098 A1 | 3/2013 | Thomsen et al. |
| 2013/0066176 A1 | 3/2013 | Addison et al. |
| 2013/0110311 A1 | 5/2013 | Ver Steeg et al. |
| 2013/0131474 A1* | 5/2013 | Gu ............... A61B 5/0205 600/324 |
| 2013/0310669 A1 | 11/2013 | Nitzan |
| 2014/0046160 A1 | 2/2014 | Terashima et al. |
| 2014/0100432 A1 | 4/2014 | Golda et al. |
| 2014/0112940 A1 | 4/2014 | Lane |
| 2014/0194342 A1 | 7/2014 | Zhang et al. |
| 2014/0243648 A1 | 8/2014 | Dubielczyk |
| 2014/0253709 A1 | 9/2014 | Bresch et al. |
| 2014/0275852 A1 | 9/2014 | Hong et al. |
| 2014/0297313 A1 | 10/2014 | Condurso et al. |
| 2014/0316226 A1 | 10/2014 | Ferber et al. |
| 2015/0066238 A1 | 3/2015 | Todd et al. |
| 2015/0088007 A1 | 3/2015 | Bardy et al. |
| 2015/0094914 A1 | 4/2015 | Abreu |
| 2015/0105638 A1 | 4/2015 | Eisen et al. |
| 2015/0109617 A1 | 4/2015 | Gilbert et al. |
| 2015/0148622 A1 | 5/2015 | Moyer et al. |
| 2015/0148635 A1 | 5/2015 | Benaron |
| 2015/0150453 A1 | 6/2015 | Abreu |
| 2015/0182172 A1 | 7/2015 | Shelley et al. |
| 2015/0229341 A1* | 8/2015 | Fung ............... H04B 1/10 702/191 |
| 2015/0250404 A1 | 9/2015 | Maarek |
| 2015/0282747 A1 | 10/2015 | Thiele |
| 2015/0366471 A1 | 12/2015 | Leboeuf et al. |
| 2016/0018257 A1 | 1/2016 | Mirov et al. |
| 2016/0058308 A1 | 3/2016 | Robinson |
| 2016/0058347 A1 | 3/2016 | Reichgott et al. |
| 2016/0066863 A1 | 3/2016 | Thaveeprungsrporn et al. |
| 2016/0100781 A1 | 4/2016 | Bechtel et al. |
| 2016/0262707 A1 | 9/2016 | Devries |
| 2016/0367154 A1 | 12/2016 | Gladshtein et al. |
| 2017/0027521 A1 | 2/2017 | Geva et al. |
| 2017/0050518 A1 | 2/2017 | Steeg et al. |
| 2017/0071550 A1 | 3/2017 | Newberry |
| 2017/0091436 A1 | 3/2017 | Cao et al. |
| 2017/0172477 A1 | 6/2017 | Adusumilli et al. |
| 2017/0215811 A1 | 8/2017 | Newberry |
| 2017/0256110 A1 | 9/2017 | Divincent et al. |
| 2017/0347894 A1 | 12/2017 | Bhushan et al. |
| 2017/0347899 A1 | 12/2017 | Bhushan et al. |
| 2018/0117291 A1 | 5/2018 | Netzel et al. |
| 2018/0140210 A1 | 5/2018 | Jelfs et al. |
| 2018/0140237 A1 | 5/2018 | Rajan et al. |
| 2018/0177416 A1 | 6/2018 | Church et al. |
| 2018/0177440 A1 | 6/2018 | Jelfs et al. |
| 2018/0200433 A1 | 7/2018 | Cirit |
| 2018/0264242 A1 | 9/2018 | Hoffman et al. |
| 2018/0353137 A1 | 12/2018 | Balajadia et al. |
| 2018/0358119 A1 | 12/2018 | Bhushan et al. |
| 2019/0046039 A1 | 2/2019 | Ramesh et al. |
| 2019/0050622 A1 | 2/2019 | Cabibihan et al. |
| 2019/0086331 A1 | 3/2019 | Han |
| 2019/0099114 A1 | 4/2019 | Mouradian et al. |
| 2019/0110745 A1 | 4/2019 | Linnes et al. |
| 2019/0125963 A1 | 5/2019 | Mou et al. |
| 2019/0125964 A1 | 5/2019 | Mou et al. |
| 2019/0133471 A1 | 5/2019 | Olson et al. |
| 2019/0192085 A1 | 6/2019 | Krishna et al. |
| 2019/0192086 A1 | 6/2019 | Krishna et al. |
| 2019/0251238 A1 | 8/2019 | Venkatraman et al. |
| 2019/0358387 A1 | 11/2019 | Elbadry et al. |

FOREIGN PATENT DOCUMENTS

| | | | |
|---|---|---|---|
| EP | 3488776 | A1 | 5/2019 |
| WO | 2004047630 | A1 | 6/2004 |
| WO | 2007013054 | A1 | 2/2007 |
| WO | 2008006150 | A1 | 1/2008 |
| WO | 2010128852 | A3 | 11/2010 |
| WO | 2010147968 | A1 | 12/2010 |
| WO | 2012108895 | A1 | 8/2012 |
| WO | 2013052318 | A1 | 4/2013 |
| WO | 2013127564 | A1 | 9/2013 |
| WO | 2014163583 | A1 | 10/2014 |
| WO | 2015143197 | A1 | 9/2015 |
| WO | 2015200148 | A1 | 12/2015 |
| WO | 2017001249 | A1 | 1/2017 |
| WO | 2018206875 | A1 | 11/2018 |
| WO | 2019030700 | A1 | 2/2019 |
| WO | 2019118053 | A1 | 6/2019 |

OTHER PUBLICATIONS

Abdallah et al., Design of a Compact Multi-Sensor System for Non-Invasive Glucose Monitoring Using Optical Spectroscopy, International Conference on Electronics, Biomedical Engineering and its Applications (ICEBEA'2012), Jan. 7-8, 2012, p. 310-317.

Forst et al., Cardiovascular Effects of Disturbed Insulin Activity in Metabolic Syndrome and in Type 2 Diabetic Patients, Insulin Secretion and Action, Horm Metab Res; 2009, 41; p. 123-131.

Mohamed Elgendi, On the Analysis of Fingertip Photoplethysmogram Signals, Current Cardiology Reviews, 2012, 8, p. 14-25, Bentham Science Publishers.

Wikipedia, Cytochrome P450, Dec. 31, 2015, p. 1-12.

Oliver Wieben, Light Absorbance in Pulse Oximetry, Taylor & Francis, 1997, IOP Publishing, p. 1-20.

Wikipedia, Photoplethysmogram, Jul. 25, 2015, p. 1-4.

\* cited by examiner

SYSTEM AND METHOD FOR HEALTH MONITORING INCLUDING A REMOTE DEVICE

CLAIM OF PRIORITY UNDER 35 U.S.C. § 119 AND $120

The present application claims priority under 35 U.S.C. § 119 to U.S. Provisional Application No. 62/276,934 entitled, "SYSTEM AND METHOD FOR HEALTH MONITORING INCLUDING A REMOTE DEVICE," filed Jan. 10, 2016, and hereby expressly incorporated by reference herein.

The present application claims priority under 35 U.S.C. § 120 as a continuation in part to U.S. patent application Ser. No. 14/866,500 entitled, "SYSTEM AND METHOD FOR GLUCOSE MONITORING," filed Sep. 25, 2015, and hereby expressly incorporated by reference herein.

The present application claims priority under 35 U.S.C. § 120 as a continuation in part application to U.S. patent application Ser. No. 15/275,388 entitled, "SYSTEM AND METHOD FOR HEALTH MONITORING USING A NON-INVASIVE, MULTI-BAND BIOSENSOR," filed Sep. 24, 2016 and hereby expressly incorporated by reference herein.

The present application claims priority under 35 U.S.C. § 120 as a continuation in part application to U.S. patent application Ser. No. 15/275,444 entitled, "SYSTEM AND METHOD FOR A BIOSENSOR MONITORING AND TRACKING BAND," filed Sep. 25, 2016 and hereby expressly incorporated by reference herein.

The present application claims priority under 35 U.S.C. § 120 as a continuation in part application to U.S. patent application Ser. No. 15/276,760 entitled, "SYSTEM AND METHOD FOR A DRUG DELIVERY AND BIOSENSOR PATCH," filed Sep. 26, 2016 and hereby expressly incorporated by reference herein.

FIELD

This application relates to systems and methods of non-invasive, autonomous health monitoring and drug administration using a biosensor and remote device.

BACKGROUND

Various techniques are available for obtaining biosensor measurements, such as blood glucose levels in patients with diabetes. One technique requires a small blood sample from the patients, e.g. from a finger prick. The blood sample is placed on a chemically prepared test strip and inserted into a glucose meter that analyzes the test strip and provides a blood glucose level. Unfortunately, to monitor their blood glucose levels, diabetics may need to prick their fingers multiple times within a day. This monitoring process can be painful, inconvenient and creates possible exposure to infections. Additionally, measurements with these devices present an error of uncertainty range between approximately 10-20% depending on sample quality, human error, calibration, humidity, and hygiene in the sample area. Thus, there is a need for an accurate, non-invasive blood analytic and glucose monitoring and tracking system and method and device that eliminates the pain of drawing blood as well as eliminates a source of potential infection.

In addition, there is a need for accurate and non-invasive biosensor measurements, such as pulse, blood oxygen level, electrolyte levels, etc. It is important to provide a convenient system for monitoring and tracking these biosensor measurements.

In addition, there is a need for a more accurate and non-invasive drug administration based on biosensor monitoring and feedback.

SUMMARY

According to a first aspect, a remote device includes a television control circuit configured to control a television in response to user input and a biosensor. The biosensor includes a temperature sensor configured to obtain a temperature of a user, and a PPG circuit configured to emit light at a plurality of wavelengths directed at skin of the user and obtain a plurality of spectral responses at each of the plurality of wavelengths of light reflected from the skin. The processing circuit is configured to process the spectral responses at the plurality of wavelengths and determine biosensor data using the spectral responses, wherein the biosensor data includes oxygen saturation levels and concentration levels of one or more additional substances in arterial blood flow using the spectral responses. The remote device further includes a wireless transceiver configured to transmit the temperature and biosensor data to the television.

According to a second aspect, a remote device includes a television control circuit configured to control a television in response to user input and a wireless transceiver configured to communicate with one or more external biosensors and a television. The remote device further includes a processing circuit configured to receive biosensor data from the one or more external biosensors and transmit the biosensor data to the television for display.

According to a third aspect, the television is configured to display the temperature and the biosensor data in one or more graphical user interfaces.

According to a fourth aspect, the remote device is configured to generate a command to a drug administrative device to administer medicine.

According to a fifth aspect, the remote device is configured to generate the command to the drug administration device to administer insulin in response to a blood glucose concentration level exceeding a predetermined threshold.

According to a sixth aspect, the television includes a wireless transceiver configured to communicate with a remote device, wherein the wireless transceiver receives biosensor data from the remote device and a processing device configured to generate a graphical user interface (GUI) that displays the biosensor data and transmit the biosensor data to a third party service provider.

According to a seventh aspect, the biosensor data includes a heart rate and activity level.

DETAILED DESCRIPTION

The word "exemplary" or "embodiment" is used herein to mean "serving as an example, instance, or illustration." Any implementation or aspect described herein as "exemplary" or as an "embodiment" is not necessarily to be construed as preferred or advantageous over other aspects of the disclosure. Likewise, the term "aspects" does not require that all aspects of the disclosure include the discussed feature, advantage, or mode of operation.

Embodiments will now be described in detail with reference to the accompanying drawings. In the following description, numerous specific details are set forth in order to provide a thorough understanding of the aspects described herein. It will be apparent, however, to one skilled in the art, that these and other aspects may be practiced without some or all of these specific details. In addition, well known steps in a method of a process may be omitted from flow diagrams presented herein in order not to obscure the aspects of the disclosure. Similarly, well known components in a device may be omitted from figures and descriptions thereof presented herein in order not to obscure the aspects of the disclosure.

Overview—Remote Device

The remote device includes a biosensor interface that is configured to collect biosensor data from an integrated biosensor or by receiving biosensor data from one or more external biosensors or other types of sensors either through a wireless connection or a wired connection. In an embodiment, the remote device is a television remote control and communicates with a television to control channel changing and other operations of the television. For example, the remote device may have a primary purpose of controlling the television or only have capabilities of communicating with and controlling the television.

In an embodiment, the one or more biosensors may include a pulse oximeter configured to detect pulse and blood oxygen levels. The one or more biosensors may also include a temperature sensor to detect body temperature. In an embodiment, at least one biosensor includes a PPG circuit configured to detect one or more substances in blood, such as an indicator of glucose levels in arterial blood flow or blood levels of other substances, such as bilirubin, sodium, potassium. The biosensor may also detect blood alcohol levels. The one or more biosensors may communicate either wirelessly or through a wired connection to the remote device or be incorporated into the remote device. The remote device then communicates with a television that includes a Health Monitoring (HM) application. The HM application is configured to receive biosensor data from the remote device and display the biosensor data on the display. The HM application may also communicate biosensor data to third party, such as a pharmacy or physician's office.

Embodiment—Remote Device with Biosensor Interface

Figure 1:
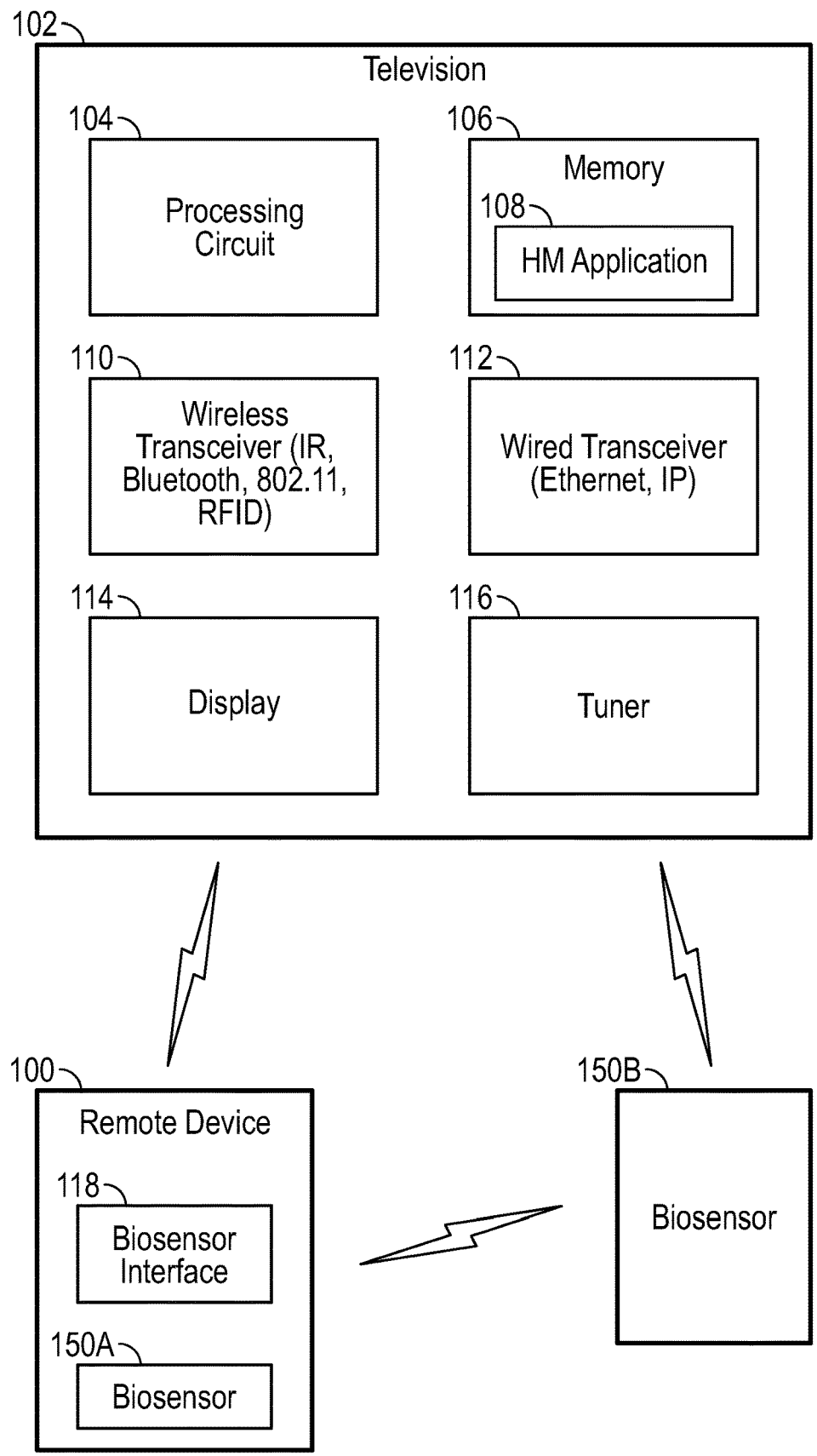
FIG. 1 illustrates an exemplary embodiment of a remote device for health monitoring.

FIG. 1 illustrates an exemplary embodiment of a remote device 100 for health monitoring. The remote device 100 includes a biosensor interface 118 that is configured to collect biosensor data from an integrated biosensor and/or by receiving biosensor data from one or more external biosensors 150 or other types of sensors either through a wireless connection or a wired connection. In an embodiment, the remote device 100 is a television remote control and communicates with a television 102 to control channel changing and other operations of the television 102. For example, the remote device 100 may have a primary purpose of controlling the television or only have capabilities of controlling and communicating with the television 102 and biosensors 150. In other embodiments, the remote device 100 includes a user device, such as a smart phone, laptop, desktop, smart tablet, smart watch, or other electronic device.

In an embodiment, the television 102 includes a processing circuit 104, a memory 106, a wireless transceiver 110, a wired transceiver 112, a display 114 and a tuner 116. The wireless transceiver 110 includes an infrared (IR) wireless transceiver that is configured to communicate with the remote device 100. The wireless transceiver 110 also includes Bluetooth (such as a Bluetooth Low Energy Transmitter (BLE 4.2) and/or 802.11 WLAN or other wireless protocol transceiver that is configured to communicate with a user device or third party service provider network. For example, the wireless transceiver 110 may operate in a Bluetooth protocol (such as a Bluetooth Low Energy Transmitter (BLE 4.2) or may utilize a standard protocol in the 900 MHz range, such as IEEE 802.11ah, Zigbee, IEEE 802.15-11 etc. or operate in the 900 MHz range over a serial link using a proprietary protocol. In other embodiments, the wireless transceiver 110 operates in one or more other wireless frequency bands or protocols, such as near field communication, short range radio frequency, RFID, or other short range wireless communication protocol. The television 102 may also include a wired transceiver 112, such as an Ethernet or IP wired connection, that is configured to communicate with a user device or third party service provider network.

In one aspect, the television 102 includes a Health Monitoring (HM) application 108 stored in the memory 106. The processing circuit 104 is configured to process one or more instructions of the HM application 108 to perform one or more of the functions described herein. The HM application 108 processes biosensor data from the remote device 100 and displays the biosensor data on the display 114. The HM application 108 may also control or generate transmissions including biosensor data to third parties. For example, the HM application 108 may generate messages that include requests to refill medications that are transmitted to a pharmacy over a wide area network (WAN) using the wireless transceiver 110 or wired transceiver 112. In another example, the HM application 108 may generate messages that include patient health data or other patient information that are transmitted to a doctor's hospital over a wide area network (WAN) using the wireless transceiver 110 or wired transceiver 112, etc.

Figure 2:
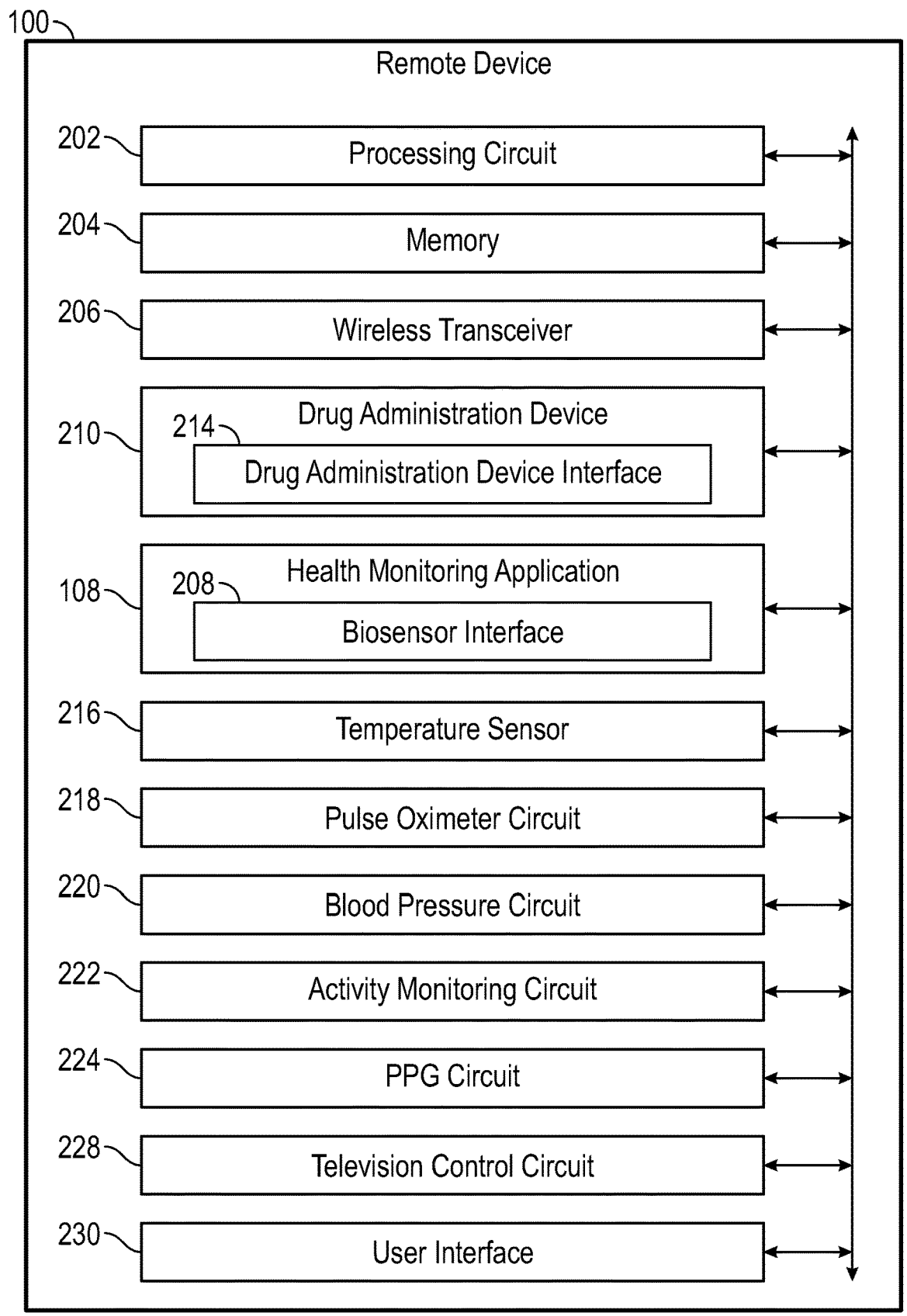
FIG. 2 illustrates a schematic block diagram of an exemplary embodiment of the remote device.

FIG. 2 illustrates a schematic block diagram of an exemplary embodiment of the remote device 100. The remote device 100 includes a processing circuit 202, a memory 204 and a wireless transceiver 206. The wireless transceiver 206 includes an infrared (IR) wireless transceiver that is configured to communicate with the television 102. The wireless transceiver 206 may also include a Bluetooth and/or 802.11 WLAN or other wireless protocol transceiver that is configured to communicate with an external biosensor or a user device, such as a smart phone, laptop, desktop, smart tablet, smart watch, or other electronic device, etc. For example, the wireless transceiver 206 may operate in a Bluetooth protocol (such as a Bluetooth Low Energy Transmitter (BLE 4.2) or may utilize a standard protocol in the 900 MHz range, such as IEEE 802.11ah, Zigbee, IEEE 802.15-11 etc. or operate in the 900 MHz range over a serial link using a proprietary protocol. In other embodiments, the wireless transceiver 206 operates in one or more other wireless frequency bands or protocols, such as near field communication, short range radio frequency, RFID, or other short range wireless communication protocol.

In an embodiment, the remote device 100 is configured to collect biosensor data, e.g. either by receiving biosensor data from one or more external biosensors 150 or from integrated biosensors. For example, the remote device 100 may include one or more integrated biosensors, such as a temperature sensor 216 (contact or non-contact), a pulse oximeter circuit 218, a blood pressure circuit 220, an activity monitoring circuit 222, etc. In addition, the remote device 100 may communicate with external biosensors 150 using the wireless transceiver 206 to receive biosensor data, as described in more detail herein below.

The remote device 100 may also include an integrated Drug Administration Device and/or a Drug Administration Device Interface 210 that is configured to deliver medication to a patient in response to the biosensor data. For example, the Drug Administration Device may include an external or integrated skin patch, IV drug pump, etc.

The remote device 100 also includes a health monitoring (HM) application 108 that may be stored in the memory 204. The health monitoring (HM) application 108 processes the biosensor data, such as measurements made by the biosensors, and generates health monitoring data. For example, the HM application may instruct the processing circuit 202 to execute logic to direct the television 102 to present one or more graphical user interfaces (GUI). The GUIs present the health monitoring data generated by the remote device 100 as well as user commands to control the biosensors. The remote device 100 may also communicate with a user device that includes the HM application to also generate one or more GUIs on the user device.

For example, the non-contact temperature sensor 216 may include a thermopile IR temperature sensor. In use, a user swipes the remote device 100 over their forehead or other area of the body without touching the skin. The temperature sensor 216 in the remote device 100 detects the temperature and transmits the temperature to the HM application 108 for storage and tracking. The HM application 108 may instruct the television to display a graphical user interface (GUI) illustrating a current temperature and a history of temperature readings for one or more users.

In another example, the blood pressure sensor 216 detects blood pressure and transmits the blood pressure to the HM application 108 for storage and tracking. The HM application 108 may instruct the television 102 to display a graphical user interface (GUI) illustrating a current blood pressure and a history of blood pressure readings for one or more users.

In another example, the activity monitoring circuit 222 includes, e.g., an accelerometer, GPS, or other motion detector. In another embodiment, the remote device 100 communicates with an external activity monitoring device, such as a FitBit® wireless wristband or other external activity tracker. The HM application 108 may collect activity information, such as periods of rest, periods of activity, steps walked or run, etc. The HM application 108 may then instruct the television 102 to display a graphical user interface (GUI) illustrating the activity information for one or more users.

In another aspect, the remote device 100 includes an integrated pulse oximeter circuit 218. The pulse oximeter 218 detects pulse or heart rate and blood oxygen saturation levels (SpO₂) and transmits the biosensor data to the HM application 108 for storage and tracking. The HM application 108 may instruct the television 102 to display a graphical user interface (GUI) illustrating a current pulse and blood oxygen level and a history of heart rate and blood oxygen levels for one or more users.

In an embodiment, the remote device 100 may include a photoplethysmography (PPG) circuit 224. The PPG circuit is configured to generate at least a first spectral response for light reflected around a first wavelength from skin tissue of the patient, generate at least a second spectral response for light detected around a second wavelength reflected from the skin tissue of the patient. The processing circuit 202 is configured to process the first and second spectral responses at the first wavelength and the second wavelength and determine biosensor data using the first and second spectral responses. For example, the biosensor data may include oxygen saturation levels and pulse rate. The PPG circuit 224 may thus be included as the pulse oximeter circuit 218 or in addition to a separate pulse oximeter circuit 218. In addition, the PPG circuit 224 may also obtain concentration levels of one or more substances in arterial blood flow using first and second spectral responses at predetermined wavelengths, such as an indicator of glucose levels, analyte levels, blood alcohol levels, etc. The operation of the PPG circuit 224 is described in more detail herein.

The remote device also includes a television control circuit 228. The television control circuit 228 receives user input and controls functions of the television 102 in response to the user input. For example, the television control circuit 228 may generate commands to change channels, record, or operate the HM application 108 in response to the user input. The commands are then transmitted to the television 102 by the wireless transceiver 206.

In an embodiment, the remote device 100 may include one or more user interfaces 230. For example, the one or more user interfaces may include touchless controls. The touchless controls are configured to detect movement of a user and a channel indicated by the movement without a user touching the remote device 100. In another aspect, the remote device 100 is configured to change a channel by detecting a tilt or motion of the remote device 100.

The user interface 230 may include a touch pad, touch screen, LED wireless mouse, keypad or other type of user interface. For example, the remote device 100 may include a mouse and use an IR or visible light to move a pointer or other icon on the television display to select commands to control the television 102 and/or HM application 108. The user interface 230 may include a touch pad to select commands on the television display that control operation of the television 102 and/or and HM application 108. In another embodiment, the remote device 100 includes a touch screen that displays graphical user interfaces having selections and commands for controlling the television 102 or HM application 108.

Embodiment—Drug Administrative Device

Figure 3:
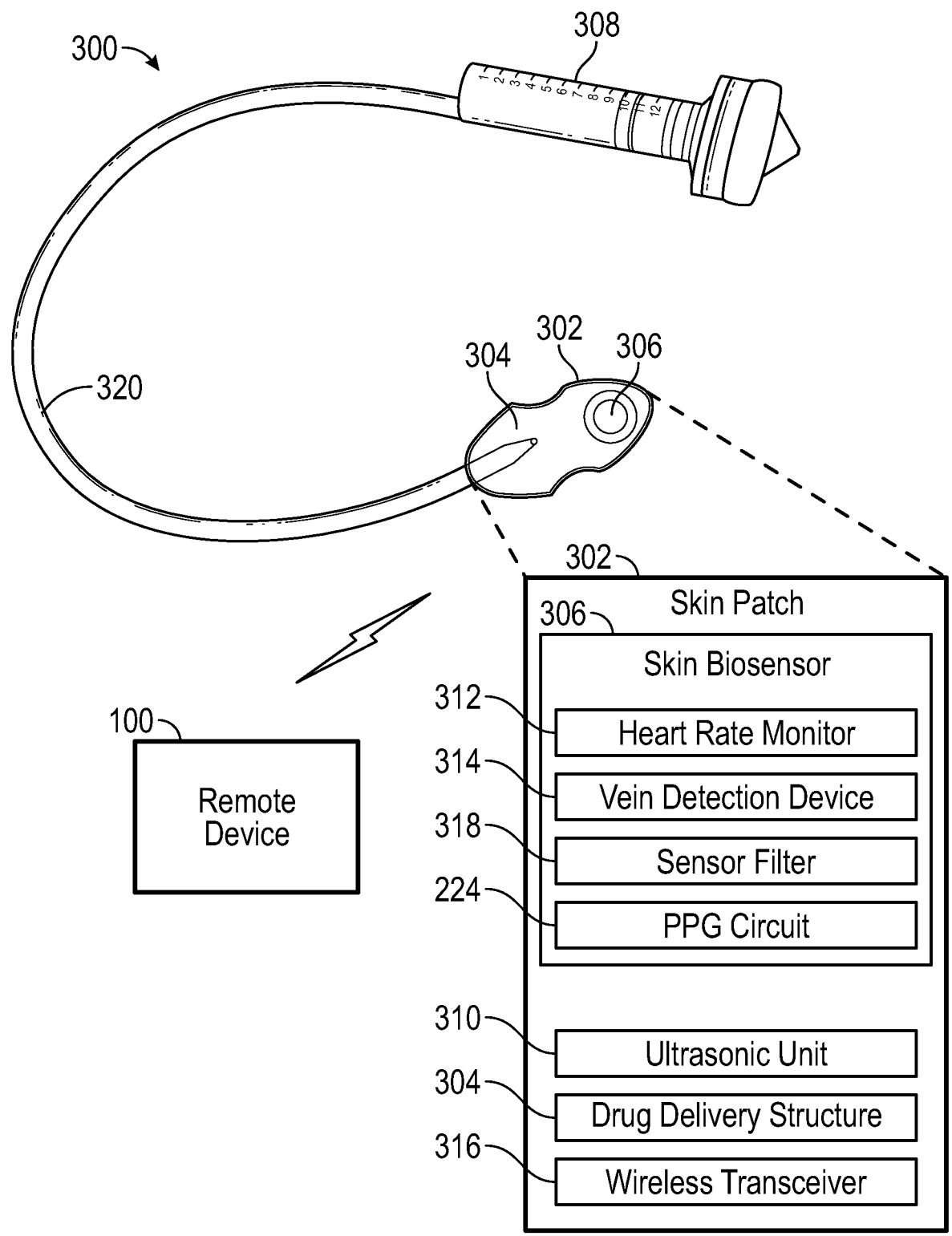
FIG. 3 illustrates an exemplary embodiment of a drug administrative device.

FIG. 3 illustrates an exemplary embodiment of a drug administrative device 300.

The drug administrative device 300 includes a skin patch 302 and drug pump 308. The skin patch 302 includes a wired or wireless transceiver 316 configured to communicate with the remote device 100. For example, the wireless transceiver 316 may include an infrared (IR) wireless transceiver 316 that is configured to communicate with the remote device 100. The wireless transceiver 316 may alternatively or additionally include a Bluetooth and/or 802.11 WLAN or other wireless protocol transceiver that is configured to communicate with the remote device 100 or other user device. For example, the wireless transceiver 316 may operate in a Bluetooth protocol (such as a Bluetooth Low Energy Transmitter (BLE 4.2) or may utilize a standard protocol in the 900 MHz range, such as IEEE 802.11ah, Zigbee, IEEE 802.15-11 etc. or operate in the 900 MHz range over a serial link using a proprietary protocol. In other embodiments, the wireless transceiver 316 operates in one or more other wireless frequency bands or protocols, such as near field communication, short range radio frequency, RFID, or other short range wireless communication protocol. In another aspect, the wireless transceiver 316 may include a wired transceiver to communicate with the remote device 100. Though the wireless transceiver 316 is illustrated as integrated within the skin patch 302, it may be included in one or more other parts of the drug administrative device 300. A battery, such as a hydrogen fuel cell, may be integrated to power the wireless transceiver 316 and other components of the drug administrative device 300.

The skin patch 302 may also include a skin biosensor 306. The skin biosensor 306 includes one or more biosensors, e.g., a heart rate monitor 312 and a vein detection device 314 and a PPG circuit 224. The heart rate monitor is configured to detect a heart rate of a patient during drug delivery. In another aspect, the heart rate monitor 312 in the skin biosensor 306 is configured to monitor blood flow. For example, the skin patch 302 monitors and transmits heart rate measurements from one or more extremities, such as the arms and legs of the user, as well as from a chest/heart area of the user. The user may move the skin patch 302 to the plurality of positions or multiple skin patches may be positioned on the plurality of positions. The heart rate readings from the heart/chest area and from the one or more extremities of the user are monitored and tracked by the HM application 108 of the remote device 100. The heart rate readings are used to determine and track blood flow between the heart and the one or more extremities. Based on the heart rate readings, the HM application 108 may determine potential blockages in blood flow.

The skin biosensor 306 may also include a vein detection device 314 that assists a user, such as a patient or care giver, to locate veins or arteries. The vein detection device 314 is configured to scan a designated area of skin using an infrared (IR) signal to locate a high IR signature that indicates the presence of a vein or an artery. Ultraviolet (UV) signal may be used as well to detect the location of vein or artery. The vein detection device 314 may include a sensor filter 318 that filters out ambient light and light not reflected from the skin but passes IR light reflected from the designated area of the skin.

The PPG circuit is configured to obtain at least a first spectral response for light reflected around a first wavelength from skin tissue of the patient, obtain at least a second spectral response for light detected around a second wavelength reflected from the skin tissue of the patient. A processing circuit (not shown) within the skin patch 302 or PPG circuit 224 is configured to process the first and second spectral responses at the first wavelength and the second wavelength and determine patient vitals using the first and second spectral responses. For example, the PPG sensor may be configured to detect oxygen saturation (SPO₂) levels in blood flow, as well as heart rate and blood pressure.

The PPG circuit 224 may thus be included as the heart rate monitor 312 or in addition to a separate heart rate monitor 312. In addition, the PPG circuit 224 may also obtain concentration levels of one or more additional substances in arterial blood flow using first and second spectral responses at predetermined wavelengths, such as an indicator of glucose levels, analyte levels, blood alcohol levels, etc. The operation of the PPG circuit 224 is described in more detail herein.

The skin biosensor 306 may include additional or alternative biosensors, such as a temperature sensor 216, activity monitoring circuit 222, etc.

In an embodiment, the skin patch 302 is configured to administer the medication to the user through the drug delivery structure 304. The drug delivery structure may include permeable material or an array of microneedles. The drug delivery structure 304 may also include a drug fluid bowl that holds a predetermined dosage of the medication.

The skin patch 302 may also include an ultrasonic unit 310 that includes an ultrasonic transducer and one or more ultrasonic horns (also known as acoustic horn, sonotrode, acoustic waveguide, ultrasonic probe) embedded in the skin patch. The ultrasonic horn is a tapering metal bar commonly used for augmenting the oscillation displacement amplitude provided by the ultrasonic transducer. The skin patch 302 then initiates transdermal application of medication through a permeable material or microneedles while ultra-sonically transmitting energy into the epidermal layer of the skin using the ultrasonic unit 310. This process excites pours on the sub-cutaneous layer of the skin to allow rapid absorption of the medication.

The drug delivery structure 304 may be coupled to a syringe 308 by IV tubing 320. For example, the syringe 308 may be preloaded with the medication for administration by the skin patch 302. The remote device 102 is then configured to control the syringe to secrete a predetermined dosage of medication at a predetermined rate of administration. The remote device 102 may also control the predetermined dosage of medication, the predetermined rate of administration and period of time between dosages based on the biosensor data from one or more biosensors. For example, the remote device 102 receives real time, continuous feedback of biosensor data from one or more biosensors during periods of administration of the medication. If the remote device 102 detects an allergic reaction or unsafe heart rate, the remote device 102 may control the syringe 308 and/or skin patch 302 to halt secretion of the medication.

In another embodiment, the remote device 102 may be implemented to control a Smart Injectable Pen, a Continuous Glucose Monitoring Device and Insulin Pump, or other drug administering device. For example, the remote device 102 may control an IV infusion pump using biosensor data received from one or more biosensors 150, such as the skin biosensor 306.

Embodiment—Hydrogen Fuel Cell Syringe

Figure 4:
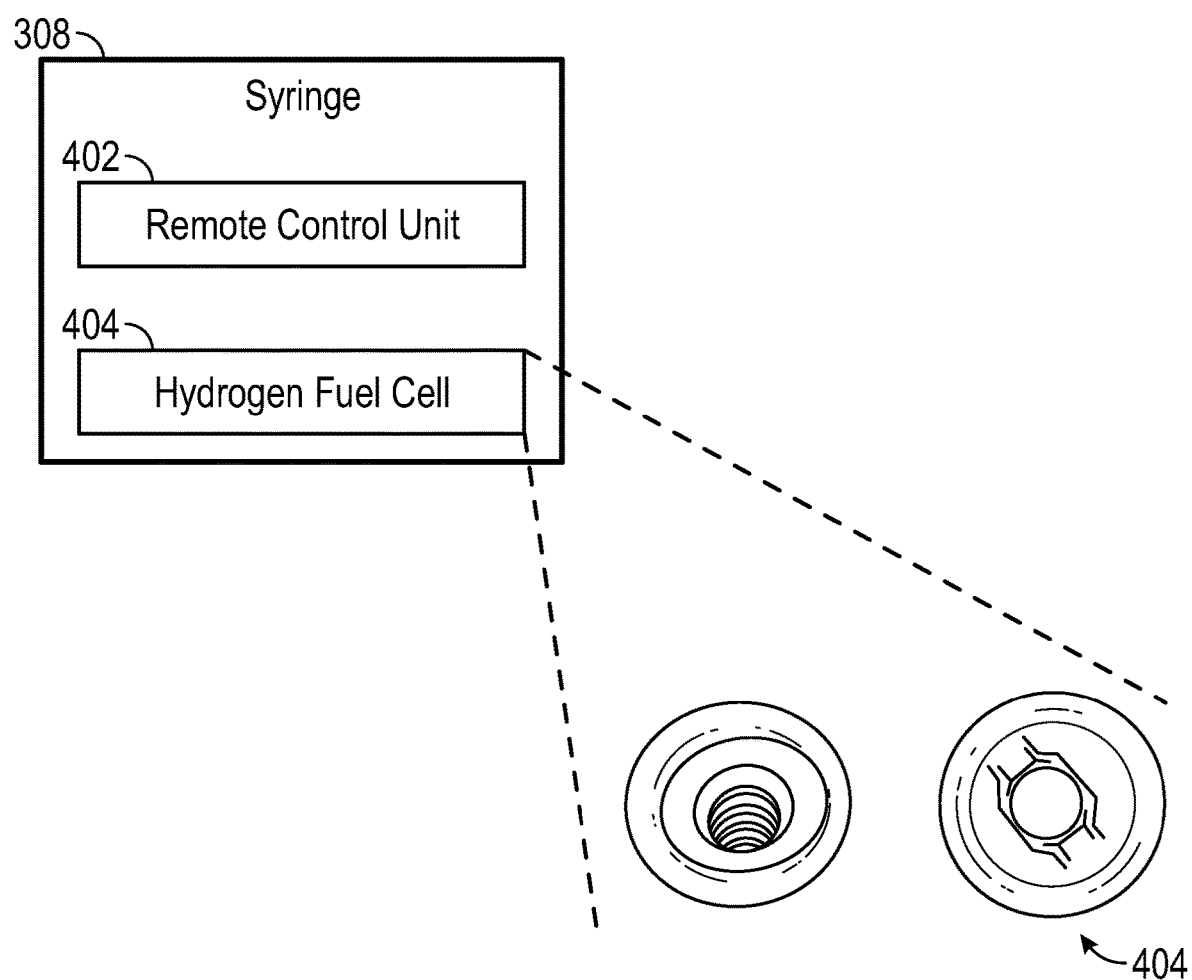
FIG. 4 illustrates a schematic block diagram of an embodiment of a syringe powered by a hydrogen fuel cell.

FIG. 4 illustrates an embodiment of the syringe 308. The syringe 308 may be powered by a battery, such as a hydrogen fuel cell 404. The hydrogen fuel cell 404 powers the syringe 308 to push the pre-loaded medications in the syringe 308 to the skin patch 302. The syringe 308 may include a remote control unit 402 including a processing circuit that controls the syringe 308 to dispense a predetermined dosage of medication at a predetermined rate of administration. In another embodiment, the remote control unit 402 may be configured to provide for direct injection of medication into an IV tube or catheter or a smart pen or custom IV syringe. The remote device 102 communicates with the remote control unit 402 to control the dosage and administration rate of the medication using continuous and real time feedback of biosensor data, such as heart rate.

Embodiment—Wearable Shirt Button with Biosensor

Figure 5:
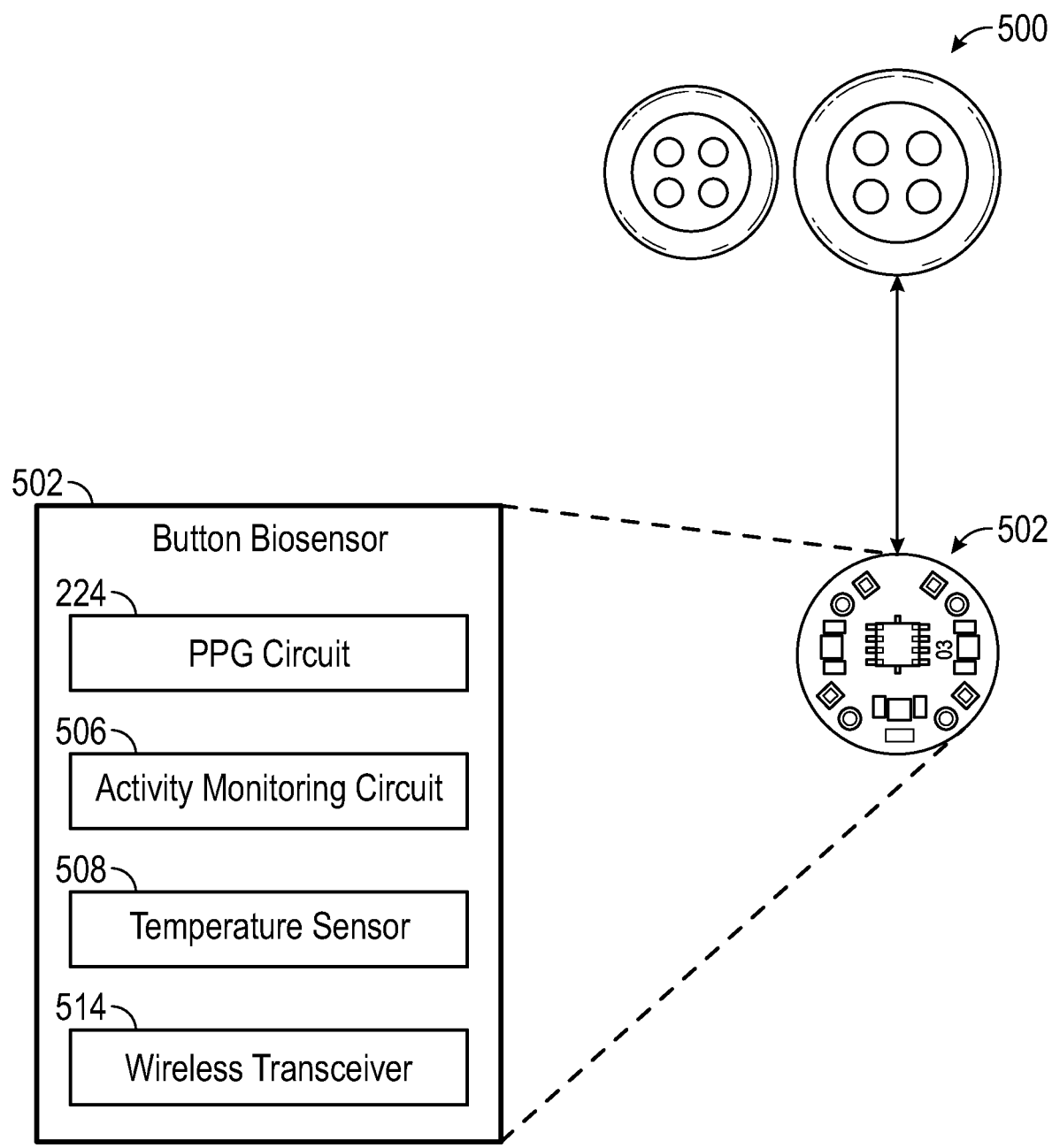
FIG. 5 illustrates an embodiment of a schematic block diagram of a wearable shirt button with an integrated button biosensor.

FIG. 5 illustrates an embodiment of a wearable shirt button 500 with an integrated button biosensor 502. The button biosensor 502 includes for example an integrated Heart Rate Monitor 504, Pulse Oximeter 506, Glucose Sensor 508, and Blood Analyte Sensor 510 and Blood Alcohol Sensor 512. The button biosensor 502, e.g., is configured to integrate into a shirt button or clothing for measuring health information. The wireless transceiver 514 includes an IR wireless transceiver (positioned on an opposite side of the body facing sensor side) for transmitting IR codes to a television 102 or remote device 102. The wireless transceiver 514 may also include Bluetooth and/or 802.11 WLAN or other wireless protocol transceiver that is configured to communicate with the user device such as a smart phone, laptop, desktop, smart tablet, smart watch, or other electronic device, etc. For example, the wireless transceiver 206 may operate in a Bluetooth protocol (such as a Bluetooth Low Energy Transmitter (BLE 4.2) or may utilize a standard protocol in the 900 MHz range, such as IEEE 802.11ah, Zigbee, IEEE 802.15-11 etc. or operate in the 900 MHz range over a serial link using a proprietary protocol. In other embodiments, the wireless transceiver 514 operates in one or more other wireless frequency bands or protocols, such as near field communication, short range radio frequency, RFID, or other short range wireless communication protocol.

In use, in an embodiment, the button sensor 502 detects biosensor data and transmits the biosensor data to an HM application in the remote device 100 or a user device or the television 102 for storage and tracking. The HM application may instruct the remote device 100 or television 102 or user device to display a graphical user interface (GUI) illustrating the biosensor data and a history of the biosensor data for one or more users.

Figure 6:
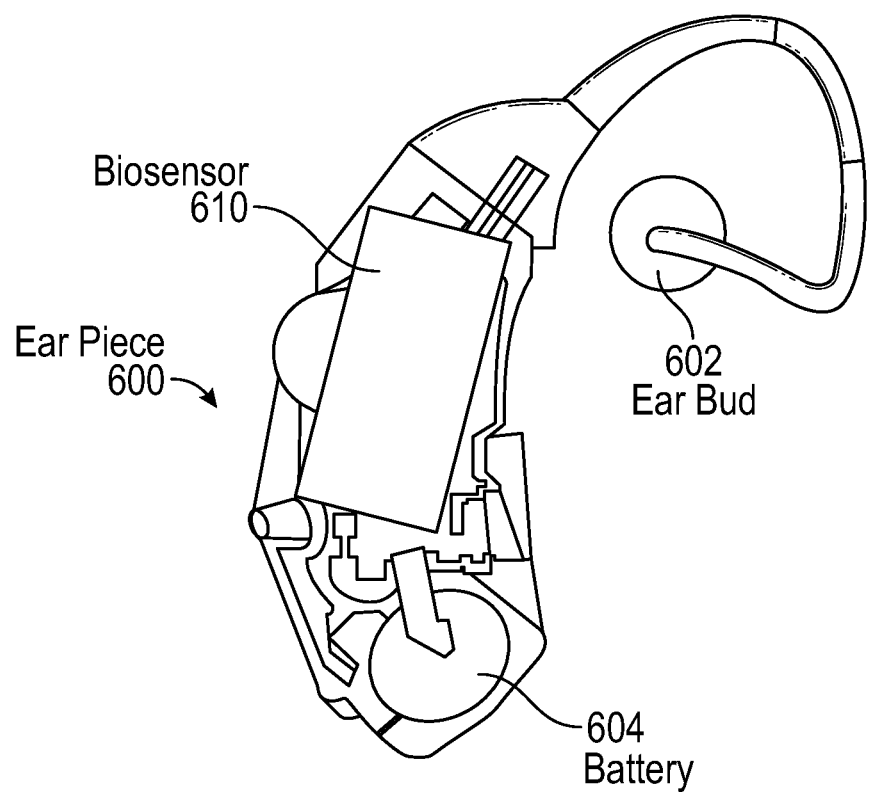
FIG. 6 illustrates illustrates an exemplary embodiment of another form factor of a biosensor.

FIG. 6 illustrates an exemplary embodiment of another form factor of a biosensor 610. In this embodiment, the biosensor 610 is configured in an earpiece 600. The earpiece 600 includes an earbud 602. The biosensor 610 is configured to transmit light into the ear canal from one or more optical fibers in the ear bud 602 and detect light from the ear canal using one or more optical fibers. The biosensor 150 may be powered by a battery 604. The biosensor 610 includes a wireless transceiver to transmit biosensor data to the remote device 100.

Due to its compact form factor, the biosensor may be configured in various form factors, such as a skin patch, ear piece, on a button, etc. The biosensor may be configured for measurement of biosensor data on various skin surfaces of a patient, including on a forehead, arm, wrist, abdominal area, chest, leg, ear lobe, finger, toe, ear canal, etc.

Embodiment—Biosensor Components

Figure 7:
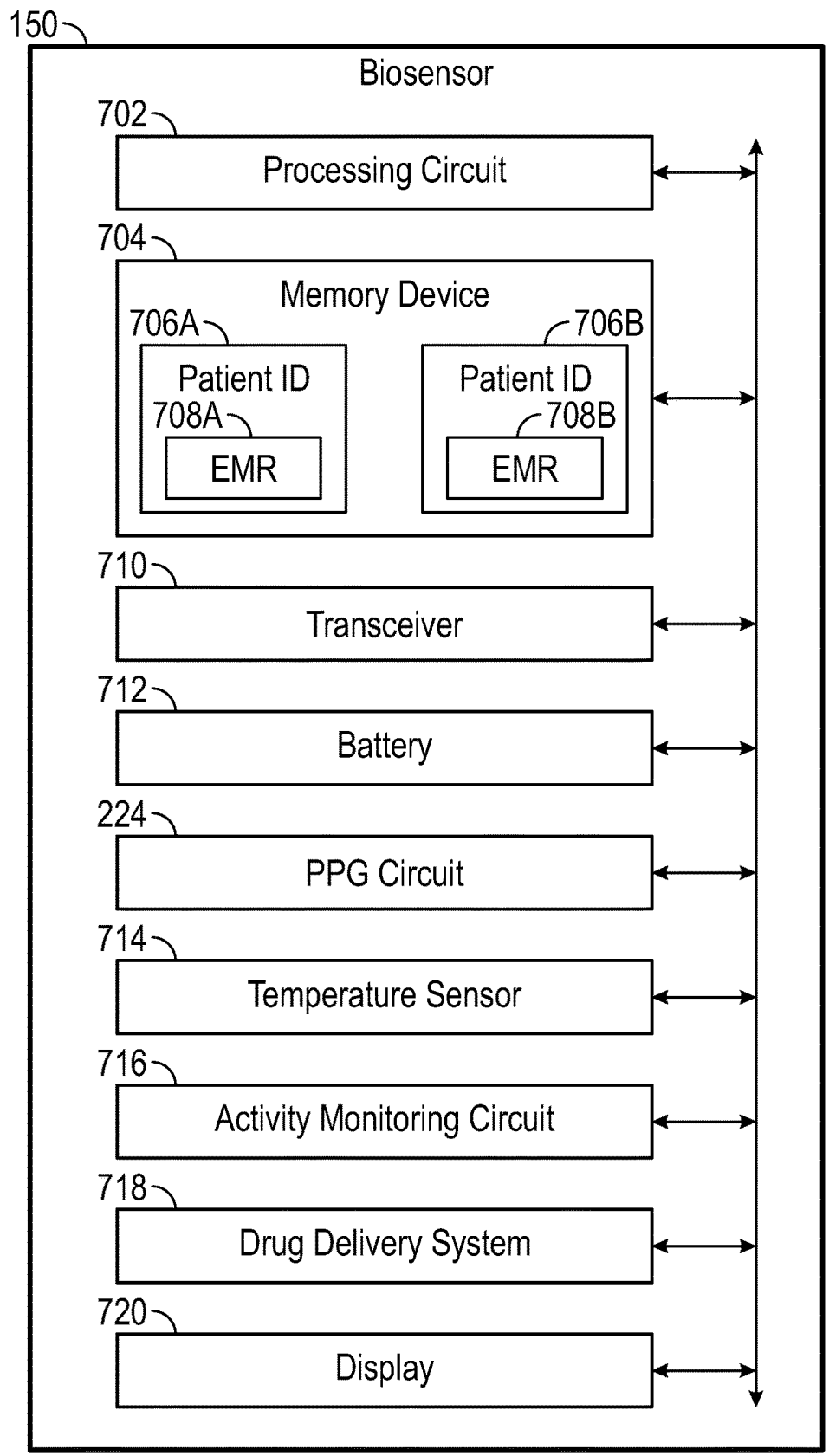
FIG. 7 illustrates a schematic block diagram of an exemplary embodiment of a biosensor.

FIG. 7 illustrates a schematic block diagram of an exemplary embodiment of a biosensor 150. The biosensor 150 includes one or more processing circuits 702 communicatively coupled to a memory device 704. In one aspect, the memory device 104 may include one or more non-transitory processor readable memories that store instructions which when executed by the processing circuit 702, causes the processing circuit 702 to perform one or more functions described herein. The memory device 704 may also include an EEPROM to store one or more patient identifications (ID) 706*a*, 706*b*, wherein each of the patient IDs 706 are associated with a patient being monitored by the biosensor 150. The memory device 704 may also store an electronic medical record (EMR) 708*a*, 708*b* or portion of an EMR 708*a*, 708*b* associated with each of the patient IDs 706. The biosensor may thus be used to monitor multiple users or patients associated with different patient IDs 706. The biosensor data obtained by the biosensor 150 may be stored in the EMR 708 associated with the monitored patient ID 706. The processing circuit 702 may be co-located with one or more of the other circuits in the biosensor 150 in a same physical encasement or located separately in a different physical encasement or located remotely. In an embodiment, the biosensor 150 is battery operated and includes a battery 712, such as a lithium ion battery. The biosensor 150 may also include a display 720 configured to display the biosensor data.

The biosensor 150 further includes a transceiver 710. The transceiver 710 may include a wireless or wired transceiver configured to communicate with one or more devices over a LAN, MAN and/or WAN. In one aspect, the wireless transceiver 710 may include IEEE 802.11ah, Zigbee, IEEE 802.15-11 or WLAN (such as an IEEE 802.11 standard protocol) compliant transceiver. In another aspect, the wireless transceiver 710 may also include or alternatively include an interface for communicating over a cellular network. In an embodiment, the wireless transceiver 710 may include a thin foil for an antenna that is specially cut and includes a carbon pad contact to a main PCB of the biosensor 150. This type of antenna is inexpensive to manufacture and may be printed on the inside of an enclosure for the biosensor 150 situated away from the skin of the patient to minimize absorption. The transceiver 710 may also include a wired transceiver interface, e.g., a USB port or other type of wired connection, for communication with one or more other devices over a LAN, MAN and/or WAN.

The biosensor 150 includes one or more types of sensors, such as a PPG circuit 224, a temperature sensor 714 or an activity monitoring circuit 716. The temperature sensor 714 is configured to detect a temperature of a patient. For example, the temperature sensor 714 may include an array of sensors (e.g., 16x16 pixels) positioned on a side of the biosensor 150 such that the array of sensors are adjacent to the skin of the patient. The array of sensors then detects an indication of the temperature of the patient from the skin.

The activity monitoring circuit 716 is configured to monitor the activity level of the patient. For example, the activity monitoring circuit 716 may include a multiple axes accelerometer that measures a position of the patient and motion of the patient. In one aspect, the activity monitoring circuit 716 determines periods of activity and rest. For example, the activity monitoring circuit 716 monitors and records periods of rest that meet a predetermined threshold of low motion or activity level, such as sitting, lying, sleeping, etc. The activity monitoring circuit 716 may also monitor and record periods of activity that meet a predetermined threshold of motion or activity level, such as walking, running, lifting, squatting, etc. The biosensor 150 is then configured to measure and store the patient vitals with an indicator of the activity level of the patient. For example, blood oxygen levels may vary greatly in patients with COPD during rest and activity. The vitals of the patient are tracked during periods of activity and rest and the level of activity at time of measuring the vitals is recorded. The biosensor 150 is thus configured to associate measurements of patient vitals with the activity level of the patient.

In another aspect, to help lower power consumption, in an embodiment, the biosensor 150 includes a rest mode. For example, the activity monitoring circuit 716 may signal a rest mode when a patient is asleep or meets a predetermined threshold of low activity level for a predetermined time period. In the rest mode, the biosensor 150 signals one or more modules to halt non-essential processing functions. When the activity monitoring circuit 716 detects a higher activity level exceeding another predetermined threshold for a predetermined time period, the the biosensor 150 signals one or more modules to exit rest mode and resume normal functions. This activity monitoring feature helps to save power and extend battery life of the biosensor 150.

In another aspect, the activity monitoring circuit 716 is configured to include a fitness tracker application. The activity monitoring circuit 716 may monitor a number of steps of the patient, amount and length of periods of sleep, amount and length of periods of rest, amount and length of periods of activity, etc.

The biosensor 150 may also include an integrated drug delivery system 718 or be communicatively coupled to a drug delivery system 116. The biosensor 150 may be configured to control delivery of medicine to a patient based on biosensor data obtained by the biosensor 150 as described in more detail in U.S. patent application Ser. No. 15/276,760 entitled, "SYSTEM AND METHOD FOR A DRUG DELIVERY AND BIOSENSOR PATCH," filed Sep. 26, 2016 and hereby expressly incorporated by reference herein.

The biosensor 150 may include a display 720. The biosensor 150 is configured to display a graphical user interface (GUI) that includes biosensor data.

The biosensor 150 also includes a transceiver 710 that may operate using RFID, short range radio frequency, Bluetooth, infrared link, or other short range wireless communication protocol. The near field transceiver 710 may transmit the patient identification and biosensor data over a short range to the remote device 100.

The biosensor 150 also includes a PPG circuit 224. The PPG circuit 224 may be configured to detect oxygen saturation ($SaO_2$ or $SpO_2$) levels in blood flow, as well as heart rate and blood pressure. In addition, the PPG circuit 224 is configured to detect concentration levels or indicators of one or more substances in the blood flow of the patient as described in more detail herein.

Figure 8A:
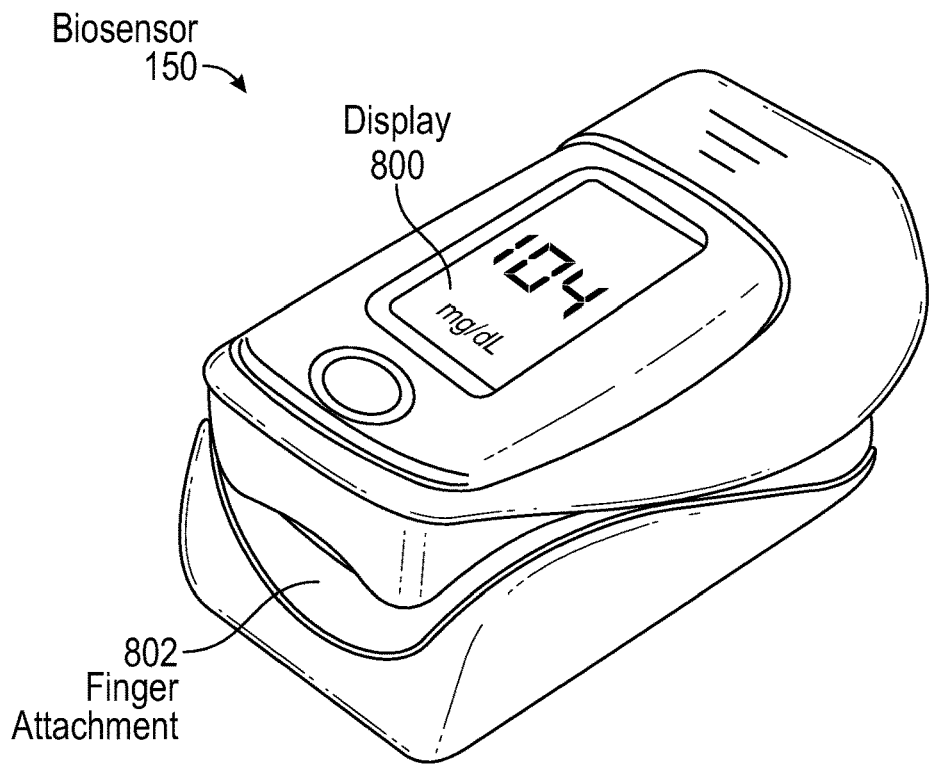
FIG. 8A illustrates an exemplary embodiment of another form factor of the biosensor.

FIG. 8A illustrates an exemplary embodiment of another form factor of the biosensor 150. In this embodiment, the biosensor 150 is configured to attach to a finger or fingertip using finger attachment 802. The finger attachment 802 is configured to securely hold a finger that is inserted into the finger attachment 802. A display 800 is implemented on the biosensor 150 with a graphical user interface (GUI) that displays biosensor data. For example, in use, the biosensor 150 measures blood glucose levels using the PPG circuit 224. The blood glucose levels are then displayed using the GUI on the display 800. The PPG circuit may also measure other patient vitals that are displayed on the display 800, such as oxygen saturation levels, temperature, respiration rates, heart rate, blood alcohol levels, digestive response, caloric intake, white blood cell count, electrolyte or other blood analyte concentrations, liver enzymes, etc. The biosensor 150 may thus provide biosensor data continuously and non-invasively.

Figure 8B:
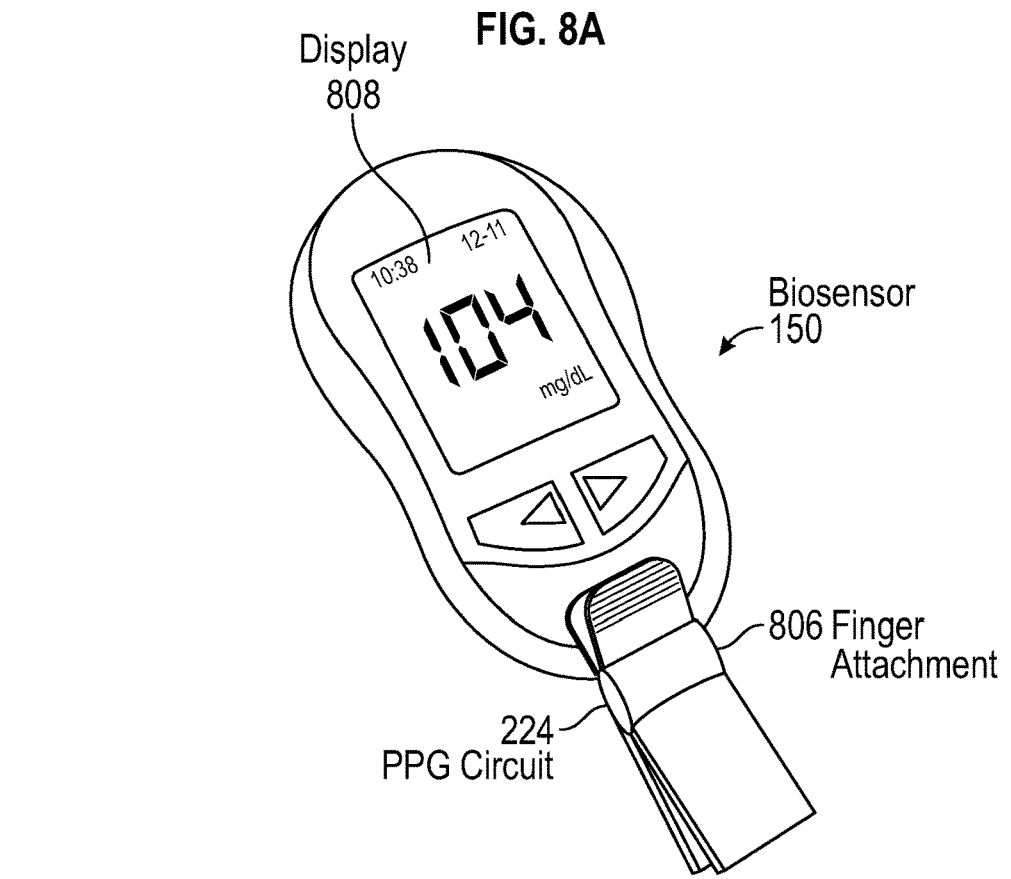
FIG. 8B illustrates an exemplary embodiment of another form factor of the biosensor.

FIG. 8B illustrates an exemplary embodiment of another form factor of the biosensor 150. In this embodiment, the biosensor 150 is configured to attach to a finger or fingertip using finger attachment 806. The finger attachment 806 includes the PPG circuit 224 and is configured to securely hold a finger that is inserted into the finger attachment 806. The finger attachment 806 may be implemented within the same encasement as the other components of the biosensor 150 or be communicatively coupled either through a wired or wireless interface to the other components of the biosensor 150. A display 808 is implemented for the biosensor 150 with a graphical user interface (GUI) that displays biosensor data including blood glucose levels.

The biosensor 150 may be configured to be implemented within the remote device 100. In addition, one or more biosensors 150 in one or more form factors may be used in combination with the remote device 100 to determine biosensor data at one or more areas of the body. The remote device 100 may then store biosensor data measured by the one or more biosensors 150 in the EMR 708 of the patient that may be used with the HM application 108.

Embodiment—HM Application

Figure 9:
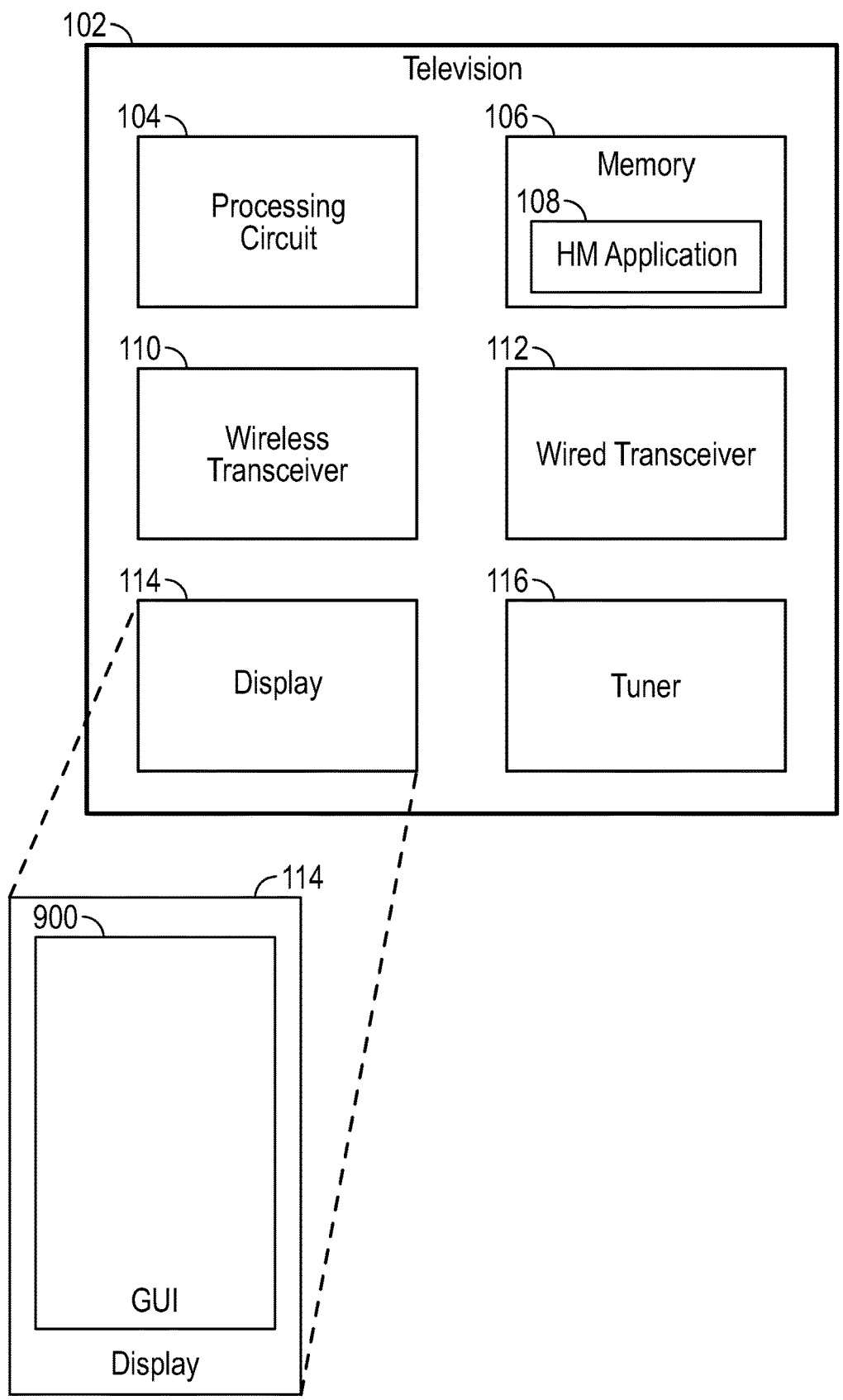
FIG. 9 illustrates an embodiment of a graphical user interface (GUI) displayed on the television.

FIG. 9 illustrates an embodiment of a graphical user interface (GUI) 900 displayed on the television 102. The remote device 100 communicates biosensor data to the television 102 that includes an HM application 108. Using the health monitoring application 108, the television 102 is configured to generate the GUI 900 for display on the display 114. An authorized user is operable to track biosensor data using the health monitoring application 108 and control certain functions of a drug administrative device 210.

Figure 10:
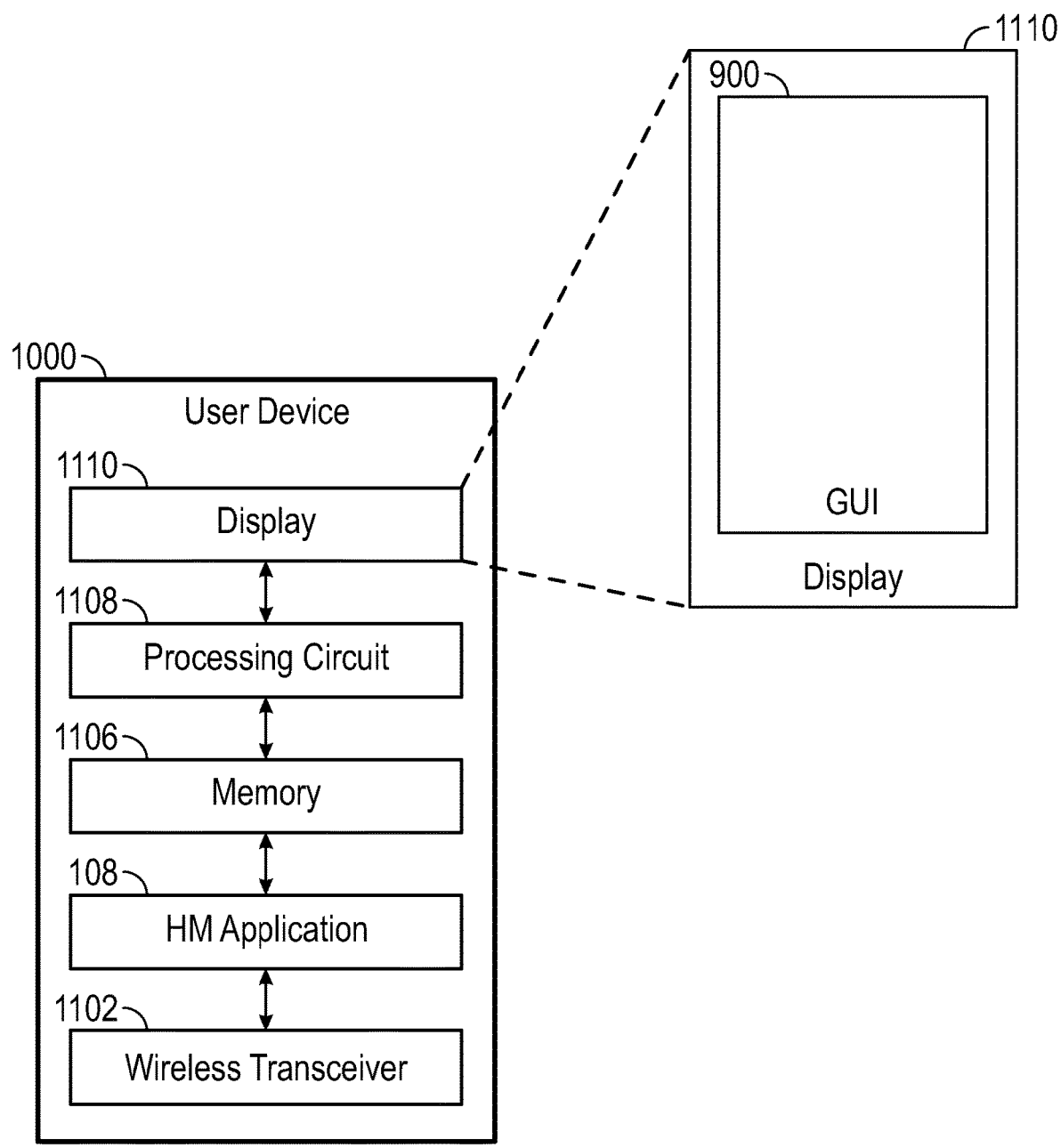
FIG. 10 illustrates an embodiment of a user device.

FIG. 10 illustrates an embodiment of a user device 1000. The user device 1000 may include a smart phone, laptop, desktop, smart tablet, smart watch, or any other electronic device. In an embodiment, the user device 1000 includes a processing circuit 1108, a display 1110 and a memory 1106. For example, the memory 1106 is a non-transitory processor readable memory that stores instructions which when executed by the processing circuit 1108, causes the processing circuit 1108 to perform one or more functions described herein. The user device 1000 includes a wireless transceiver 1102 that is configured to communicate with the remote device 100 or a communication network to a central application server or to one or more gateways.

The user device 1000 further includes a health monitoring application 108. The HM application 108 may be a web-based application supported by a central application server. For example, the central application server may be a web server and support the user application via a website. The user device 1000 may then use a web browser or other HTML enabled application to access either all or parts of the health monitoring application 108 via the website supported by the central application server. The health monitoring application 108 is then run within the the web browser. In another embodiment, the health monitoring application 108 is a stand-alone application that is downloaded to the user device 1000 and is operable on the user device 1000 without access to the web server or only needs to accesses the web server for additional information, such as biosensor data. In another embodiment, the health monitoring application 108 may be a mobile application designed for download and use by a mobile phone or other mobile device.

The health monitoring application 108 may generate a GUI 900 on the television 102 or the display 1110 of the user device 1000. The health monitoring application 108 is configured to track and display biosensor data. For example, the health monitoring application 108 receives biosensor data from remote device 100 and may then upon request to generate a GUI 900 that includes a graphical display of glucose levels or other biosensor data over a requested period of time, such as one day, one week, etc. The health monitoring application 108 may issue alerts when biosensor data reaches certain predetermined thresholds. For example, when the health monitoring application 108 determines that a glucose level measurement reaches or exceeds a predetermined high or low threshold, the health monitoring application 108 displays and sounds an alert message. In general, a good range for blood sugar levels is between 70 milligrams/deciliter (mg/Dl) and 150 mg/Dl. When the sugar level are lower than 70 mg/Dl or greater than 150 mg/Dl, the alert message may include a request or command to inject insulin by the drug administrative device 210. The health monitoring application 108 may also track activity and generate one or more GUIs 600 that includes an activity tracker display. The activity tracker display may include periods of rest or sleep and periods of activity along with biosensor data for such periods, such as pulse, glucose levels, oxygen levels, temperature, blood pressure, etc.

Figure 11:
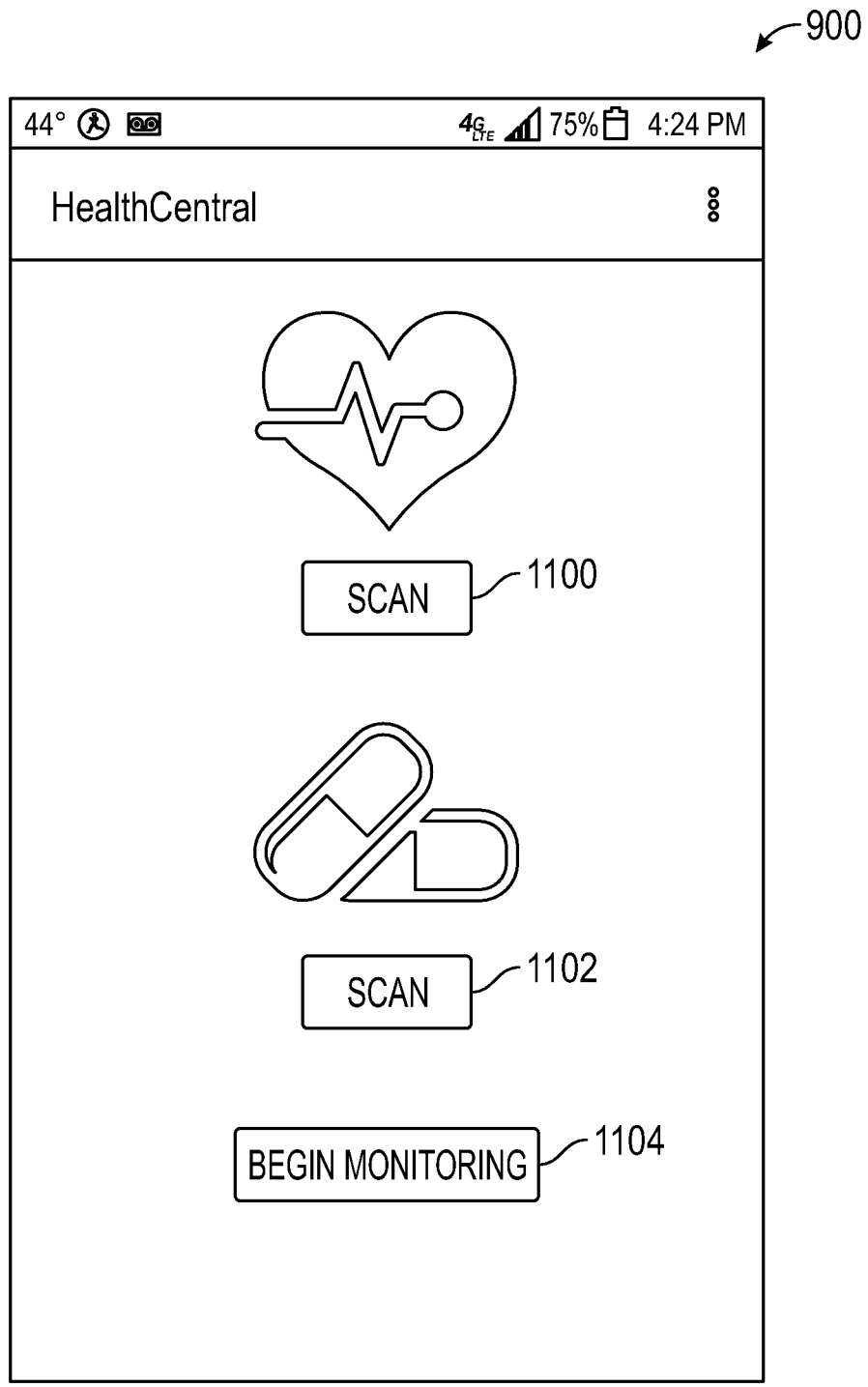
FIG. 11 illustrates a schematic block diagram of an embodiment of a graphical user interface (GUI) generated by the health monitoring application.

FIG. 11 illustrates a schematic block diagram of an embodiment of a graphical user interface (GUI) 600 generated by the health monitoring application 108. The health monitoring application 108 may generate the GUI 900, e.g. on the television 102 or the user device 1000. The GUI 900 provides an interface for a user to select a command to control operation of one or more biosensors 150. For example, a user may select to initiate a scan by a first biosensor by selecting a first scan GUI 1100 or may select to initiate a scan by a second biosensor by selecting a second scan GUI 1102. In another example, a user may select to begin monitoring by a plurality of biosensors 150 by selecting a Begin Monitoring GUI 1104.

Figure 12:
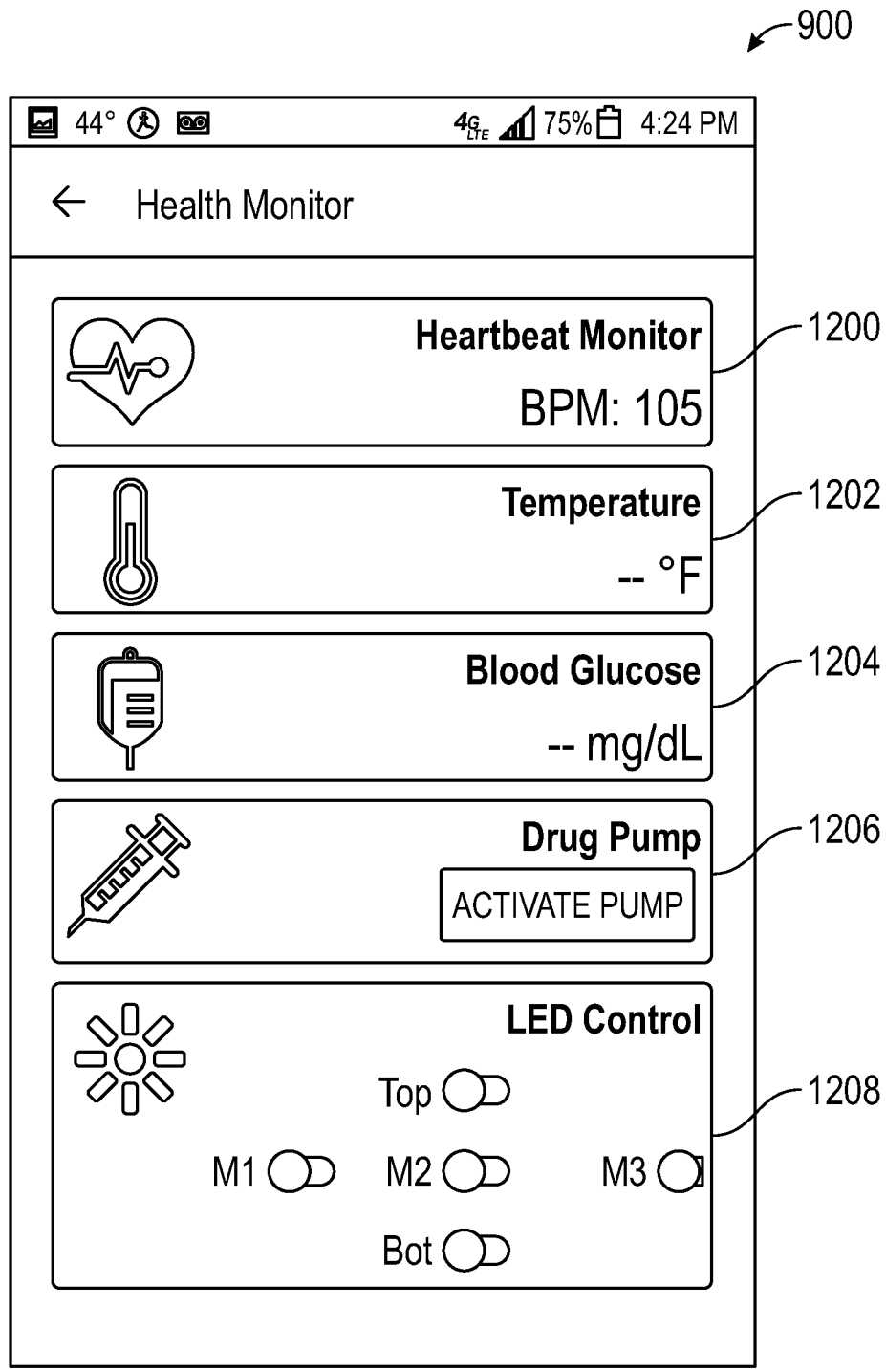
FIG. 12 illustrates a schematic block diagram of an embodiment of a graphical user interface (GUI) generated by the health monitoring application.

FIG. 12 illustrates a schematic block diagram of an embodiment of a graphical user interface (GUI) 600 generated by the health monitoring application 108. The health monitoring application 108 may be implemented in a television 102 and generate the GUI 900, e.g. on the television display 114, based on biosensor data from the remote device 100. The HM application 108 is operable to generate the GUI 900 to display monitored biosensor data. For example, the GUI 900 may display a Heartbeat Monitor GUI 1200 that tracks detected heart rate or beats per minute (BPM), e.g. BPM=105. The GUI 900 may display a Temperature GUI 1202 that illustrates measured temperature of a user, and a Blood Glucose Level GUI 1204 that illustrates measured indicator of blood glucose levels. The GUI 900 may also illustrate an Activate Pump command GUI 1206 to activate a drug administrative device 210, such as a drug pump.

The GUI 900 may also illustrate a history of readings of biosensor data. The history may display biosensor data measured over one day, multiple days, one week, one month, one year, or a specified time frame. In another embodiment, the health monitoring application 108 may be implemented in a user device 1000 and generate the GUI 900, e.g. on a user device, based on biosensor data received from the remote device 100 and/or other external biosensors 150.

The HM application 1308 may also generate an LED control GUI 1208. A user may control the operation of the LEDs of the remote control 100 using the LED control GUI 1208.

Figure 13:
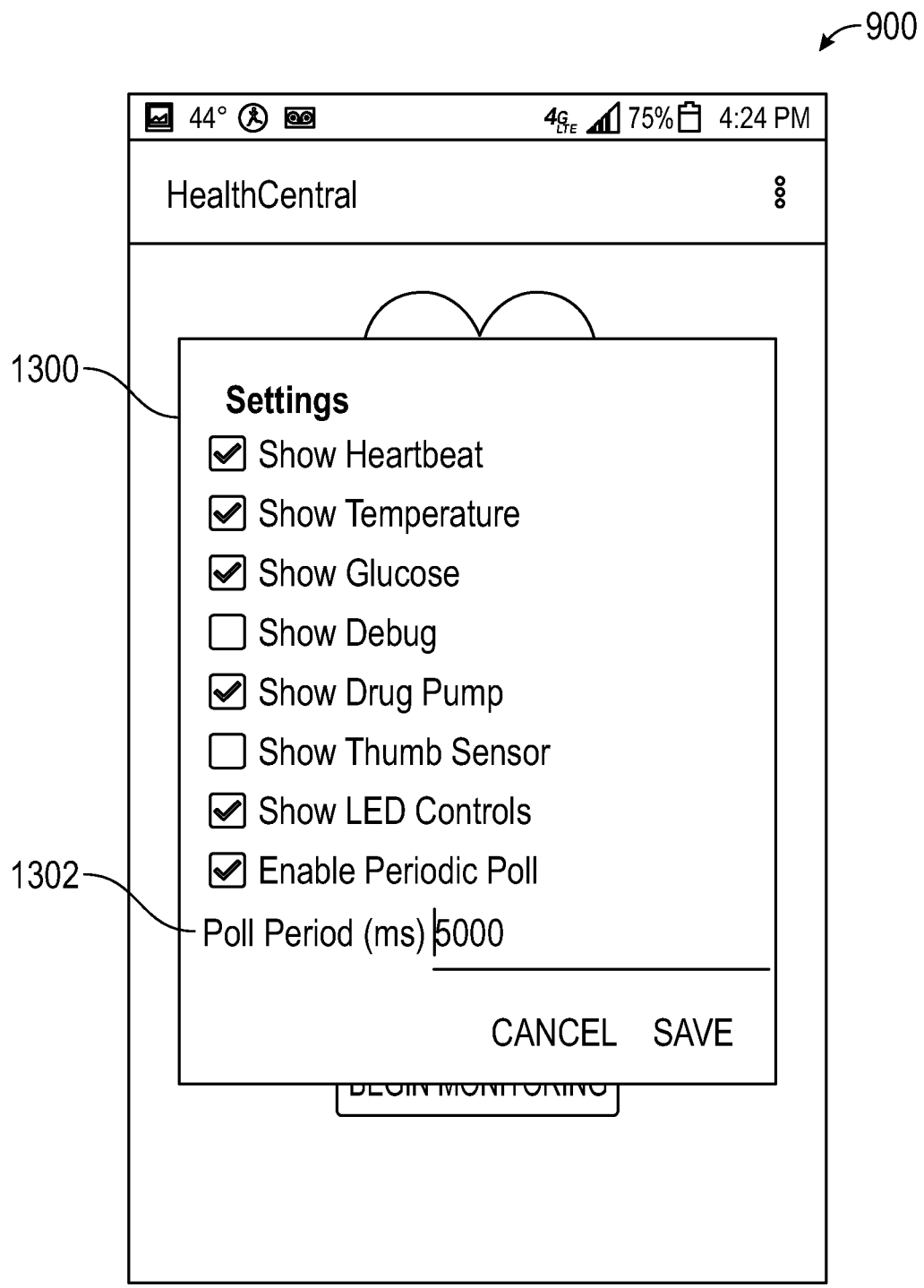
FIG. 13 illustrates a schematic block diagram of an embodiment of a graphical user interface (GUI) generated by the health monitoring application.

FIG. 13 illustrates a schematic block diagram of an embodiment of a graphical user interface (GUI) 600 generated by the health monitoring application 108. The health monitoring application 108 may be implemented in the television 102 or a user device and generate the GUI 900, e.g. on the television 102 or the user device 1000. The GUI 900 displays a Settings GUI 1300 for a user to designate settings for the GUI 900. For example, the Settings GUI 1300 may enable a user to select the various biosensor data displayed, such as heartbeat, temperature, glucose, etc. The health monitoring application 108 may also include a poll period GUI 1302. The poll period GUI 1302 provides an interface for a user to select or input a time period or polling period for a biosensor measurement or other monitoring.

Figure 14A:
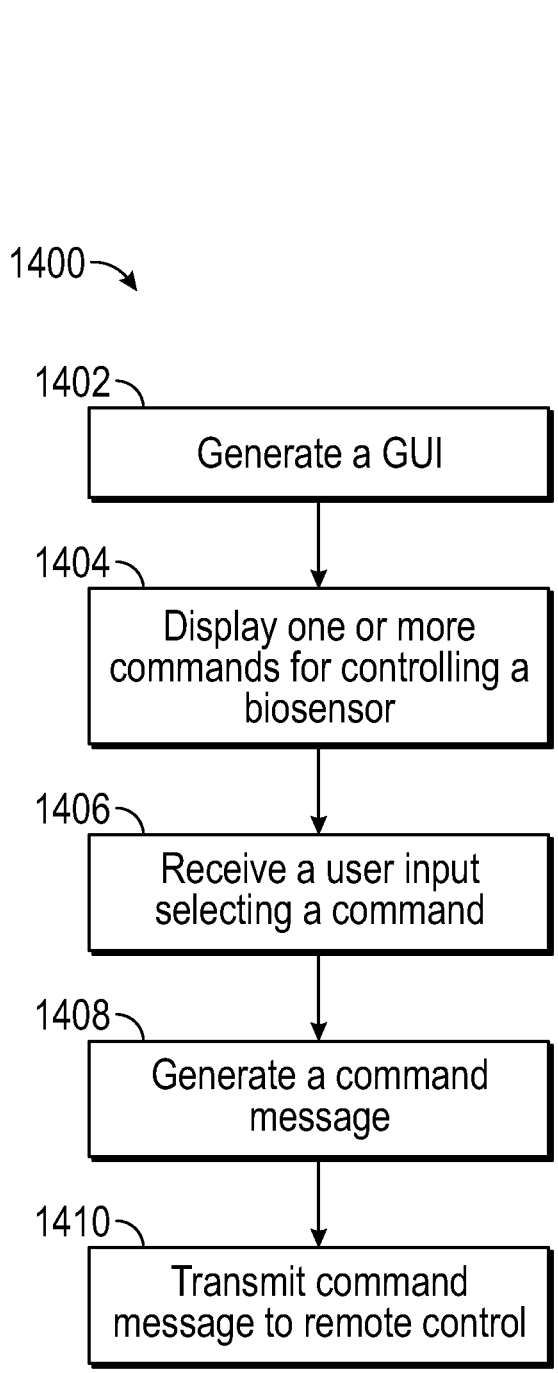
FIG. 14A illustrates a logical flow diagram of an embodiment of a method for the health monitoring application.

FIG. 14A illustrates a logical flow diagram of an embodiment of a method 1400 for the health monitoring application 108. In an embodiment, the HM application 108 may generate a GUI 900 at 1402. The GUI 900 displays one or more commands for controlling a biosensor 150 on the television 102 or on the user device 1000 at 1404. The HM application 108 may receive a user input selecting a command at 1406. The user input may be transmitted from the remote device 100 to the television 102. The HM application 108 generates a command in response to the user input at 1408. The HM application initiates transmission of the command by the wireless transceiver of the television 102 to the remote device 100. The remote device 100 may then transmit the command to an external biosensor to perform the command or initiate an integrated biosensor to perform the command at 1410.

Figure 14B:
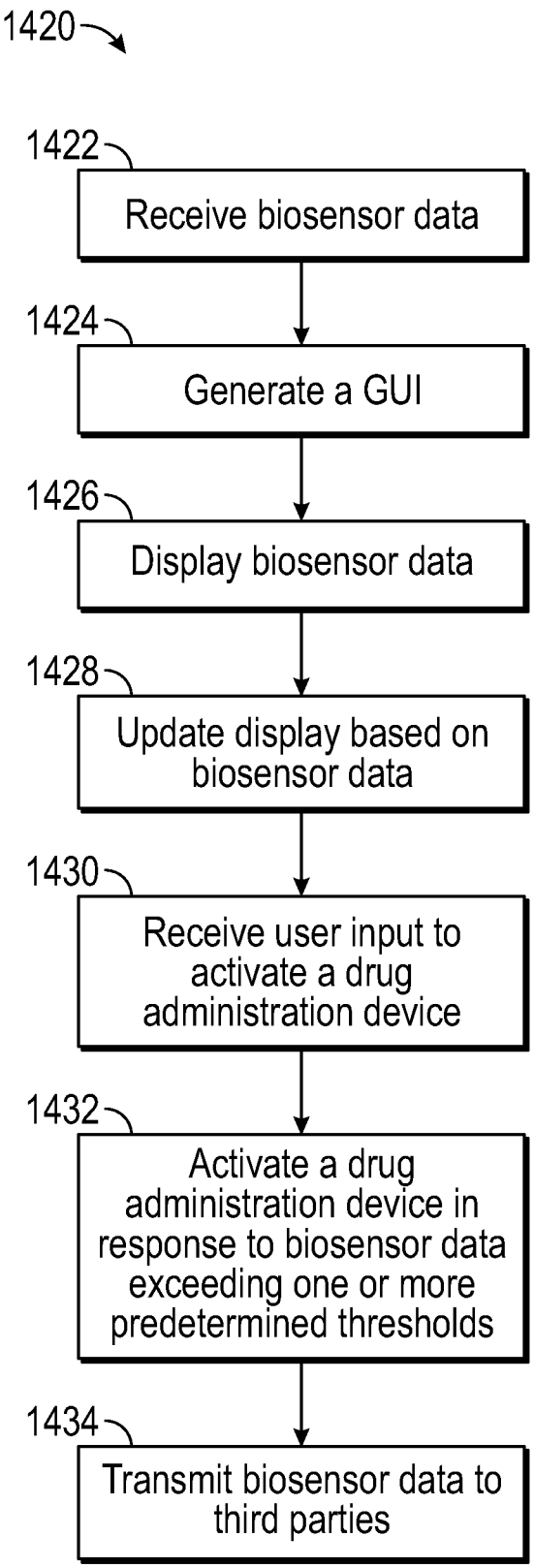
FIG. 14B illustrates a logical flow diagram of an embodiment of a method for the health monitoring application.

FIG. 14B illustrates a logical flow diagram of an embodiment of a method 1420 for the health monitoring (HM) application 108. In an embodiment, the HM application 108 is implemented in a television 100 and receives biosensor data from a remote device 100 at 1422. The HM application 108 may generate a GUI 900 in response to user input at 1424 that displays biosensor data on the television 102 at 1426. The HM application 108 may receive updated biosensor data from the remote device 100. The HM application 108 then updates the display based on the updated biosensor data at 1428. The HM application 108 may also receive a user input to activate a Drug Administration Device at 1430. In another embodiment, the HM application 108 activates a Drug Administration Device when one or more measurements of biosensor data exceed one or more predetermined thresholds at 1432. For example, when glucose levels of a user exceed a predetermined threshold, the HM application 108 may activate an insulin pump to administer insulin to the user.

The HM application may also transmit biosensor data to third parties, such as a doctor's office or pharmacy at 1434. For example, the HM application 108 may generate messages that include requests to refill medications that are transmitted to a pharmacy over a wide area network (WAN). In another example, the HM application 108 may generate messages that include biosensor data that are transmitted to a doctor's hospital over a wide area network (WAN).

Embodiment of a Communication Network

Figure 15:
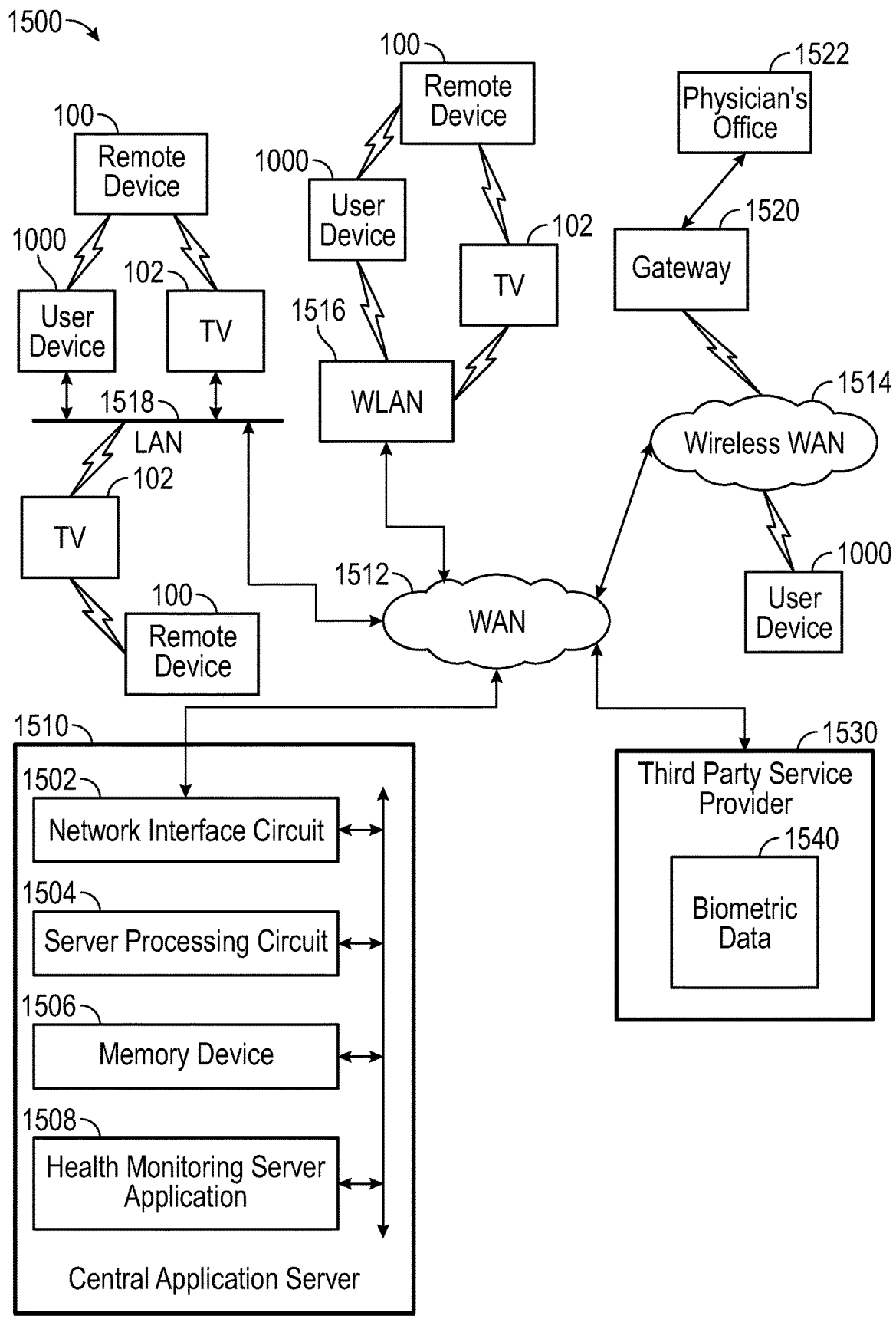
FIG. 15 illustrates a schematic block diagram of an embodiment of an exemplary communication network in which the devices described herein may operate.

FIG. 15 illustrates a schematic block diagram of an embodiment of an exemplary communication network 1500 in which the devices described herein may operate. The exemplary communication network 1500 includes one or more networks that are communicatively coupled, such as a wide area network (WAN) 1512, a wired or wireless local area network (LAN) 1516, a wireless local area network (WLAN) 1516, and a wireless wide area network (WAN) 1512. The LAN 1518 and the WLANs 1516 may operate inside a home or enterprise environment, such as a doctor's office, pharmacy or hospital or other caregiver or business. The wireless WAN 1514 may include, for example, a 3G or 4G cellular network, a GSM network, a WIMAX network, an EDGE network, a GERAN network, etc. or a satellite network or a combination thereof. The WAN 1512 includes the Internet, service provider network, other type of WAN, or a combination of one or more thereof.

One or more televisions (TV) 102 and user devices 1000 are communicatively coupled to a central application server 1510 by one or more of the exemplary networks in the communication network 15000. The central application server 1510 includes a network interface circuit 1502 and a server processing circuit 1504. The network interface circuit 1502 includes an interface for wireless and/or wired network communications with one or more of the exemplary networks in the communication network 1500. The network interface circuit 1502 may also include authentication capability that provides authentication prior to allowing access to some or all of the resources of the central application server 1510. The network interface circuit 1502 may also include firewall, gateway and proxy server functions.

The central application server 1510 also includes a server processing circuit 1504 and a memory device 1506. For example, the memory device 1506 is a non-transitory, processor readable medium that stores instructions from the health monitoring server application 108 which when executed by the server processing circuit 1504, causes the server processing circuit 1504 to perform one or more functions described herein. In an embodiment, the memory device 1506 stores biosensor data for a plurality of patients transmitted to the central application server 1510 from the plurality of televisions 102 and/or user devices 1000.

The central application server 1510 includes a health monitoring server application 1508. The health monitoring server application 1508 is operable to communicate with the plurality of televisions 102 and/or user devices 700. The health monitoring server application 1508 may be a web-based application supported by the central application server 1400. For example, the central application server 1510 may be a web server and support the health monitoring server application 1508 via a website. In another embodiment, the health monitoring application 1508 is a stand-alone application that is downloaded to the user devices 1000 by the central application server 1510 and is operable on the user devices 1000 without access to the central application server 1510 or only needs to accesses the central application server 1510 for additional information, such as biosensor data. Using the health monitoring application 108, the the plurality of televisions 102 and/or user devices 700 are configured to track biosensor data and control certain functions of the the plurality of televisions 102 and/or user devices 700. In addition, the health monitoring server application 1508 supports a user application on one or more of the plurality of televisions 102 and/or user devices 700. The remote devices 100 may communicate directly with one or more televisions 102 and with the one or more user devices 700. For example, the remote devices 100 may communicate using an IR signal with a television 102 and may communicate using a Bluetooth connection with a user device 1000.

The central application server 1510 may also be operable to communicate with a third party content provider 1208 over the communication network 1220 to provide biosensor data. For example, the health monitoring application 108 may provide biosensor data and channel data 1540 to the third party service provider 1530. For example, the health monitoring application 108 may transmit heart rate information or pulse rate information and channel or television tuning data to the third party service provider 1530. The third party service provider 1530 may include a cable provider or broadcast television provider that uses the information to determine interest in a may also transmit the messages to a doctor's office, pharmacy or hospital or other caregiver or business over the communication network 1500 as requested or needed.

Figure 16:
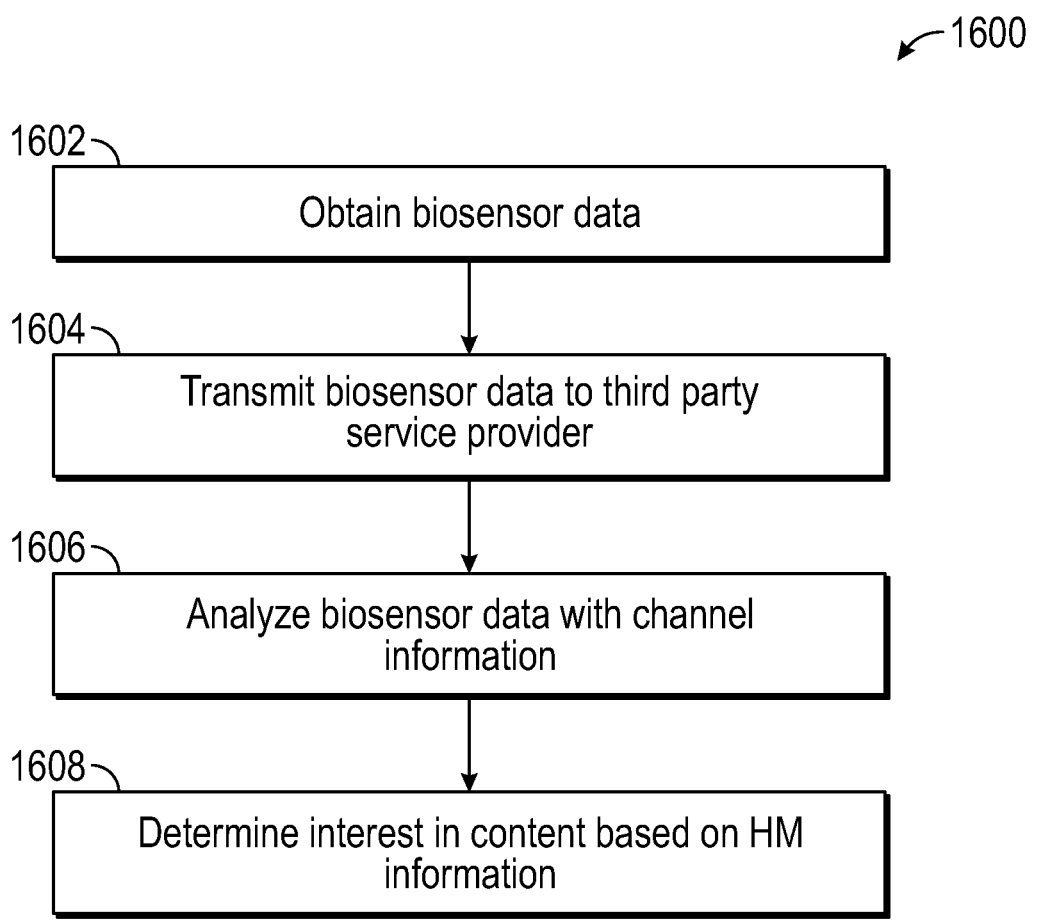
FIG. 16 illustrates a logic flow diagram of an exemplary embodiment of a method for analyzing content based on HM information.

FIG. 16 illustrates a logic flow diagram of an exemplary embodiment of a method 1600 for analyzing content based on HM information. The third party service provider is configured to receive and process biosensor data from the remote 100 and television 102. The remote 102 is configured to receive and monitor bio sensor data from one or more external or integrated biosensors 150. For example, the biosensors 150 may detect an indicator of glucose levels, alcohol levels or other analytes. In addition, the biosensor 150 may also include a pulse oximeter to determine pulse and oxygen levels. The biosensor 150 may also detect blood pressure, peripheral oxygen (SpO2) saturation amounts, body temperature, various electrolytes and many common blood analytic levels, such as bilirubin amount and sodium and potassium. The biosensor may also detect blood alcohol levels.

The biosensor data is obtained by the remote device 100 at 1602 and transmitted to the television 102. The television 102 transmits biosensor data to the third party service provider 1530 at 1604. The third party service provider analyzes the biosensor data and channel information 1606. For example, the biosensor data may include pulse rate or activity levels. Based on the biosensor data, the third party service provider determines an interest in television show or channel by a user at 1608. For example, when the biosensor data shows that a pulse rate increases during display of certain channel content, the third party service provider may determine the user has an interest in the channel content, such as a commercial or television show.

Embodiment—PPG Circuit

Figure 17:
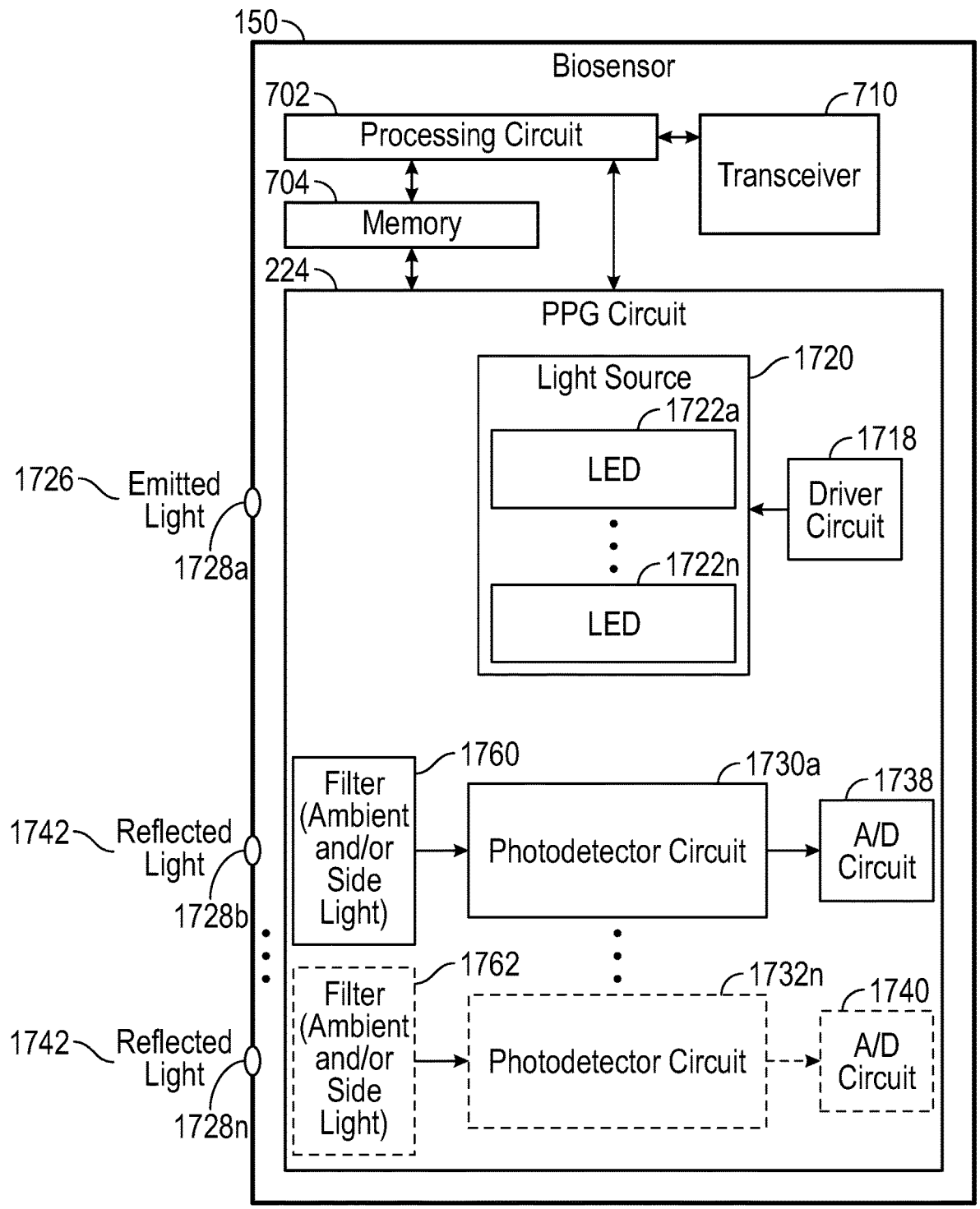
FIG. 17 illustrates a schematic block diagram illustrating an embodiment of the PPG circuit in more detail.

FIG. 17 illustrates a schematic block diagram illustrating an embodiment of the PPG circuit 224 in more detail. The PPG circuit 224 implements photoplethysmography (PPG) techniques for obtaining concentration levels or indicators of one or more substances in pulsating arterial blood flow. The PPG circuit 224 includes a light source 1720 having a plurality of light sources, such as LEDs 1722*a-n*, configured to emit light through at least one aperture 1728*a*. The PPG circuit 224 is configured to direct the emitted light at an outer or epidermal layer of skin tissue of a patient. The plurality of light sources are configured to emit light in one or more spectrums, including infrared (IR) light, ultraviolet (UV) light, near IR light or visible light, in response to driver circuit 1718. For example, the biosensor 150 may include a first LED 1722*a* that emits visible light and a second LED 1722*b* that emits infrared light and a third LED 1722*c* that emits UV light, etc. In another embodiment, one or more of the light sources 1722*a-n* may include tunable LEDs or lasers operable to emit light over one or more frequencies or ranges of frequencies or spectrums in response to driver circuit 1718.

In an embodiment, the driver circuit 1718 is configured to control the one or more LEDs 1722*a-n* to generate light at one or more frequencies for predetermined periods of time. The driver circuit 118 may control the LEDs 1722*a-n* to operate concurrently or progressively. The driver circuit 118 is configured to control a power level, emission period and frequency of emission of the LEDs 1722*a-n*. The biosensor 150 is thus configured to emit one or more frequencies of light in one or more spectrums that is directed at the surface or epidermal layer of the skin tissue of a patient.

The PPG circuit 224 further includes one or more photodetector circuits 1730*a-n*. For example, a first photodetector circuit 1730 may be configured to detect visible light and the second photodetector circuit 1730 may be configured to detect IR light. The first photodetector circuit 1730 and the second photodetector circuit 130 may also include a first filter 1760 and a second filter 1762 configured to filter ambient light and/or scattered light. For example, in some embodiments, only light received at an approximately perpendicular angle to the skin surface of the patient is desired to pass through the filters. The first photodetector circuit 1730 and the second photodetector circuit 1732 are coupled to a first A/D circuit 1738 and a second A/D circuit 1740. The A/D circuits 1738 and 1740 may also include an amplifier and other components needed to generate the spectral response. In another aspect, the plurality of photodetectors 1730 is coupled in parallel to a single amplifier and A/D circuit 1738. The light detected by each of the photodetectors 1730 is thus added and amplified to generate a single spectral response.

In another embodiment, a single photodetector circuit 1730 may be implemented operable to detect light over multiple spectrums or frequency ranges. For example, the photodetector circuit 1730 may include a Digital UV Index/IR/Visible Light Sensor such as Part No. Si1145 from Silicon Labs™.

The one or more photodetector circuits 1730 include a spectrometer or other type of circuit configured to detect an intensity of light as a function of wavelength or frequency to obtain a spectral response. The one or more photodetector circuits 1730 detect the intensity of light either transmitted through or reflected from tissue of a patient that enters one or more apertures 1728*b-n* of the biosensor 150. For example, the light may be detected from transmissive absorption (e.g., through a fingertip or ear lobe) or from reflection (e.g., reflected from a forehead or stomach tissue). The photodetector circuits 1730*a-n* then obtain a spectral response of the detected light by measuring the intensity of light either transmitted or reflected to the photodiodes.

Figure 18:
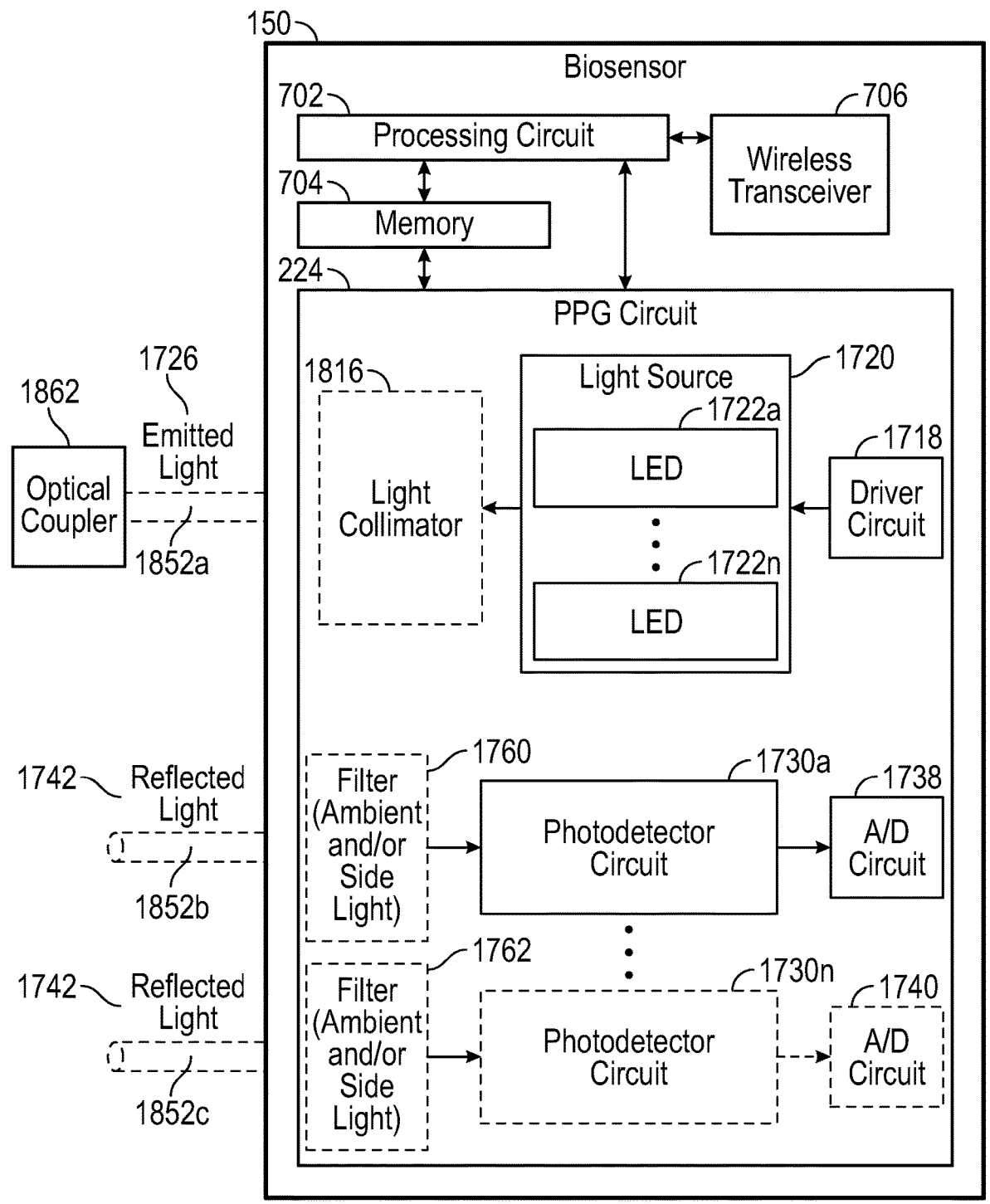
FIG. 18 illustrates a schematic block diagram of another exemplary embodiment of the the PPG circuit.

FIG. 18 illustrates a schematic block diagram of another exemplary embodiment of the the PPG circuit 224. In this embodiment, the biosensor 150 is configured for emitting and detecting light through one or more optical fibers 1852*a-c*. The PPG circuit 224 is optically coupled to a plurality of optical fibers 1852*a-c*. In an embodiment, the plurality of optical fibers 1852*a-c* includes a first optical fiber 1852*a* optically coupled to the light source 1720. An optical coupler (not shown) to spread the angle of light emitted from the optical fiber 1852*a* may also be implemented. The optical fiber 1852*a* may have a narrow viewing angle such that an insufficient area of skin surface is exposed to the light. An optical coupler 1862 may be used to widen the viewing angle to increase the area of skin surface exposed to the light.

A second optical fiber 1852*b* is optically coupled to a first photodetector circuit 1730*a* and a third optical fiber 1852*c* is optically coupled to the second photodetector circuit 1730*n*. Other configurations and numbers of the plurality of optical fibers 1852 may also be implemented.

In one aspect, the plurality of optical fibers 1852 is situated within an outer ear canal to transmit and detect light in the ear canal. A light collimator 1816, such as a prism, may be used to align a direction of the light emitted from the light source 1720. One or more filters 1760, 1762 may optionally be implemented to receive the reflected light 1742 from the plurality of optical fibers 1852b, 1852c. However, the filters 1760, 1762 may not be needed as the plurality of optical fibers 1852b, 1852c may be sufficient to filter ambient light and/or scattered light.

Figure 19:
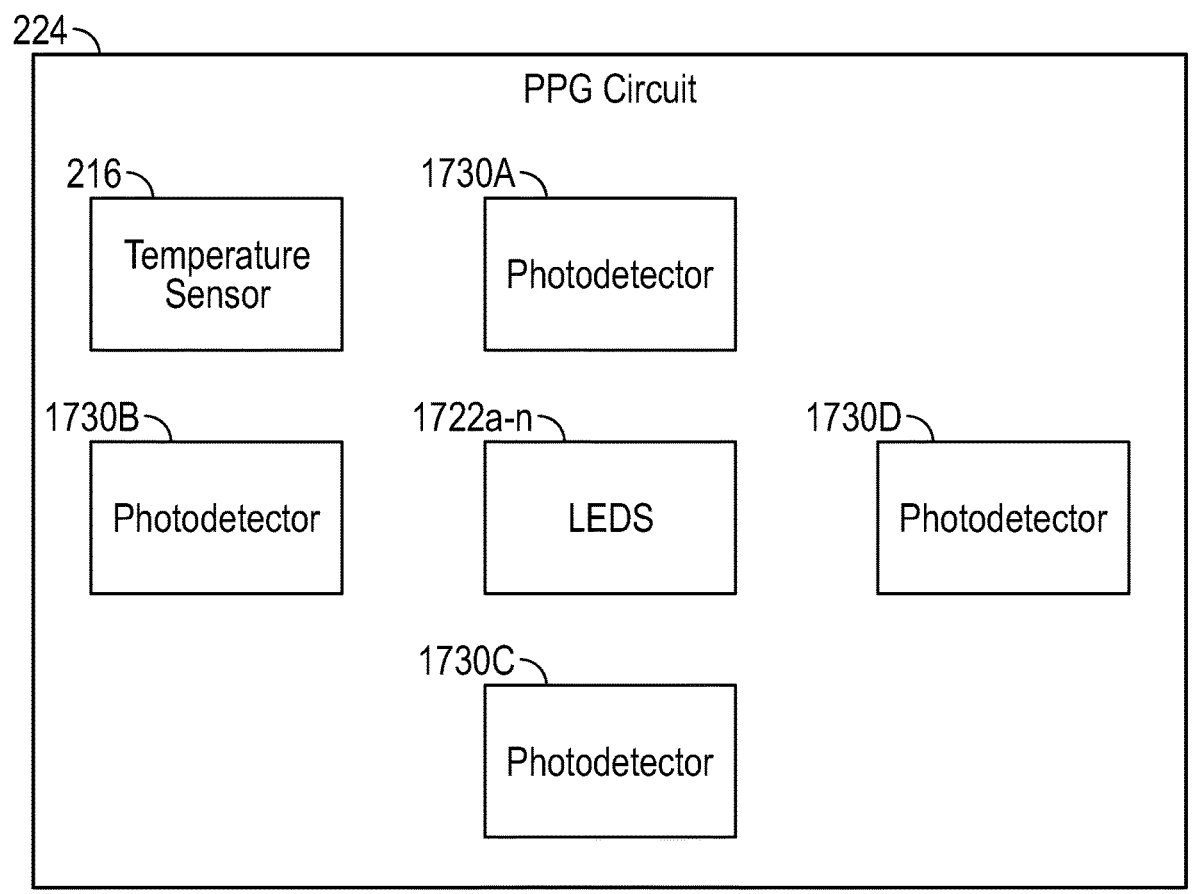
FIG. 19 illustrates a schematic block diagram of an embodiment of the PPG circuit 224 with a plurality of photodetectors.

FIG. 19 illustrates a schematic block diagram of an embodiment of the PPG circuit 224 with a plurality of photodetectors 1730. In one aspect, the plurality of photodetectors 1730 are situated in different physical positions and orientations in the biosensor 150. For example, at least four photodetectors 1730a, 1730b, 1730c and 1730d are situated in the biosensor 150 in four different physical positions in a North-South and East-West orientation or polarity. The output signals of the plurality of photodetectors are coupled in parallel to the amplifier and A/D circuit 1738. The light signals detected by each of the photodetectors 1730 through an aperture 1728 in the biosensor are added and amplified to generate a single spectral response. The spectral response is thus more robust and less affected by motion artifacts and movement of the biosensor 150. The LEDs 1722a-n may be situated centrally to the physical position of the plurality of photodetectors 1730. The temperature sensor 216 may also be physically situated near the PPG circuit 224 to detect temperature through an aperture 1728.

Embodiment—PPG Measurement of Arterial Blood Flow

One or more of the embodiments of the biosensor 150 described herein are configured to detect a concentration level or indicator of one or more substances within blood flow, such as analyte levels, nitric oxide levels, insulin resistance or insulin response after caloric intake and predict diabetic risk or diabetic precursors. The biosensor 150 may detect insulin response, vascular health, cardiovascular sensor, cytochrome P450 proteins (e.g. one or more liver enzymes or reactions), digestion phase 1 and 2 or caloric intake. The biosensor 150 may even be configured to detect proteins or other elements or compounds associated with cancer. The biosensor 150 may also detect various electrolytes and many common blood analytic levels, such as bilirubin amount and sodium and potassium. For example, the biosensor 150 may detect sodium NACL concentration levels in the arterial blood flow to determine dehydration. The biosensor 150 may also detect blood alcohol levels in vivo in the arterial blood flow. Because blood flow to the skin can be modulated by multiple other physiological systems, the biosensor 150 may also be used to monitor breathing, hypovolemia, and other circulatory conditions. The biosensor 150 may also detect blood pressure, peripheral oxygen (SpO$_2$ or SaO$_2$) saturation, heart rate, respiration rate or other patient vitals. The biosensor 150 may also be used to detect sleep apnea based on oxygen saturation levels and activity monitoring during sleep.

In use, the biosensor 150 performs PPG techniques using the PPG circuit 224 to detect the concentration levels of substances in blood flow. In one aspect, the biosensor 150 analyzes reflected visible or IR light to obtain a spectrum response such as, the resonance absorption peaks of the reflected visible, UV or IR light. The spectrum response includes spectral lines that illustrate an intensity or power or energy at a wavelength or range of wavelengths in a spectral region of the detected light.

The ratio of the resonance absorption peaks from two different frequencies can be calculated and based on the Beer-Lambert law used to obtain various levels of substances in the blood flow. First, the spectral response of a substance or substances in the arterial blood flow is determined in a controlled environment, so that an absorption coefficient $\alpha_{g1}$ can be obtained at a first light wavelength $\lambda_1$ and at a second wavelength $\lambda_2$. According to the Beer-Lambert law, light intensity will decrease logarithmically with path length l (such as through an artery of length l). Assuming then an initial intensity $I_{in}$ of light is passed through a path length 1, a concentration $C_g$ of a substance may be determined using the following equations:

At the first wavelength $\lambda_1, I_1 = I_{in1} * 10^{-(\alpha_{g1}C_{gw} + \alpha_{w1}C_w)*l}$ At the second wavelength $\lambda_2, I_2 = I_{in2} * 10^{-(\alpha_{g2}C_{gw} + \alpha_{w2}C_w)*l}$ wherein:
$I_{in1}$ is the intensity of the initial light at $\lambda_1$
$I_{in2}$ is the intensity of the initial light at $\lambda_2$
$\alpha_{g1}$ is the absorption coefficient of the substance in arterial blood at $\lambda_1$
$\alpha_{g2}$ is the absorption coefficient of the substance in arterial blood at $\lambda_2$
$\alpha_{w1}$ is the absorption coefficient of arterial blood at $\lambda_1$
$\alpha_{w1}$ is the absorption coefficient of arterial blood at $\lambda_2$
$C_{gw}$ is the concentration of the substance and arterial blood
$C_w$ is the concentration of arterial blood
Then letting R equal:

$$R = \frac{\log 10\left(\frac{I1}{I in1}\right)}{\log 10\left(\frac{I2}{I in2}\right)}$$

The concentration of the substance Cg may then be equal to:

$$Cg = \frac{Cgw}{Cgw + Cw} = \frac{\alpha_{w2}R - \alpha_{w1}}{(\alpha_{w2} - \alpha_{gw2}) * R - (\alpha_{w1} - \alpha_{gw1})}$$

The biosensor 150 may thus determine the concentration of various substances in arterial blood using spectroscopy at two different wavelengths using Beer-Lambert principles.

The biosensor 150 determines concentration of one or more substances using Beer-Lambert principles. The biosensor 150 transmits light at least at a first predetermined wavelength and at a second predetermined wavelength. The biosensor 150 detects the light (reflected from the skin or transmitted through the skin) and analyzes the spectral response at the first and second wavelengths to detect an indicator or concentration level of one or more substances in the arterial blood flow. In general, the first predetermined wavelength is selected that has a high absorption coefficient for the targeted substance while the second predetermined wavelength is selected that has a low absorption coefficient for the targeted substance. Thus, it is generally desired that the spectral response for the first predetermined wavelength have a higher intensity level than the spectral response for the second predetermined wavelength.

In another aspect, the biosensor 150 may transmit light at the first predetermined wavelength and in a range of approximately 1 nm to 50 nm around the first predetermined wavelength. Similarly, the biosensor 150 may transmit light at the second predetermined wavelength and in a range of approximately 1 nm to 50 nm around the second predetermined wavelength. The range of wavelengths is determined based on the spectral response since a spectral response may extend over a range of frequencies, not a single frequency (i.e., it has a nonzero linewidth). The light that is reflected or transmitted light by the target substance may by spread over a range of wavelengths rather than just the single predetermined wavelength. In addition, the center of the spectral response may be shifted from its nominal central wavelength or the predetermined wavelength. The range of 1 nm to 50 nm is based on the bandwidth of the spectral response line and should include wavelengths with increased light intensity detected for the targeted substance around the predetermined wavelength.

The first spectral response of the light over the first range of wavelengths including the first predetermined wavelength and the second spectral response of the light over the second range of wavelengths including the second predetermined wavelengths is then generated. The biosensor 150 analyzes the first and second spectral responses to detect an indicator or concentration level of one or more substances in the arterial blood flow.

Photoplethysmography (PPG) is used to measure time-dependent volumetric properties of blood in blood vessels due to the cardiac cycle. For example, the heartbeat affects volume of arterial blood flow and the concentration of absorption levels being measured in the arterial blood flow. Over a cardiac cycle, pulsating arterial blood changes the volume of blood flow in an artery. Incident light $I_O$ is directed at a tissue site and a certain amount of light is reflected or transmitted and a certain amount of light is absorbed. At a peak of arterial blood flow or arterial volume, the reflected/transmitted light $I_L$ is at a minimum due to absorption by the venous blood, nonpulsating arterial blood, pulsating arterial blood, other tissue, etc. At a minimum of arterial blood flow or arterial volume during the cardiac cycle, the transmitted/reflected light $I_H$ is at a maximum due to lack of absorption from the pulsating arterial blood.

The biosensor 150 is configured to filter the reflected/transmitted light $I_L$ of the pulsating arterial blood from the transmitted/reflected light $I_H$. This filtering isolates the light due to reflection/transmission of substances in the pulsating arterial blood from the light due to reflection/transmission from venous (or capillary) blood, other tissues, etc. The biosensor 150 may then measure the concentration levels of one or more substances from the reflected/transmitted light $I_L$ in the pulsating arterial blood. Though the above has been described with respect to arterial blood flow, the same principles described herein may be applied to venous blood flow.

In general, the relative magnitudes of the AC and DC contributions to the reflected/transmitted light signal I may be used to substantially determine the differences between the diastolic time and the systolic points. In this case, the difference between the reflected light $I_L$ and reflected light $I_H$ corresponds to the AC contribution of the reflected light (e.g. due to the pulsating arterial blood flow). A difference function may thus be computed to determine the relative magnitudes of the AC and DC components of the reflected light I to determine the magnitude of the reflected light $I_L$ due to the pulsating arterial blood. The described techniques herein for determining the relative magnitudes of the AC and DC contributions is not intended as limiting. It will be appreciated that other methods may be employed to isolate or otherwise determine the relative magnitude of the light $I_L$ due to pulsating arterial blood flow.

Figure 20:
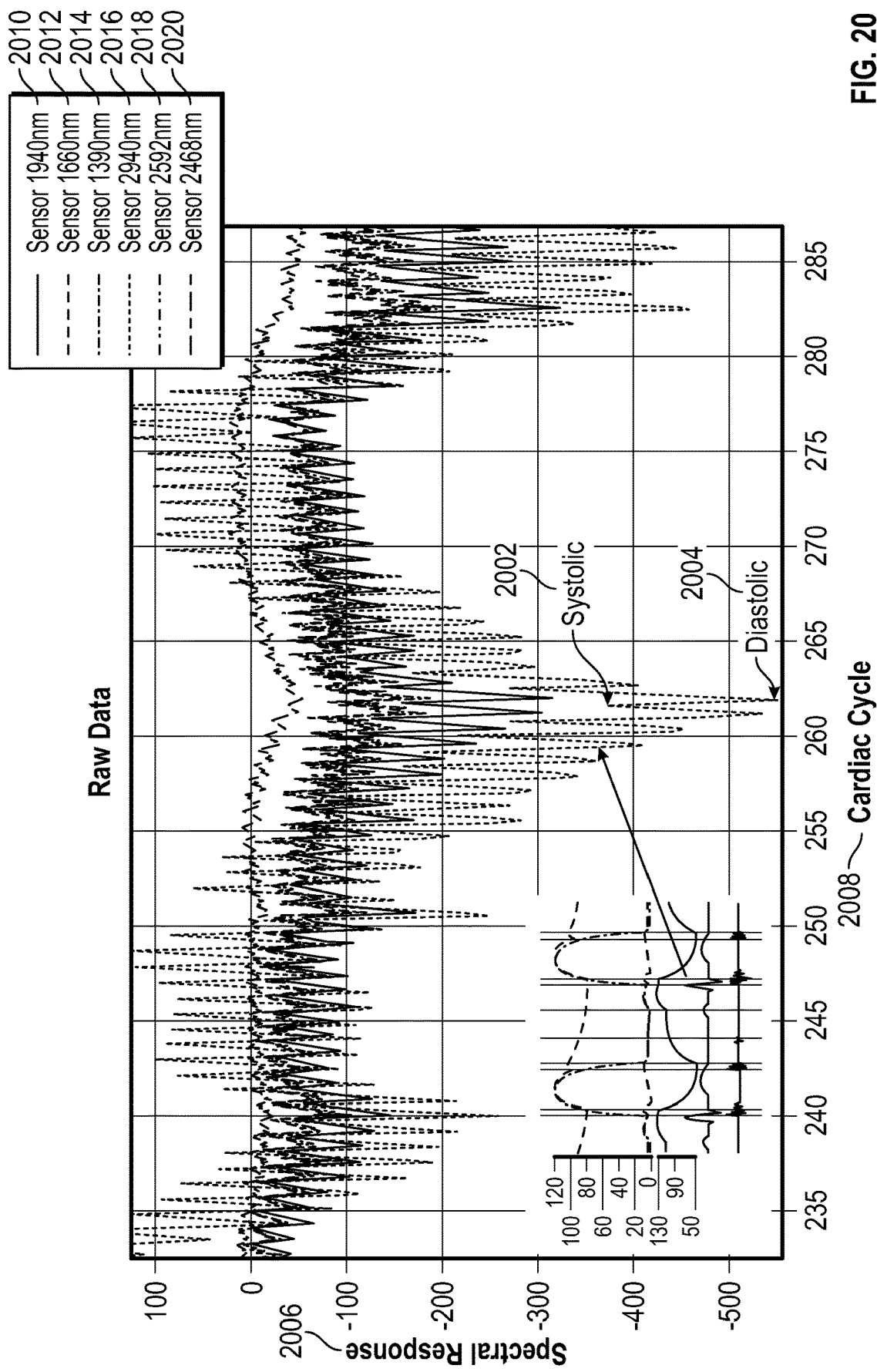
FIG. 20 illustrates a schematic diagram of a graph of actual clinical data obtained using PPG techniques at a plurality of wavelengths.

FIG. 20 illustrates a schematic diagram of a graph of actual clinical data obtained using PPG techniques at a plurality of wavelengths. The biosensor 150 emits light having a plurality of wavelengths during a measurement period. The light at each wavelength (or range of wavelengths) may be transmitted concurrently or sequentially. The intensity of the reflected light at each of the wavelengths (or range of wavelengths) is detected and the spectral response is measured over the measurement period. The spectral response 2006 for the plurality of wavelengths obtained using the biosensor in clinical trials is shown in FIG. 20. In this clinical trial, two biosensors 150 attached to two separate fingertips of a patient were used to obtain the spectral responses 2006. The first biosensor 150 obtained the spectral response for a wavelength at 940 nm 2010, a wavelength at 660 nm 2012 and a wavelength at 390 nm 2014. The second biosensor 150 obtained the spectral response for a wavelength at 940 nm 2016, a wavelength at 592 nm 2018 and a wavelength at 468 nm 2020.

In one aspect, the spectral response of each wavelength may be aligned based on the systolic 2002 and diastolic 2004 points in their spectral responses. This alignment is useful to associate each spectral response with a particular stage or phase of the pulse-induced local pressure wave within the blood vessel (which may mimic the cardiac cycle 2008 and thus include systolic and diastolic stages and sub-stages thereof). This temporal alignment helps to determine the absorption measurements acquired near a systolic point in time of the cardiac cycle 2008 and near the diastolic point in time of the cardiac cycle 2008 associated with the local pressure wave within the patient's blood vessels. This measured local pulse timing information may be useful for properly interpreting the absorption measurements in order to determine the relative contributions of the AC and DC components measured by the biosensor 150. So for one or more wavelengths, the systolic points 2002 and diastolic points 2004 in the spectral response are determined. These systolic points 2002 and diastolic points 2004 for the one or more wavelengths may then be aligned as a method to discern concurrent responses across the one or more wavelengths.

In another embodiment, the the systolic points 2002 and diastolic points 2004 in the absorbance measurements are temporally correlated to the pulse-driven pressure wave within the arterial blood vessels—which may differ from the cardiac cycle. In another embodiment, the biosensor 150 may concurrently measure the intensity reflected at each the plurality of wavelengths. Since the measurements are concurrent, no alignment of the spectral responses of the plurality of wavelengths may be necessary.

Figure 21:
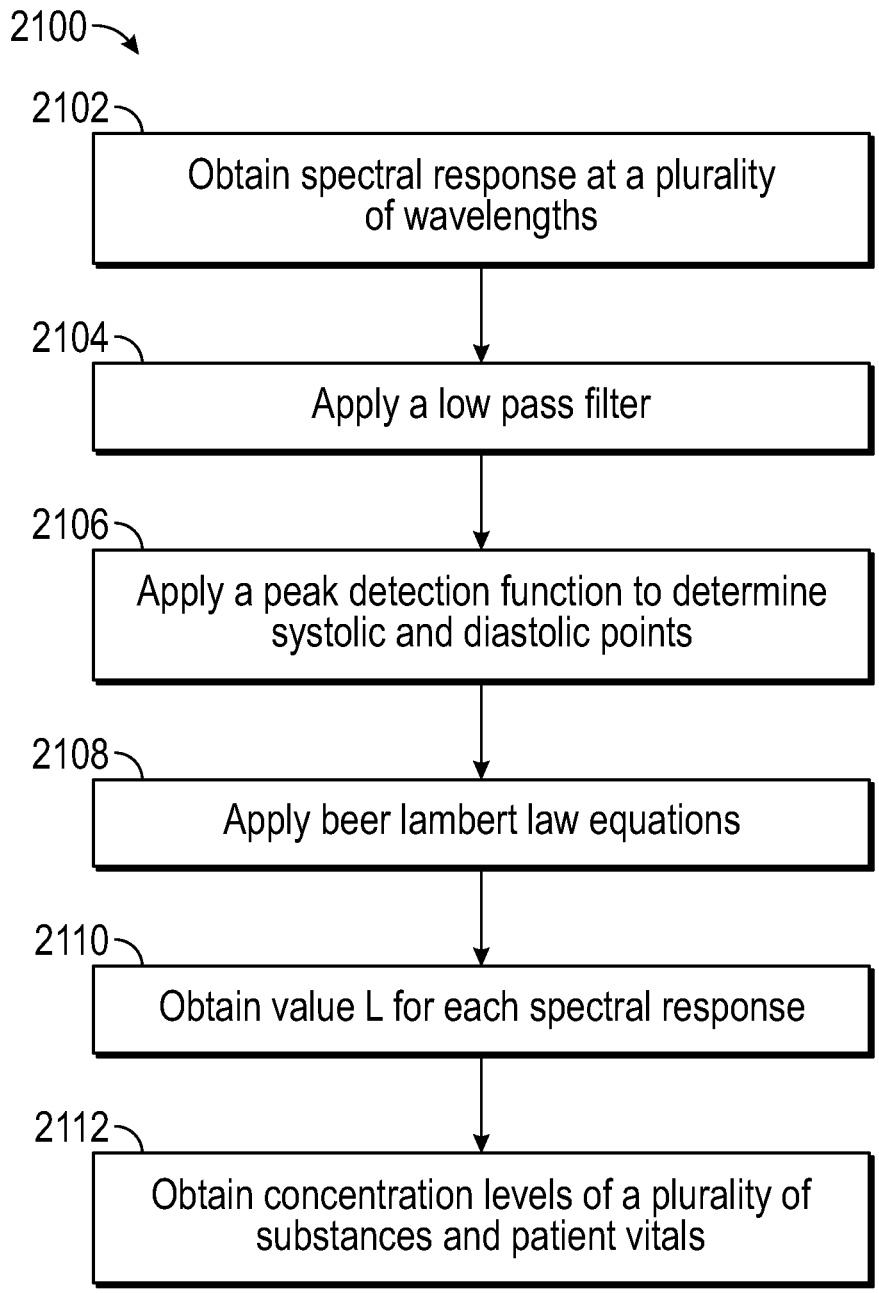
FIG. 21 illustrates a logical flow diagram of an embodiment of a method 2100 of the biosensor.

FIG. 21 illustrates a logical flow diagram of an embodiment of a method 2100 of the biosensor 150. In one aspect, the biosensor 150 emits and detects light at a plurality of predetermined frequencies or wavelengths, such as approximately 940 nm, 660 nm, 390 nm, 592 nm, and 468 nm. The light is pulsed for a predetermined period of time (such as 100 usec or 200 Hz) sequentially at each predetermined wavelength. In another aspect, light may be pulsed in a wavelength range of 1 nm to 50 nm around each of the predetermined wavelengths. Then, the spectral responses are obtained for the plurality of wavelengths at 2102. The spectral response may be measured over a predetermined period (such as 300 usec.). This measurement process is repeated sequentially pulsing the light and obtaining spectral measurements over a desired measurement period, e.g. from 1-2 seconds to 1-2 minutes or 2-3 hours or continuously over days or weeks. Because the human pulse is typically on the order of magnitude of one 1 HZ, typically the time differences between the systolic and diastolic points are on the order of magnitude of milliseconds or tens of milliseconds or hundreds of milliseconds. Thus, spectral response measurements may be obtained at a frequency of around 10-100 Hz over the desired measurement period.

A low pass filter (such as a 5 Hz low pass filter) is applied to the spectral response signal at 2104. The relative contributions of the AC and DC components are obtained $I_{AC+DC}$ and $I_{AC}$. A peak detection algorithm is applied to determine the systolic and diastolic points at 2106. Beer Lambert equations are applied as described below at 2108. For example, the $L_\lambda$ values are then calculated for one or more of the wavelengths λ, wherein the $L_\lambda$ values for a wavelength equals:

$$L_\lambda = \text{Log}10\left(\frac{IAC+DC}{IDC}\right)$$

wherein $I_{AC+DC}$ is the intensity of the detected light with AC and DC components and $I_{DC}$ is the intensity of the detected light with the AC filtered by the low pass filter at 2110. The value $L_\lambda$ isolates the spectral response due to pulsating arterial blood flow, e.g. the AC component of the spectral response.

A ratio R of the $L_\lambda$ values at two wavelengths may then be determined. For example, $$\text{Ratio } R = \frac{L\lambda 1}{L\lambda 2}$$

The $L_\lambda$ values and Ratio R may be determined for one or more of the predetermined measurement periods over a desired time period, e.g. from 1-2 seconds to 1-2 minutes or 2-3 hours or continuously over days or weeks to monitor the values. The $L_\lambda$ values and Ratio R may be used to determine concentration levels of one or more substances in the arterial blood flow at 2112 as well as patient vitals, such as oxygen saturation SpO2, heart rate, respiration rate, etc.

Embodiment—Determination of Indicators or Concentration Levels of One or More Substances In one aspect, based on unexpected results from clinical trials, it was determined that a ratio $R_{390,940}$ obtained at approximately $L_{\lambda 1}$=390 nm and $L_2$=940 is useful as a predictor or indicator of diabetic risk or diabetes. For example, during experimental clinical trials, spectral responses were obtained during predetermined measurement periods over a 1-2 minute time period at 390 nm and 940 nm. An $R_{390,940}$ value was obtained based on the spectral responses measured during a plurality of the predetermined measurement periods over the 1-2 minute time period. From the unexpected results of the clinical trials, an average or mean $R_{390,940}$ value of less than 1 (e.g., approximately 0.5) indicated that a person has diabetes or early onset of diabetes. An average or mean $R_{390,940}$ value of 2 or above indicated that a person has a lower risk of a diabetes diagnosis. An average or mean $R_{390,940}$ value in the 5-6 range indicated no current risk of diabetes. The $R_{390,940}$ value determined using $L_{\lambda 1}$=390 nm and $L_{\lambda 2}$=940 was thus an indicator of diabetic risk and diabetes. Thus, based on the clinical trials, a non-invasive, quick 1-2 minute test produced an indicator of diabetes or diabetic risk in a person.

In particular, in unexpected results, it is believed that nitrous oxide NO levels in the arterial blood flow is being measured at least in part by the biosensor 150 at λ1=390 nm. Since NO is partly in a gaseous form in blood vessels (prior to adhesion to hemoglobin), the total NO concentration levels of in vitro blood samples, e.g. from a finger prick, are not detected as the gas dissipates. Thus, the biosensor 150 measurements to determine the $L_{390\ nm}$ values are the first time NO concentration levels in arterial blood flow have been measured directly in vivo. In clinical trials performed as described further herein, in unexpected results, it seems that the NO levels are an indication of insulin response in the blood as well as concentration levels of insulin and/or glucose levels in the blood. The $L_{\lambda 1=390\ nm}$ and R value obtained from $L_{\lambda 1=390\ nm}$ are thus an indicator of blood glucose levels, insulin response and diabetic risk as well as vascular health. These unexpected results have advantages in early detection of diabetic risk and easier, non-invasive monitoring of insulin resistance and glucose levels as well as vascular health and other conditions. These results are discussed in more detail herein with illustrative experimental data.

The biosensor 150 may also function as a pulse oximeter using similar principles under Beer-lambert law to determine pulse and oxygen saturation levels in pulsating arterial flow. For example, a first wavelength at approximately 940 nm and a second wavelength at approximately 660 nm may be used to determine oxygen saturation levels.

The biosensor 150 may also be used to determine alcohol levels in the blood using wavelengths at approximately 390 nm and/or 468 nm. In another embodiment, an $R_{468,940}$ value for at least $L_{468\ nm}/L_{940\ nm}$ may be used as a liver enzyme indicator, e.g. P450 enzyme indicator. In another embodiment, an $R_{592,940}$ value for at least $L_{592\ nm}/L_{940\ nm}$ may be used as a digestive indicator to measure digestive responses, such as phase 1 and phase 2 digestive stages. The biosensor 150 may also detect other types of electrolytes or analytes, such as sodium and potassium, using similar PPG techniques. In another aspect, the biosensor 150 may detect which blood cell levels in arterial blood flow using similar PPG techniques.

In another aspect, abnormal cells or proteins or compounds that are present or have higher concentrations in the blood with persons having cancer, may be detected using similar PPG techniques described herein at one or more other wavelengths. Thus, cancer risk may then be obtained through non-invasive testing by the biosensor 150.

Since the biosensor 150 may operate in multiple frequencies, various health monitoring tests may be performed concurrently and continuously. These tests may be performed throughout a hospital stay or may be non-invasively and quickly and easily obtained using the biosensor 150 in a physician's office or other clinical setting or at home. These and other aspects of the biosensor 150 are described in more detail herein with clinical trial results.

Figure 22:
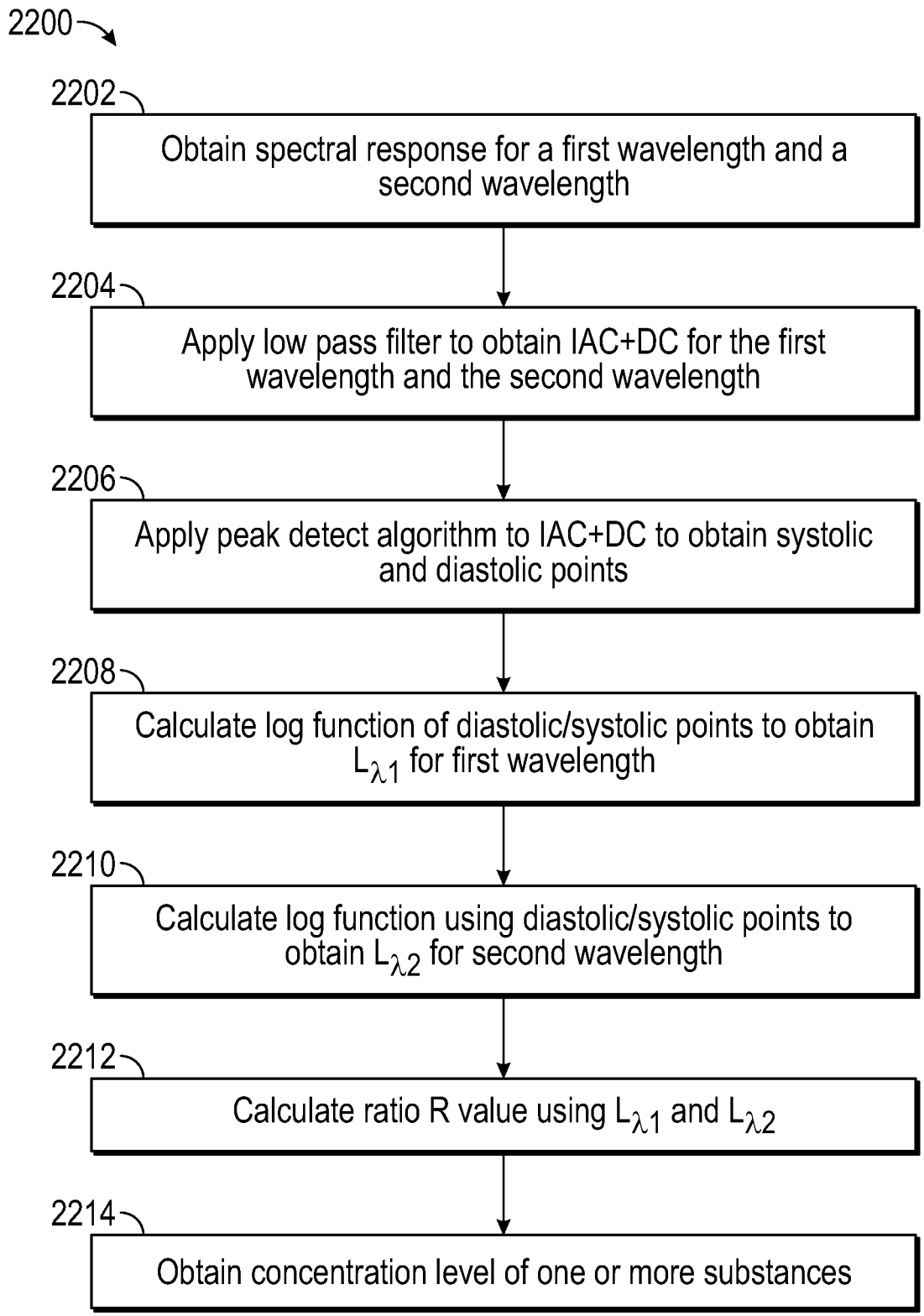
FIG. 22 illustrates a logical flow diagram of an embodiment of a method 2200 of determining concentration levels of one or more substances in more detail.

FIG. 22 illustrates a logical flow diagram of an embodiment of a method 2200 of determining concentration levels of one or more substances in more detail. The biosensor 150 obtains a first spectral response signal including a first wavelength and a second response signal including a second wavelength at 2202. In general, the first wavelength is selected that has a high absorption coefficient for the targeted substance while the second wavelength is selected that has a low absorption coefficient for the targeted substance. Thus, it is generally desired that the spectral response for the first predetermined wavelength have a higher intensity level than the spectral response for the second predetermined wavelength.

Each of the spectral response signals includes AC and DC components $I_{AC+DC}$. A low pass filter is applied to the spectral response signals $I_{AC+DC}$ to isolate the DC component of the first and second spectral response signals $I_{DC}$ at 2204. The AC fluctuation is due to the pulsatile expansion of the arteriolar bed due to the volume increase in arterial blood. In order to measure the AC fluctuation, measurements are taken at different times and a peak detection algorithm or other means is used to determine the diastolic point and the systolic point of the spectral response at 2206. The systolic and diastolic measurements are compared in order to compute the aforementioned R ratio. For example, a logarithmic function may be applied to the ratio of $I_{AC+DC}$ and $I_{DC}$ to obtain an L value for the first wavelength $L_{\lambda 1}$ at 2208 and for the second wavelength $L_{\lambda 2}$ at 2210. The ratio R of the $L_\lambda$ values may then be calculated at 2212. The $L_\lambda$ values and Ratio R may be used to determine concentration levels of one or more substances in the arterial blood flow at 2214.

In one aspect, the biosensor 150 may include a broad spectrum light source 1020, such as a white light to infrared (IR) or near IR LED 1022, that emits light with wavelengths from e.g. 350 nm to 2500 nm. Broad spectrum light sources with different ranges may be implemented. In an aspect, a broad spectrum light source with a range across 100 nm wavelengths to 2000 nm range of wavelengths in the visible, IR and/or UV frequencies. For example, a broadband tungsten light source for spectroscopy may be used. The spectral response of the reflected light is then measured across the wavelengths in the broad spectrum, e.g. from 350 nm to 2500 nm, concurrently. In an aspect, a charge coupled device (CCD) spectrometer 1030 may be configured to measure the spectral response of the detected light over the broad spectrum.

The spectral response of the reflected light is analyzed for a plurality of wavelengths, e.g. at 10 nm to 15 nm to 20 nm, incremental wavelengths across the wavelengths from 10 nm to 2500 nm. For example, the processing described with respect to FIG. 21 is performed at the plurality of wavelengths. In one aspect, the L values are calculated at incremental wavelengths, such as at 1 nm or 1.5 nm or 2 nm incremental wavelengths. This process may be used to determine one or more wavelengths or ranges of wavelengths useful in detection for one or more substances in the arterial blood flow. For example, a spectral response around a wavelength of 500 nm may have a higher intensity. Trials may then be conducted to determine the one or more substances in the blood that generates this spectral response. In another embodiment, a known substance may be present in the blood and the spectral response across the broad spectrum is then analyzed to determine a pattern or correlation of intensities of wavelengths in the spectral response to the known substance. For example, a pattern of intensities of wavelengths across a range of wavelengths may indicate the presence of a substance. The intensities of the wavelengths may then be analyzed to determine concentration levels of the substance as described in more detail herein.

In another embodiment, the spectral response is analyzed at a set of predetermined wavelengths (or a range of 1 nm to 50 nm including each predetermined wavelength). The L values are calculated for the set of predetermined wavelengths using the analyzed spectral responses. The concentration levels of one or more substances may then be determined based on absorption coefficients for the one or more substances at each of the predetermined wavelengths. The concentration levels of a plurality of substances may be determined using the spectral response of a plurality of frequencies at 2214. The biosensor 150 may thus be used to detect a plurality of substances based on data obtained during a single measurement period. The biosensor 150 may thus perform a blood panel analysis based on in vivo arterial blood flow in a relatively short measurement period of 1-5 minutes. The blood panel analysis may be performed in a physician's office to determine results of the test while the patient is in the office. The biosensor 150 may thus provide blood panel analysis results in a 1-5 minute measurement period without a need for blood samples and lab tests that may take hours or days or weeks to obtain.

Figure 23A:
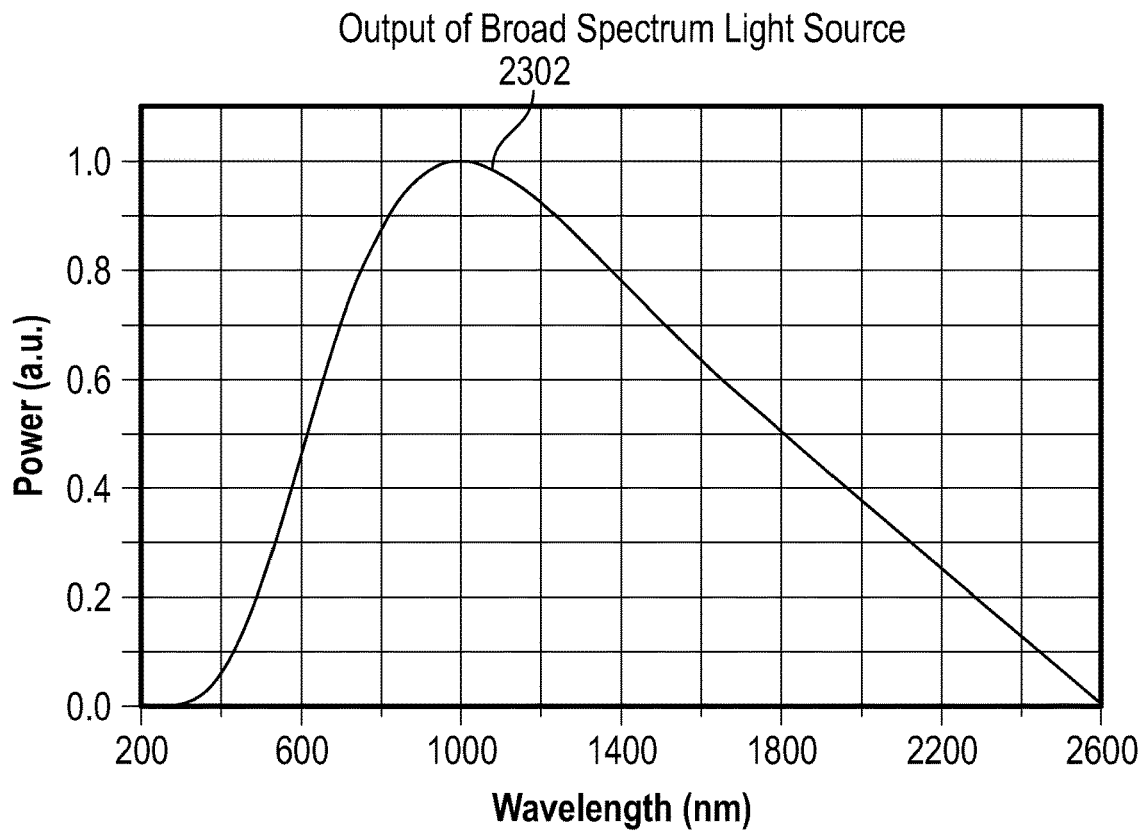
FIG. 23A illustrates a graph of an embodiment of an output of a broad spectrum light source.

FIG. 23A illustrates a graph of an embodiment of an output of a broad spectrum light source. The relative light intensity or power output of the broad spectrum light source is shown versus wavelength of the output light $I_O$. The light intensity or power of the output light extends from wavelengths of approximately 350 nm to approximately 2500 nm. A broad spectrum light source emits light with power across the wavelengths from 350 nm to 2500 nm. Broad spectrum light sources with different ranges may be implemented. In an aspect, a broad spectrum light source with a range across 100 nm wavelengths to 2000 nm range of wavelengths in the visible, IR and/or UV frequencies.

Figure 23B:
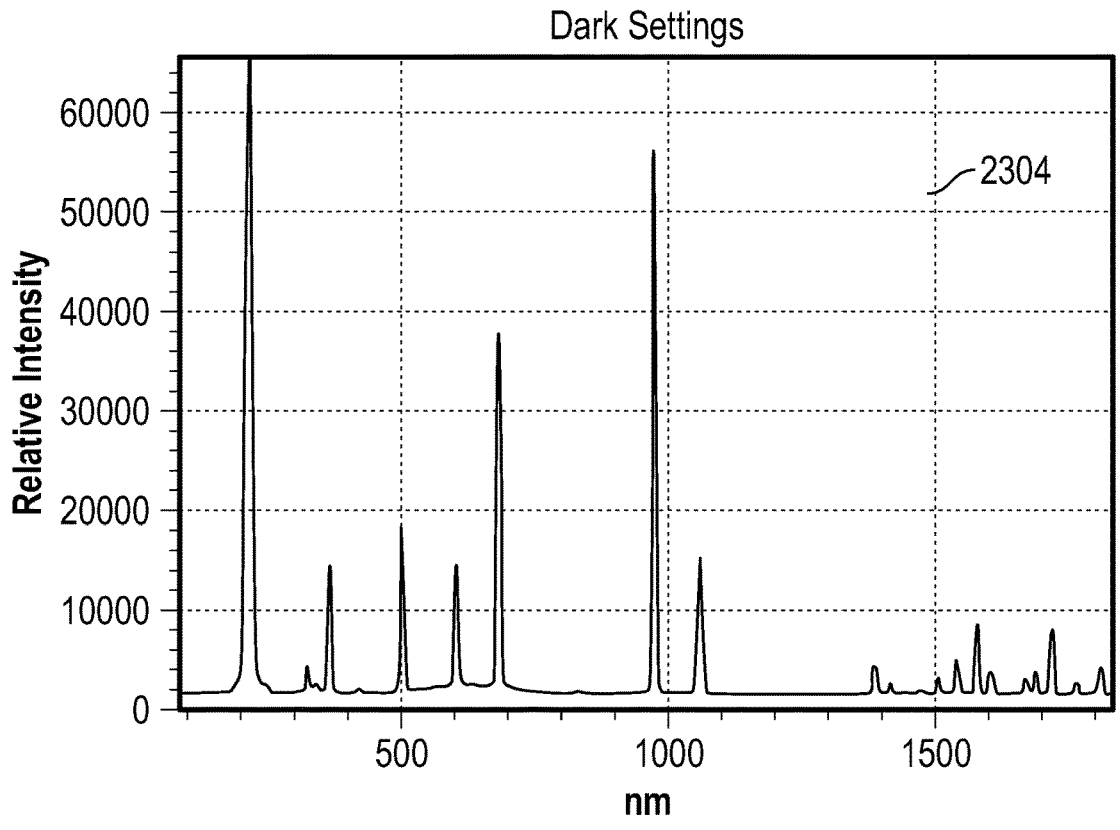
FIG. 23B illustrates a graph with an embodiment of an exemplary spectral response of detected light across a broad spectrum.

FIG. 23B illustrates a graph with an embodiment of an exemplary spectral response of detected light 2304 across a broad spectrum, e.g. from approximately 10 nm to 2000 nm. In one aspect, the spectral response of the detected light 2304 may be analyzed at a plurality of wavelengths, e.g. at a set of predetermined wavelengths or at incremental wavelengths. In another aspect, the spectral response of wavelengths with a detected intensity or power exceeding a predetermined threshold may be analyzed. For example, in the graph shown in FIG. 23B, the spectral response at wavelengths of 200 nm, 680 nm and 990 nm (and ranges of +/−20 to 50 nm around these wavelengths) exceeding a relative intensity threshold of 20000 may be analyzed.

Figure 24:
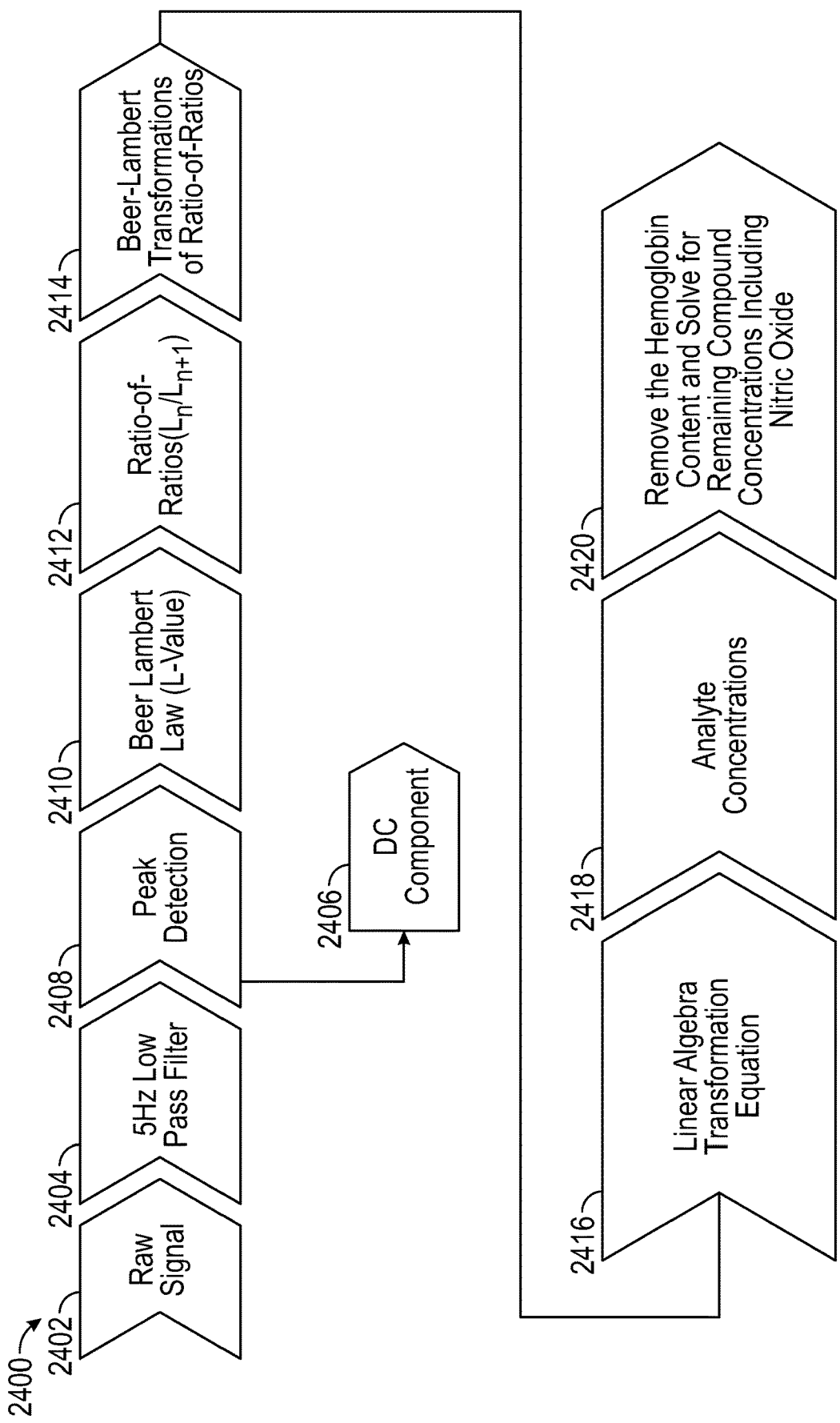
FIG. 24 illustrates a schematic block diagram of an embodiment of a method for determining concentration levels or indicators of substances in pulsating blood flow in more detail.

FIG. 24 illustrates a schematic block diagram of an embodiment of a method 2400 for determining concentration levels or indicators of substances in pulsating blood flow in more detail. The biosensor 150 obtains a spectral response signal at a first wavelength and at a second wavelength at 2402. The spectral response signal includes AC and DC components IAC+DC. A low pass filter is applied to the spectral response signal IAC+DC to isolate the DC component 2406 of the spectral response signal at each wavelength at 2404. The AC fluctuation is due to the pulsatile expansion of the arteriolar bed due to the volume increase in arterial blood. In order to measure the AC fluctuation, measurements are taken at different times and a peak detection algorithm or other means is used to determine the diastolic point and the systolic point of the spectral response at 2408. The systolic and diastolic measurements are compared in order to compute the L values using Beer-Lambert equations at 2410. For example, a logarithmic function may be applied to the ratio of IAC+DC and IDC to obtain an L value for the first wavelength $L_{\lambda 1}$ and for the second wavelength $L_{\lambda 2}$. The ratio R of the first wavelength $L_{\lambda 1}$ and for the second wavelength $L_{\lambda 2}$ may then be calculated at 2412. Beer-Lambert principles are applied to the ratios R at 2414. For example, when multiple frequencies are used to determine a concentration level of one or more substances, the the linear function described herein are applied at 2416, and the one or more concentration levels of the substances or analytes are determined at 2418.

In an embodiment, a substances or analyte may be attached in the blood stream to one or more hemoglobin compounds. The concentration level of the hemoglobin compounds may then need to be subtracted from the concentration level of the substance to isolate the concentration level of the substance from the hemoglobin compounds. For example, nitric oxide (NO) is found in the blood stream in a gaseous form and also attached to hemoglobin compounds. Thus, the measurements at $L_{390\ nm}$ to detect nitric oxide may include a concentration level of the hemoglobin compounds as well as nitric oxide.

The hemoglobin compound concentration levels may be determined and subtracted to isolate the concentration level of the substance at 2420. The hemoglobin compounds include, e.g., Oxyhemoglobin [HbO2], Carboxyhemoglobin [HbCO], Methemoglobin [HbMet], and reduced hemoglobin fractions [RHb]. The biosensor 150 may control the PPG circuit 110 to detect the total concentration of the hemoglobin compounds using a center frequency of 660 nm and a range of 1 nm to 50 nm. A method for determining the relative concentration or composition of different kinds of hemoglobin contained in blood is described in more detail in U.S. Pat. No. 6,104,938 issued on Aug. 15, 2000, which is hereby incorporated by reference herein.

Various unexpected results were determined from clinical trials using the biosensor 150. In one aspect, based on the clinical trials, an R value obtained from the ratio $L_{\lambda1=390\ nm}$ and $L_{\lambda2=940}$ was found to be a predictor or indicator of diabetic risk or diabetes as described in more detail herein. In another aspect, based on the clinical trials, the R value obtained from the ratio of $L_{468\ nm}/L_{940\ nm}$ was identified as an indicator of the liver enzyme marker P450. In another aspect, based on the clinical trials, the R value obtained from the ratio of $L_{592\ nm}/L_{940\ nm}$ was identified as an indicator of digestion phases, such as phase 1 and phase 2, in the arterial blood flow. In another aspect, the R value from the ratio of $L_{660\ nm}/L_{940\ nm}$ was found to be an indicator of oxygen saturation levels $SpO_2$ in the arterial blood flow. In another aspect, it was determined that the biosensor 150 may determine alcohol levels in the blood using spectral responses for wavelengths at 390 and/or 468 nm. In general, the second wavelength of 940 nm is selected because it has a low absorption coefficient for the targeted substances described herein. Thus, another wavelength other than 940 nm with a low absorption coefficient for the targeted substances (e.g. at least less than 25% of the absorption coefficient of the targeted substance for the first wavelength) may be used instead. For example, the second wavelength of 940 nm may be replaced with 860 nm that has a low absorption coefficient for the targeted substances. In another aspect, the second wavelength of 940 nm may be replaced with other wavelengths, e.g. in the IR range, that have a low absorption coefficient for the targeted substances. In general, it is desired that the spectral response for the first predetermined wavelength have a higher intensity level than the spectral response for the second predetermined wavelength.

In another aspect, it was determined that other proteins or compounds, such as those present or with higher concentrations in the blood with persons having cancer, may be detected using similar PPG techniques described herein with biosensor 150 at one or more other wavelengths. Cancer risk may then be determined using non-invasive testing over a short measurement period of 1-10 minutes. Since the biosensor may operate in multiple frequencies, various health monitoring tests may be performed concurrently. For example, the biosensor 150 may measure for diabetic risk, liver enzymes, alcohol levels, cancer risk or presence of other analytes within a same measurement period using PPG techniques.

Figure 25:
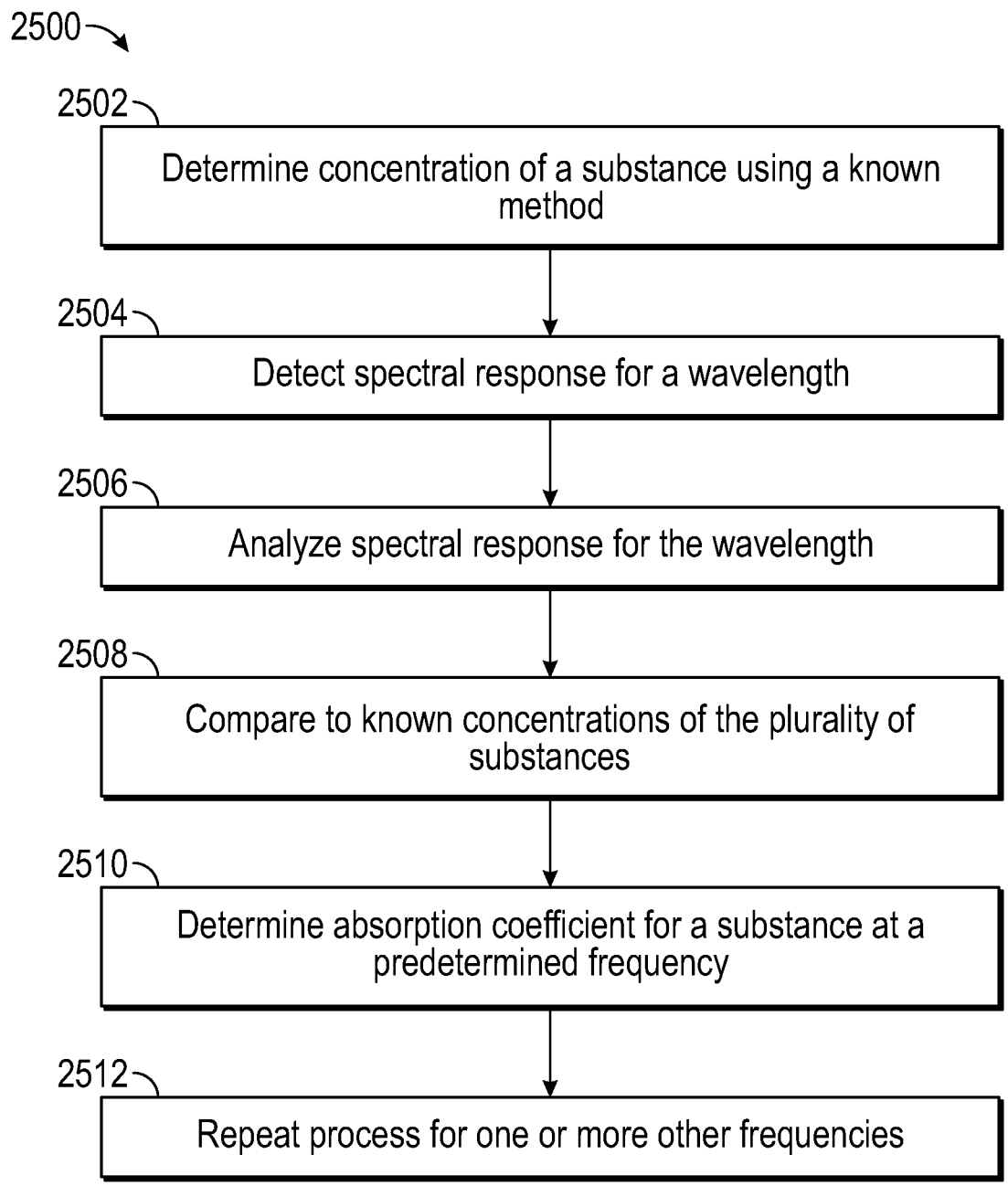
FIG. 25 illustrates a logical flow diagram of an exemplary method to determine an absorption coefficients $\mu$ of a substance at a wavelength $\lambda$.

FIG. 25 illustrates a logical flow diagram of an exemplary method 2500 to determine an absorption coefficients μ of a substance at a wavelength k. The concentration level of a substance in arterial blood is obtained using a known method at 2502. For example, blood may be extracted at predetermined intervals during a time period and a blood gas analyzer may be used to measure a concentration level of a substance. The biosensor 150 emits light at a wavelength (and in one aspect for a range of 1 nm-50 nm around the wavelength) and detects a spectral response for the wavelength (and in one aspect for a range of 1 nm-50 nm around the wavelength) at 2504. The spectral response for the predetermined wavelength is analyzed at 2506. The intensity of the detected light is determined. The intensity of the detected light is compared to the known concentration level of the substance at 2508. The absorption coefficient for the substance may then be determined using the Beer-Lambert equations described herein at 2510.

The above process may be repeated at one or more other frequencies at 2512. For example, as described herein, the spectral analysis over a range or at multiple frequencies may be analyzed to determine one or more frequencies with a higher intensity or power level in response to a concentration level or presence of the substance. Thus, one or more frequencies may be analyzed and identified for detection of the substance, and the absorption coefficient for the substance determined at the one or more frequencies.

In another embodiment, the concentration level of a substance may be obtained from predetermined values obtained through experimentation. For example, in a calibration phase, a correlation table may be compiled through experimentation that includes light intensity values $I_{1-n}$ at one or more wavelengths $\lambda_{1-n}$ and a corresponding known concentration level for the substance for the light intensity values. In use, the biosensor 150 detects a spectral response and determines the light intensity values $I_{1-n}$ at one or more wavelengths $\lambda_{1-n}$. The biosensor 150 then looks up the detected light intensity values $I_{1-n}$ in the correlation table to determine the concentration level of the substance.

Figure 26:
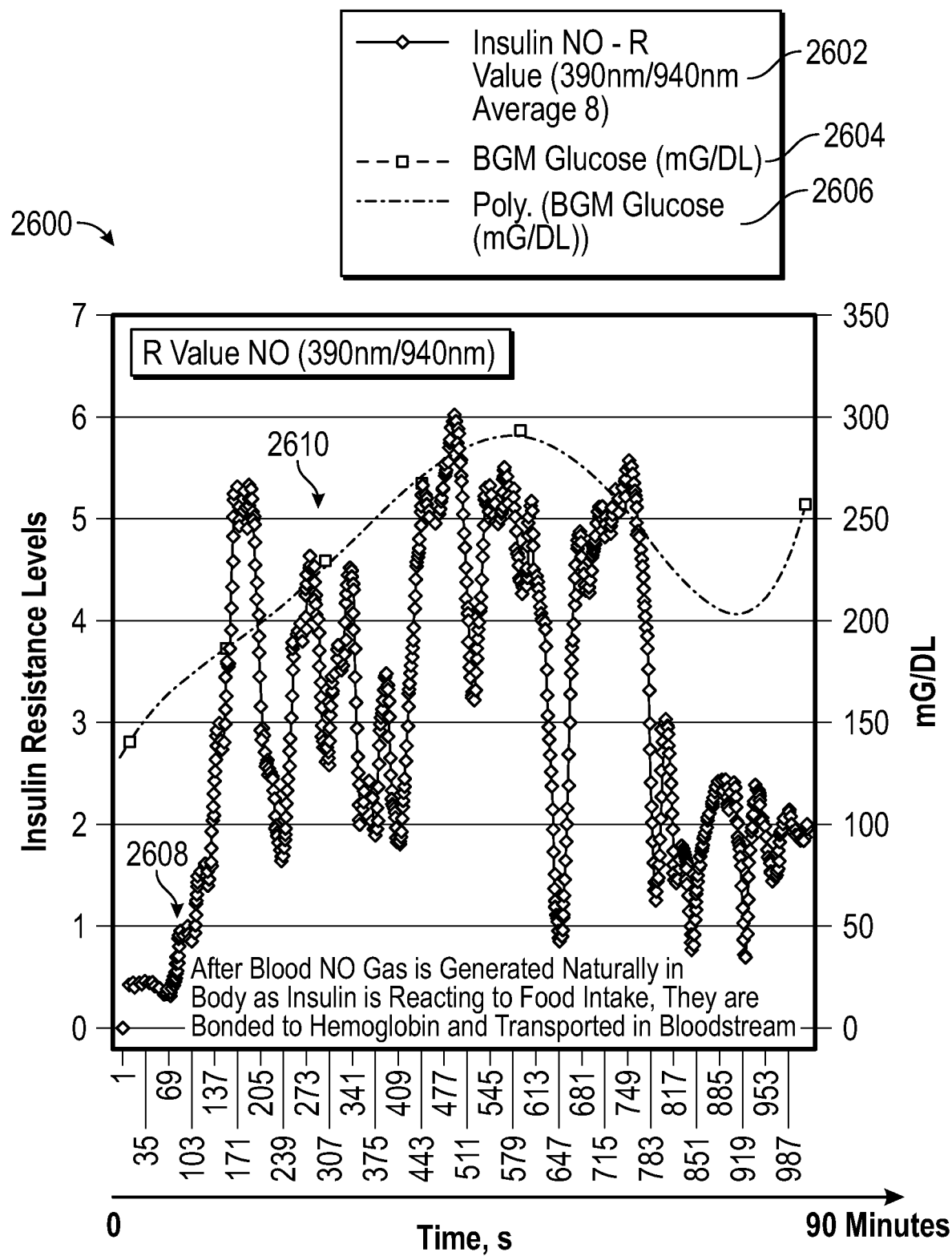
FIG. 26 illustrates a schematic drawing of another exemplary embodiment of results of clinical data obtained using an embodiment of the biosensor from a second patient.

FIG. 26 illustrates a schematic drawing of another exemplary embodiment of results of clinical data 2600 obtained using an embodiment of the biosensor 150 from a second patient. The second patient is a 59 year old male with a known diagnosis of Type 2 diabetes. At predetermined time periods of about 15 minutes, blood glucose level (BGL) was measured using a known method of a blood glucose meter (BGM) using blood from finger pricks. The BGM glucose measurements 2604 are plotted. The plotted measurements were interpolated to generate a polynomial 2606 showing the approximate BGM glucose measurements over time in mG/DL units. The biosensor 150 obtained measurements over the same time period to derive the Ratio R for approximately $L_{390\ nm}/L^{940\ nm}$ 2602, as shown on the graph as well.

In this clinical trial, the base insulin resistance factor 2608 measured prior to eating has a low baseline value of about 0.5 indicating a diabetic condition. In unexpected results, the base insulin resistance factor or R value for $L_{390\ nm}/L_{940\ nm}$ of less than 1 (in an R value range of 0-8) thus seems to indicate a diabetic condition from the clinical trial results. After consumption of a high sugar substance, insulin response 2610 is seen after about 7 minutes. The blood glucose levels may be obtained from the R values using the graph 2600 or a similar calibration table that correlates the R value with known BGL measurements for the patient. The calibration table may be generated for a specific patient or may be generated from a sample of a general population. It is determined that the R values should correlate to similar BGL measurements across a general population. Thus, the calibration table may be generated from testing of a sample of a general population.

From the unexpected results of the clinical trials, an R value of less than 1 (in an R value range of 0-8) indicated that a person has diabetes or early onset of diabetes. An R value of 5 (in an R value range of 0-8) or above indicated that a person has no diabetic condition. For example, as shown in graph 2608, the base insulin resistance factor measured using an R value of approximately $L_{390\,nm}/L_{940\,nm}$ has generally an average value greater than 5 in the first patient without a diabetes diagnosis. The base insulin resistance factor measured using an R value of approximately $L_{390\,nm}/L_{940\,nm}$ was generally an average value less than 1 (in an R value range from 0-8) in the other patients with a diabetes diagnosis of either Type 1 or Type II. The base insulin resistance factor measured using an R value in the 1-2 (in an R value range from 0-8) range indicated a high risk of diabetes and need for further testing.

It seems that the $L_{390\,nm}$ is measuring NO levels in the arterial blood flow. As insulin is generated in the body, it reacts with blood vessels to generate NO gas. The NO gas bonds to hemoglobin and is transported in the blood stream. The NO is thus a good indicator of a base insulin resistance factor after fasting and an insulin response after caloric intake.

From the clinical trials, it seems that the NO levels are reflected in the R values obtained from $L_{390\,nm}/L_{940\,nm}$. Based on the clinical trials and R values obtained in the clinical trials, it is determined that a base insulin resistance factor of less than 1 corresponds to an NO concentration level of at least less than 25% of average NO levels. For example, average NO levels are determined by sampling a general population of persons without diabetes or other health conditions affecting NO levels. From the clinical trials, an R value correlating to a base insulin factor of less than 1 indicates that the NO levels are in a range of 25% to 50% less than average NO levels. After fasting, a person with a diabetic condition will have low NO concentration levels that are at least 25% less than average NO levels due to the low level of insulin in the blood. Thus, an NO concentration level of at least less than 25% of normal ranges of NO concentration levels indicates a diabetic condition (e.g., the NO levels corresponding to R value less than 1 in this clinical trial). Thus, a base insulin resistance factor of less than 1 correlates to at least less than 25% of average NO levels of a sample population and indicates a diabetic condition.

Based on the clinical trials and R values obtained in the clinical trials, it is determined that a base insulin resistance factor in the range of 2-8 corresponds to average NO concentration levels. Thus, a base insulin resistance factor (e.g. in the range of 2-8) correlates to an average NO level of a sample population and little to no diabetic risk.

Based on these unexpected results, in one aspect, the biosensor 150 may display or transmit, e.g. to a user device or monitoring station, or otherwise output an indicator of the diabetic risk of a patient based on the R value. For example, the biosensor 150 may output no diabetic risk based on an obtained R value for a patient of 5 or greater. In another aspect, the biosensor 150 may output low diabetic risk based on an obtained R value of 2-5. In another aspect, the biosensor 150 may output high diabetic risk based on an obtained R values of 1-2. In another aspect, the biosensor 150 may output diabetic condition detected based on an R value less than one. In the clinical trials herein, the R value was in a range of 0-8. Other ranges, weights or functions derived using the R value described herein may be implemented that changes the numerical value of the R values described herein or the range of the R values described herein. In general, from the results obtained herein, an R value corresponding to at least the lower 10% of the R value range indicates a diabetic condition, an R value in the lower 10% to 25% of the R value range indicates a high risk of diabetes, an R value in the 25% to 60% range indicates a low risk of diabetes, and an R value greater than 60% indicates no diabetic condition.

The R value of $L_{390\,nm}/L_{940\,nm}$ may be non-invasively and quickly and easily obtained using the biosensor 150 in a physician's office or other clinical setting or at home. In one aspect, the R value may be used to determine whether further testing for diabetes needs to be performed. For example, upon detection of a low R value of less than 1, a clinician may then determine to perform further testing and monitoring, e.g. using glucose ingestion tests over a longer period of time or using the biosensor 150 over a longer period of time or other type of testing.

Embodiment—Blood Alcohol Level Measurements

Figure 27:
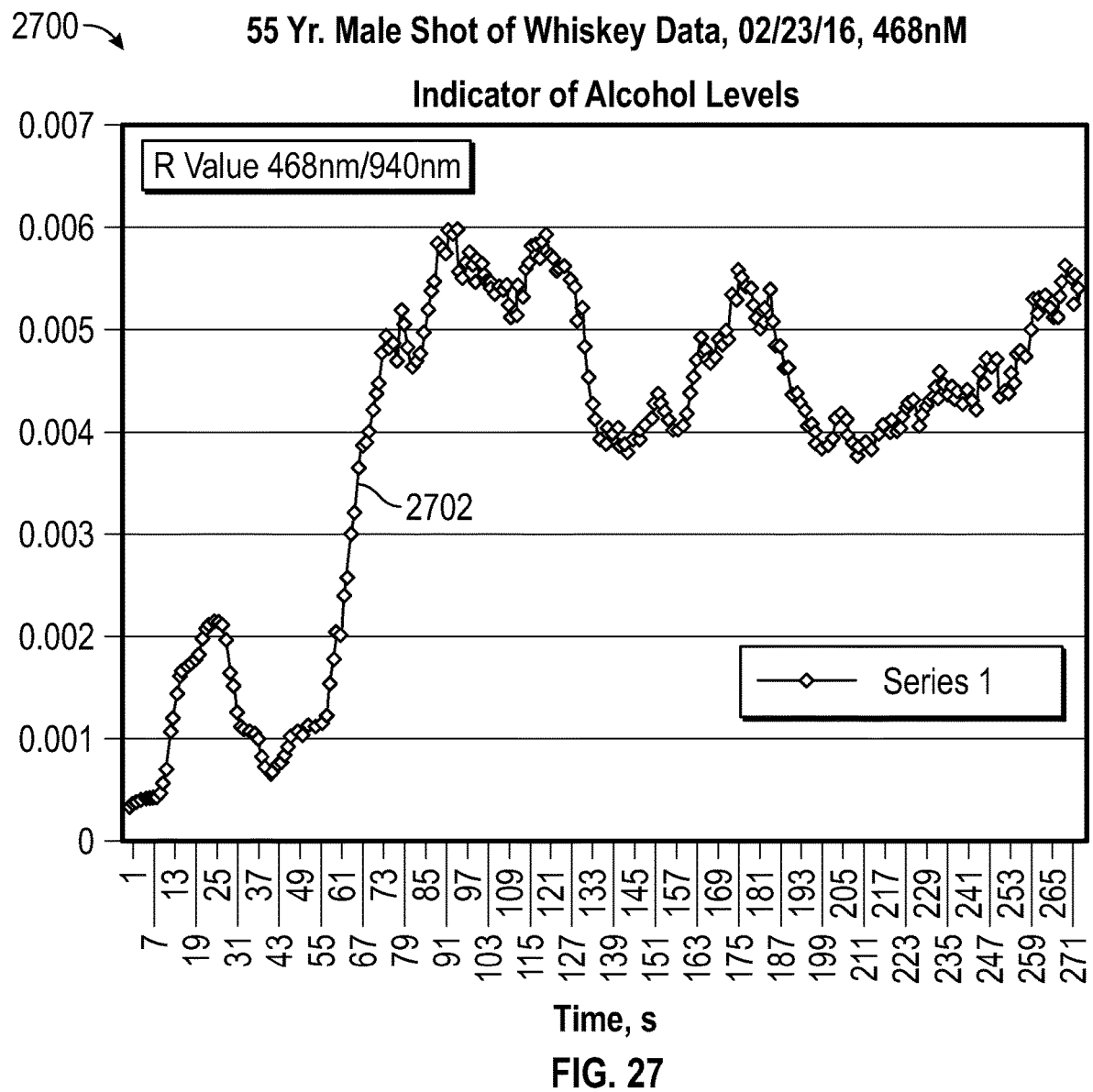
FIG. 27 illustrates a schematic drawing of another exemplary embodiment of results of clinical data obtained using an embodiment of the biosensor from a third patient.

FIG. 27 illustrates a schematic drawing of another exemplary embodiment of results of clinical data 2700 obtained using an embodiment of the biosensor 150 from a third patient. In this trial, the third patient was a 55 year old male that ingested a shot of whiskey at approximately 7 seconds. The biosensor 150 was used to measure an indicator of blood alcohol levels over a measurement period of approximately 271 seconds using a wavelength of approximately 468 nm. The graph illustrates the values obtained for ratio R= $L_{468\,nm}/L_{940\,nm}$ 2702 over the measurement period. The biosensor 150 was able to detect the increase in the blood alcohol levels over the measurement period. The ratio R values 2702 may be correlated with blood alcohol levels using a table or graph that associates the R values 2702 with blood alcohol levels. For example, the table or graph may be obtained through blood alcohol levels measured from blood drawn at preset intervals (such as every 1-5 minutes) during a measurement period (such as 1-5 hours) and interpolating the resulting measurements. The interpolated measurements are then associated with the measured ratio R values 2702 over the same measurement period. In general, the ratio R values 2702 are consistent with an approximate measured blood alcohol level in subsequent clinical trials for a patient. The calibration of measured blood alcohol levels to ratio R values 2702 may thus only be performed once for a patient. In another aspect, the calibration table may be generated using testing of a sample of a general population. It is determined that the R values should correlate to similar BAL measurements across a general population. Thus, the calibration table may be generated from testing of a sample of a general population.

In unexpected results, concentration levels of a liver enzyme called cytochrome P450 Oxidase (P450) that is generated in the presence of alcohol may be measured by the biosensor 150. The spectral response around the wavelength at approximately 468 nm seems to track the concentration levels of the liver enzyme P450. The liver enzyme is generated to react with various substances and may be generated in response to alcohol levels. Thus, the measurement of the spectral response for the wavelength at approximately 468 nm may indicate blood alcohol levels and/or concentration levels of P450.

Embodiment—Digestive Stage and Caloric Intake Measurements

Figure 28:
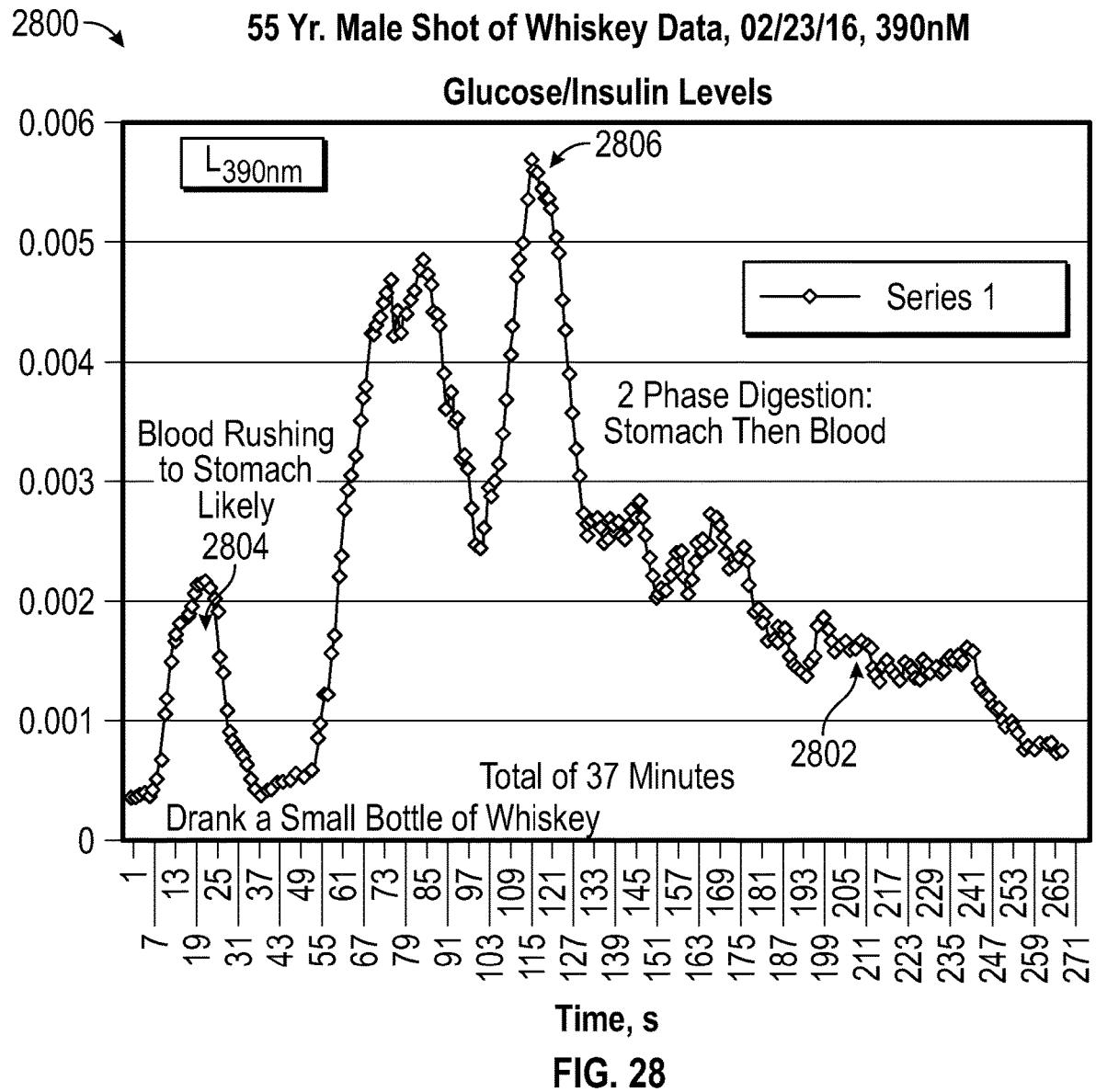
FIG. 28 illustrates a schematic drawing of another exemplary embodiment of results of clinical data obtained using the biosensor from a fourth patient.

FIG. 28 illustrates a schematic drawing of another exemplary embodiment of results of clinical data 2800 obtained using the biosensor 150 from a fourth patient. In this trial, the fourth patient ingested whiskey at approximately 13 seconds. The biosensor 150 was used to measure the digestive stages over a measurement period of approximately 37 minutes using a wavelength of approximately 390 nm to track the blood glucose levels. The graph illustrates the values for $L_{390\ nm}$ 2802 obtained over the measurement period. The biosensor 150 was able to detect the digestive stage 1 2804 and digestive stage 2 2806 based on the obtained values for $L_{390\ nm}$. The first digestive stage 1 2804 is indicated by an initial spike around 20 seconds as blood rushes to the stomach to aid in digestion. The second digestive stage 2 is indicated by a later, more prolonged increase in blood glucose levels between 60 and 180 seconds.

Based on the insulin response and BGL measurements, a calibration of caloric intake may be performed for a patient. For example, known caloric intakes may be correlated with insulin response in phase 1 and phase 2 digestions measured using values for $L_{390\ nm}$ 2802. In another aspect, the calibration table may be generated using testing of a sample of a general population. It is determined that the R values using $L_{390\ nm}$ 2802 and, e.g., $L_{940\ nm}$ should correlate to similar caloric intake measurements across a general population. Thus, the calibration table may be generated from testing of a sample of a general population.

Embodiment—Measurements of Other Substances

Using similar principles described herein, the biosensor 150 may measure concentration levels or indicators of other substances in pulsating blood flow. For example, absorption coefficients for one or more frequencies that have an intensity level responsive to concentration level of substance may be determined. The biosensor 150 may then detect the substance at the determined one or more frequencies as described herein and determine the concentration levels using the Beer-Lambert principles and the absorption coefficients. The L values and R values may be calculated based on the obtained spectral response. In one aspect, the biosensor 150 may detect various electrolyte concentration levels or blood analyte levels, such as bilirubin (using $L_{460\ nm}$) and iron (using $L_{510\ nm}$, $L_{651\ nm}$, $L_{300\ nm}$) and potassium (using $L_{550\ nm}$).

In another aspect, the biosensor 150 may detect sodium chloride NACL (using $L_{450\ nm}$) concentration levels in the arterial blood flow and determine determine dehydration level. The biosensor 150 may then output a determination of level of dehydration based on the detected NACL concentration levels.

In yet another aspect, the biosensor 150 may be configured to detect proteins or abnormal cells or other elements or compounds associated with cancer. The biosensor 150 may measure concentration levels or indicators of other substances in pulsating blood flow using similar principles described herein.

For example, the value $L_{\lambda 1}$ is determined from a spectral response of a wavelength with a high absorption coefficient for the targeted substance. The value $L_{\lambda 2}$ is determined from a spectral response of the wavelength with a low absorption coefficient for the targeted substance. The ratio $L_{\lambda 1, \lambda 2}$ is determined from the value $L_{\lambda 1}$ and the value $L_{\lambda 2}$. A calibration table may be generated using testing of a sample of a general population that correlates values of the ratio $R_{\lambda 1, \lambda 2}$ to concentration levels of the target substance. Then the concentration level of the targeted substance may be determined using the calibration table and the measured values for the ratio $R_{\lambda 1, \lambda 2}$.

Embodiment—White Blood Cell Levels and Detection of Infection

The biosensor 150 may detect white blood cell levels and determine a presence of an infection. For example, the biosensor 150 may detect the various types of white blood cells based on the spectral response of the wavelengths, e.g. using one or more wavelengths shown in Table 1 below.

TABLE 1

Detection of White Blood Cells

| White Blood Cell Type | Diameter | Color | Spectral Absorption Wavelengths |
| --- | --- | --- | --- |
| Neutrophil | 10-12 um | Pink-Red, Blue, White | Red-660 nm Blue-470 nm Green-580 nm |
| Eosinophil | 10-12 um | Pink Orange | 660 nm, 470 nm, 580 nm 600 nm |
| Basophil | 12-15 um | Blue | 470 nm |
| Lymphocyte | 7-15 um | | 633 nm |
| Monocyte | 15-30 um | | 580 nm |

The biosensor 150 may detect a color or color change of the blood due to an increase or decrease in white blood cells using one or more wavelengths described in Table 1. Based on the detected color or color change of the blood, the biosensor 150 may output an alert to a presence of an infection. For example, the biosensor 150 monitors the color of the blood. When it detects a color change indicating an increase in white blood cells, the biosensor determines whether this color change meets a predetermined threshold indicating a presence of an infection. The predetermined threshold may include a color scale and/or length of time of color change. When the color change reaches the predetermined threshold, the biosensor 150 transmits or displays an alert to indicate a presence of an infection.

In another aspect, the biosensor 150 may detect white blood cells from spectral responses at one or more wavelengths. Due to the larger size of the white blood cells from red blood cells, the presence of white blood cells in the blood affects the spectral width and shape of a spectral response.

Figure 29:
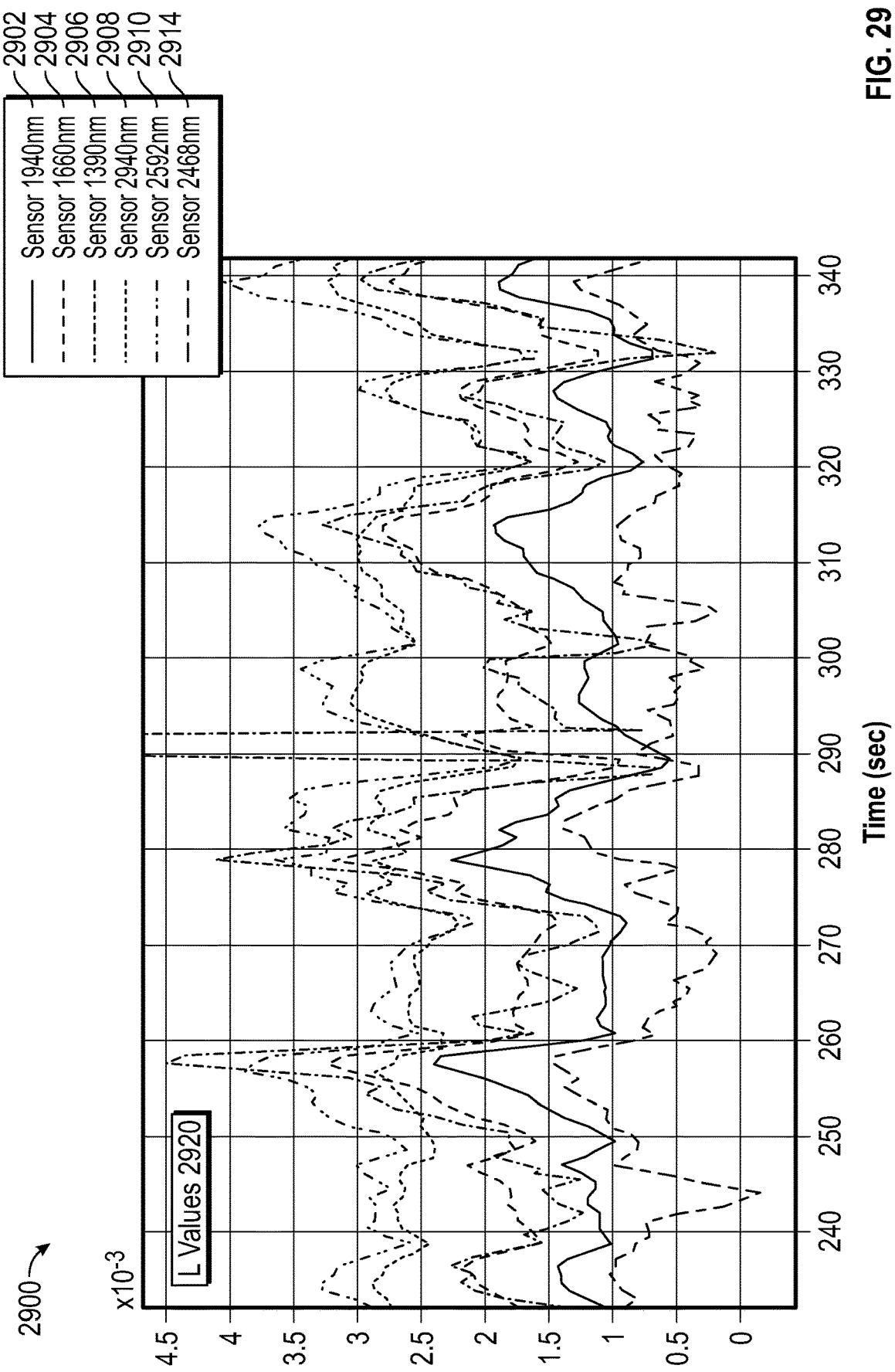
FIG. 29 illustrates an exemplary graph of spectral responses of a plurality of wavelengths from clinical data using the biosensor.

FIG. 29 illustrates an exemplary graph 2900 of spectral responses of a plurality of wavelengths from clinical data using the biosensor 150. In this embodiment, the spectral response of a plurality of wavelengths was measured using the biosensor 150 over a measurement period of almost 600 seconds or approximately 10 minutes. The graph illustrates the L values calculated from the spectral response for a first wavelength 2902 of approximately 940 nm, the spectral response for a second wavelength 2904 of approximately 660 nm and the spectral response for a third wavelength 2906 of approximately 390 nm obtained from a first biosensor 150 measuring reflected light from a first fingertip of a patient. The graph further illustrates the spectral response for a fourth wavelength 2910 of approximately 592 nm and a fifth wavelength 2914 of approximately 468 nm and the spectral response 1408 again at 940 nm obtained from a second biosensor measuring reflected light from a second fingertip of a patient. The spectral responses are temporally aligned using the systolic and diastolic points. Though two biosensors were used to obtain the spectral responses in this clinical trial, a single biosensor 150 may also be configured to obtain the spectral responses of the plurality of wavelengths.

Due to the size of the white blood cells, the presence of white blood cells in the blood affects the spectral width and shape of a spectral response at one or more wavelengths. In one aspect, from L values 2920 shown for the spectral response at 660 nm 2904, the width and shape of the spectral response is affected by the presence of white blood cells. For example, the width and shape of L660 nm between 250 and 270 seconds has a different shape and width of L66 nm between 300 and 320 seconds in the graph 2900. The differences in the width and shape of the spectral response may be used to determine a concentration level of white blood cells or change in concentration level of white blood cells in the blood.

For example, neutrophil levels increase in the presence of an infection. The neutrophil particles have a different color and size from red blood cells. The biosensor 150 may determine an increase in concentration of neutrophil in response to a change in color of the blood or change in the pattern of the spectral response (L value and/or R value) due to change in size of particles in the blood or a combination of both a change in color and change in a pattern of the spectral response (L value and/or R value).

A remote device 100 communicates with one or more external biosensors, such as an ear biosensor and a skin biosensor, to collect and track biosensor data. The remote device may also include integrated biosensors.

A processing circuit includes at least one processing device, such as a microprocessor, micro-controller, digital signal processor, microcomputer, central processing unit, field programmable gate array, programmable logic device, state machine, logic circuitry, analog circuitry, digital circuitry, and/or any device that manipulates signals (analog and/or digital) based on hard coding of the circuitry and/or operational instructions. A memory is a non-transitory memory device and may be an internal memory or an external memory, and the memory may be a single memory device or a plurality of memory devices. The memory may be a read-only memory, random access memory, volatile memory, non-volatile memory, static memory, dynamic memory, flash memory, cache memory, and/or any non-transitory memory device that stores digital information.

As may be used herein, the term "operable to" or "configurable to" indicates that an element includes one or more of circuits, instructions, modules, data, input(s), output(s), etc., to perform one or more of the described or necessary corresponding functions and may further include inferred coupling to one or more other items to perform the described or necessary corresponding functions. As may also be used herein, the term(s) "coupled", "coupled to", "connected to" and/or "connecting" or "interconnecting" includes direct connection or link between nodes/devices and/or indirect connection between nodes/devices via an intervening item (e.g., an item includes, but is not limited to, a component, an element, a circuit, a module, a node, device, network element, etc.). As may further be used herein, inferred connections (i.e., where one element is connected to another element by inference) includes direct and indirect connection between two items in the same manner as "connected to".

As may be used herein, the terms "substantially" and "approximately" provides an industry-accepted tolerance for its corresponding term and/or relativity between items. Such an industry-accepted tolerance ranges from less than one percent to fifty percent and corresponds to, but is not limited to, frequencies, wavelengths, component values, integrated circuit process variations, temperature variations, rise and fall times, and/or thermal noise. Such relativity between items ranges from a difference of a few percent to magnitude differences.

Note that the aspects of the present disclosure may be described herein as a process that is depicted as a schematic, a flowchart, a flow diagram, a structure diagram, or a block diagram. Although a flowchart may describe the operations as a sequential process, many of the operations can be performed in parallel or concurrently. In addition, the order of the operations may be re-arranged. A process is terminated when its operations are completed. A process may correspond to a method, a function, a procedure, a subroutine, a subprogram, etc. When a process corresponds to a function, its termination corresponds to a return of the function to the calling function or the main function.

The various features of the disclosure described herein can be implemented in different systems and devices without departing from the disclosure. It should be noted that the foregoing aspects of the disclosure are merely examples and are not to be construed as limiting the disclosure. The description of the aspects of the present disclosure is intended to be illustrative, and not to limit the scope of the claims. As such, the present teachings can be readily applied to other types of apparatuses and many alternatives, modifications, and variations will be apparent to those skilled in the art.

In the foregoing specification, certain representative aspects of the invention have been described with reference to specific examples. Various modifications and changes may be made, however, without departing from the scope of the present invention as set forth in the claims. The specification and figures are illustrative, rather than restrictive, and modifications are intended to be included within the scope of the present invention. Accordingly, the scope of the invention should be determined by the claims and their legal equivalents rather than by merely the examples described. For example, the components and/or elements recited in any apparatus claims may be assembled or otherwise operationally configured in a variety of permutations and are accordingly not limited to the specific configuration recited in the claims.

Furthermore, certain benefits, other advantages and solutions to problems have been described above with regard to particular embodiments; however, any benefit, advantage, solution to a problem, or any element that may cause any particular benefit, advantage, or solution to occur or to become more pronounced are not to be construed as critical, required, or essential features or components of any or all the claims.

As used herein, the terms "comprise," "comprises," "comprising," "having," "including," "includes" or any variation thereof, are intended to reference a nonexclusive inclusion, such that a process, method, article, composition or apparatus that comprises a list of elements does not include only those elements recited, but may also include other elements not expressly listed or inherent to such process, method, article, composition, or apparatus. Other combinations and/or modifications of the above-described structures, arrangements, applications, proportions, elements, materials, or components used in the practice of the present invention, in addition to those not specifically recited, may be varied or otherwise particularly adapted to specific environments, manufacturing specifications, design parameters, or other operating requirements without departing from the general principles of the same.

Moreover, reference to an element in the singular is not intended to mean "one and only one" unless specifically so stated, but rather "one or more." Unless specifically stated otherwise, the term "some" refers to one or more. All structural and functional equivalents to the elements of the various aspects described throughout this disclosure that are known or later come to be known to those of ordinary skill in the art are expressly incorporated herein by reference and are intended to be encompassed by the claims. Moreover, nothing disclosed herein is intended to be dedicated to the public regardless of whether such disclosure is explicitly recited in the claims. No claim element is intended to be construed under the provisions of 35 U.S.C. § 112(f) as a "means-plus-function" type element, unless the element is expressly recited using the phrase "means for" or, in the case of a method claim, the element is recited using the phrase "step for."

What is claimed is:

1. A remote device, comprising:
    a television control circuit configured to control a television in response to user input; and
    a biosensor, comprising:
        a PPG circuit configured to emit light at a plurality of wavelengths directed at skin of a user and obtain a plurality of spectral responses at each of the plurality of wavelengths of light reflected from the skin;
        a processing circuit configured to:
            process one or more of the plurality of spectral responses at the plurality of wavelengths;
            determine an oxygen saturation level using the one or more of the plurality of spectral responses;
            obtain a value $L\lambda1$ using a first spectral response around a first wavelength with a high absorption coefficient for nitric oxide (NO) levels in blood flow, wherein the value $L\lambda1$ isolates the first spectral response due to pulsating arterial blood flow;
            obtain a value $L\lambda2$ using a second spectral response around a second wavelength with a low absorption coefficient for NO levels in blood flow, wherein the value $L\lambda2$ isolates the second spectral response due to pulsating arterial blood flow;
            obtain a value $R_{\lambda1,\lambda2}$ from a ratio of the value $L_{\lambda1}$ and the value $L_{\lambda2}$;
            determine concentration levels of one or more additional substances in blood flow using the value $R_{\lambda1,\lambda2}$ and a calibration table; and
        a wireless transceiver configured to transmit the biosensor data to the television.

2. The remote device of claim 1, wherein the processing circuit is configured to generate a command to direct the television to display one or more graphical user interfaces including the biosensor data.

3. The remote device of claim 1, wherein the remote device is configured to generate and transmit a command to a remote drug administrative device to administer medicine.

4. The remote device of claim 3, wherein the remote device is configured to generate and transmit the command to the remote drug administration device to administer insulin in response to the biosensor data exceeding a predetermined threshold.

5. The remote device of claim 1, wherein the processing circuit is configured to obtain concentration levels of one or more additional substances in blood flow using the spectral responses by:
    obtaining a concentration level of NO in the blood flow from the value $R_{\lambda1,\lambda2}$.

6. The remote device of claim 5, wherein the processing circuit is configured to obtain concentration levels of one or more additional substances in blood flow using the spectral responses by:
    obtaining a blood glucose concentration level from the value $R_{\lambda1,\lambda2}$ and a calibration table.

7. The remote device of claim 1, wherein the wireless transceiver is configured to transmit the concentration levels of the one or more additional substances to a graphical user interface (GUI) application implemented in a television for display.

8. A device, comprising:
    a control module configured to receive user input and generate control commands to control a television; and
    a biosensor integrated in the device, wherein the biosensor includes:
        a PPG circuit configured to emit light at a plurality of wavelengths directed at skin of a user and obtain a plurality of spectral responses at each of the plurality of wavelengths of light reflected from the skin, wherein at least one of the plurality of spectral responses is obtained at a wavelength with a high absorption coefficient for NO;
        a processing circuit configured to:
            process the spectral responses at the plurality of wavelengths and determine an oxygen saturation level using the spectral responses;
            obtain a value $L\lambda1$ using a first spectral response at the wavelength with a high absorption coefficient for NO, wherein the value $L\lambda1$ includes an alternating current (AC) component of the first spectral response due to pulsating arterial blood flow;
            obtain a value $L\lambda2$ using a second spectral response, wherein the value $L\lambda2$ includes an alternating current (AC) component of the second spectral response due to pulsating arterial blood flow;
            obtain a value $R_{\lambda1,\lambda2}$ from a ratio of the value $L_{\lambda1}$ and the value $L_{\lambda2}$;
            determine concentration levels of NO in blood flow using the value $R_{\lambda1,\lambda2}$; and
        a wireless transceiver configured to communicate the biosensor data and the control commands to the television.

9. The device of claim 8, wherein the processing circuit is configured to generate a command to direct the television to display one or more graphical user interfaces including the biosensor data.

10. The device of claim 8, wherein the processing circuit is configured to generate and transmit a command to a remote drug administrative device to administer medicine in response to the biosensor data.

11. The device of claim 8, wherein the processing circuit is configured to obtain a blood glucose concentration level in blood flow using the NO level and a calibration table.

12. The device of claim 11, wherein the processing circuit is configured to generate and transmit a command to a remote drug administration device to administer insulin in response to the blood glucose concentration level exceeding a predetermined threshold.

13. The device of claim 8, wherein the biosensor further includes an integrated drug administration device that is configured to deliver medication to a patient in response to the biosensor data.

14. A device, comprising:
a biosensor integrated in the device, wherein the biosensor includes:
an optical circuit configured to emit light at a plurality of wavelengths directed at skin of a user and obtain a plurality of spectral responses at each of the plurality of wavelengths of light reflected from the skin, wherein a first spectral response of the plurality of spectral responses is obtained at a wavelength with a high absorption coefficient for NO;
a processing circuit configured to:
process the plurality of spectral responses at the plurality of wavelengths;
determine a heart rate and an oxygen saturation level using the plurality of spectral responses;
obtain a value $L_{\lambda,1}$ using the first spectral response, wherein the value $L_{\lambda,1}$ includes a component of the first spectral response due to pulsating arterial blood flow;
obtain a value $L_{\lambda,2}$ using a second spectral response, wherein the value $L_{\lambda,2}$ includes a component of the second spectral response due to pulsating arterial blood flow;
obtain a value $R_{\lambda 1, \lambda 2}$ from a ratio of the value $L_{\lambda,1}$ and the value $L_{\lambda,2}$; and
determine a concentration level of NO in blood flow using the value $R_{\lambda 1, \lambda 2}$; and
a wireless transceiver configured to communicate the biosensor data to a remote television.

15. The device of claim 14, wherein the processing circuit is configured to generate a command to direct the television to display one or more graphical user interfaces including a history of the biosensor data over a requested period of time.

16. The device of claim 14, wherein the processing circuit is configured to obtain a blood glucose concentration level in blood flow using the NO level and a calibration table.

17. The device of claim 16, wherein the processing circuit is configured to generate a command to direct the television to display an alert message in response to the blood glucose concentration level reaching a predetermined low threshold or in response to the blood glucose concentration level exceeding a predetermined high threshold.

* * * * *